(12) United States Patent
Kaula et al.

(10) Patent No.: US 11,318,316 B2
(45) Date of Patent: May 3, 2022

(54) NAVIGATION OF A HIERARCHICAL USER INTERFACE OF A MEDICAL THERAPY PROGRAMMING DEVICE

(71) Applicant: Cirtec Medical Corp., Brooklyn Park, MN (US)

(72) Inventors: Norbert Kaula, Arvada, CO (US); Yohannes Iyassu, Denver, CO (US)

(73) Assignee: Cirtec Medical Corporation, Brooklyn Park, MN (US)

( * ) Notice: Subject to any disclaimer, the term of this patent is extended or adjusted under 35 U.S.C. 154(b) by 178 days.

(21) Appl. No.: 16/191,392

(22) Filed: Nov. 14, 2018

(65) Prior Publication Data

US 2019/0217107 A1 Jul. 18, 2019

Related U.S. Application Data

(63) Continuation of application No. 15/256,149, filed on Sep. 2, 2016, now Pat. No. 10,159,843, which is a (Continued)

(51) Int. Cl.
| | |
|---|---|
| *G06F 3/0482* | (2013.01) |
| *A61N 1/372* | (2006.01) |
| *G06F 3/04847* | (2022.01) |
| *G16H 40/63* | (2018.01) |
| *G16H 50/50* | (2018.01) |

(Continued)

(52) U.S. Cl.
CPC ..... *A61N 1/37247* (2013.01); *A61N 1/36185* (2013.01); *G06F 3/0484* (2013.01); *G06F 3/0485* (2013.01); *G06F 3/04842* (2013.01); *G06F 3/04847* (2013.01); *G16H 40/63* (2018.01); *G16H 50/50* (2018.01); *G16Z 99/00* (2019.02); *G06F 3/0482* (2013.01); *G16H 20/30* (2018.01)

(58) Field of Classification Search
None
See application file for complete search history.

(56) References Cited

U.S. PATENT DOCUMENTS

| | | | | |
|---|---|---|---|---|
| RE42,814 E | * | 10/2011 | Chu | ........................ G06F 21/34 |
| | | | | 726/34 |
| 2004/0122716 A1 | * | 6/2004 | Yogesan | ................ G16H 30/20 |
| | | | | 705/2 |

(Continued)

*Primary Examiner* — Erica S Lee
(74) *Attorney, Agent, or Firm* — Haynes and Boone, LLP; Eric Li

(57) ABSTRACT

A first fraction of an electrical stimulation is allocated to a first electrode. In response to user input, the first fraction of the electrical stimulation is fixed to the first electrode such that the first fraction is user-adjustable but cannot be automatically changed. In response to the first fraction being fixed to the first electrode, a respective second fraction of the electrical stimulation is automatically allocated to a plurality of second electrodes. The second fraction is a function of the first fraction and a total number of the second electrodes. Thereafter, a new electrode is added to, or deleting from, the second electrodes, while the first fraction is still fixed to the first electrode. The respective second fractions are automatically adjusted in response to the adding or the deleting, without affecting the first fraction of the electrical stimulation that has been fixed to the first electrode.

20 Claims, 60 Drawing Sheets

Related U.S. Application Data continuation of application No. 14/279,841, filed on May 16, 2014, now Pat. No. 9,452,294.

(60) Provisional application No. 61/824,296, filed on May 16, 2013.

(51) Int. Cl.
  *G16Z 99/00* (2019.01)
  *A61N 1/36* (2006.01)
  *G06F 3/04842* (2022.01)
  *G06F 3/0485* (2022.01)
  *G06F 3/0484* (2022.01)
  *G16H 20/30* (2018.01)

(56) References Cited

U.S. PATENT DOCUMENTS

| | | | |
|---|---|---|---|
| 2009/0282346 A1* | 11/2009 | Bechtel | G06Q 10/10 715/751 |
| 2011/0172744 A1* | 7/2011 | Davis | A61N 1/36132 607/62 |
| 2011/0257707 A1 | 10/2011 | Kothandaraman | |
| 2011/0307032 A1 | 12/2011 | Goetz et al. | |
| 2012/0122585 A1* | 5/2012 | Nguyen | G07F 17/3209 463/42 |
| 2013/0131760 A1 | 5/2013 | Rao et al. | |
| 2013/0151280 A1* | 6/2013 | Thiers | G06Q 50/22 705/2 |
| 2014/0067005 A1* | 3/2014 | Kaula | G16H 50/50 607/46 |
| 2014/0191979 A1* | 7/2014 | Tsudik | G06F 3/04883 345/173 |

\* cited by examiner

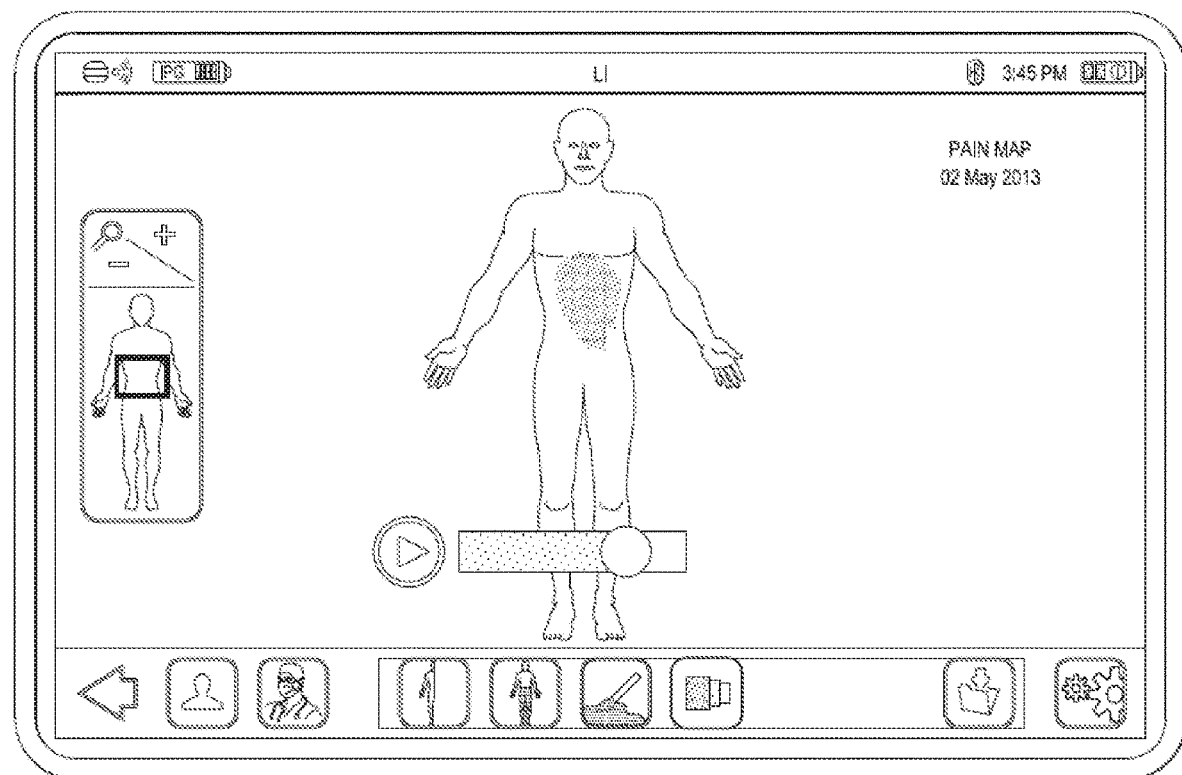

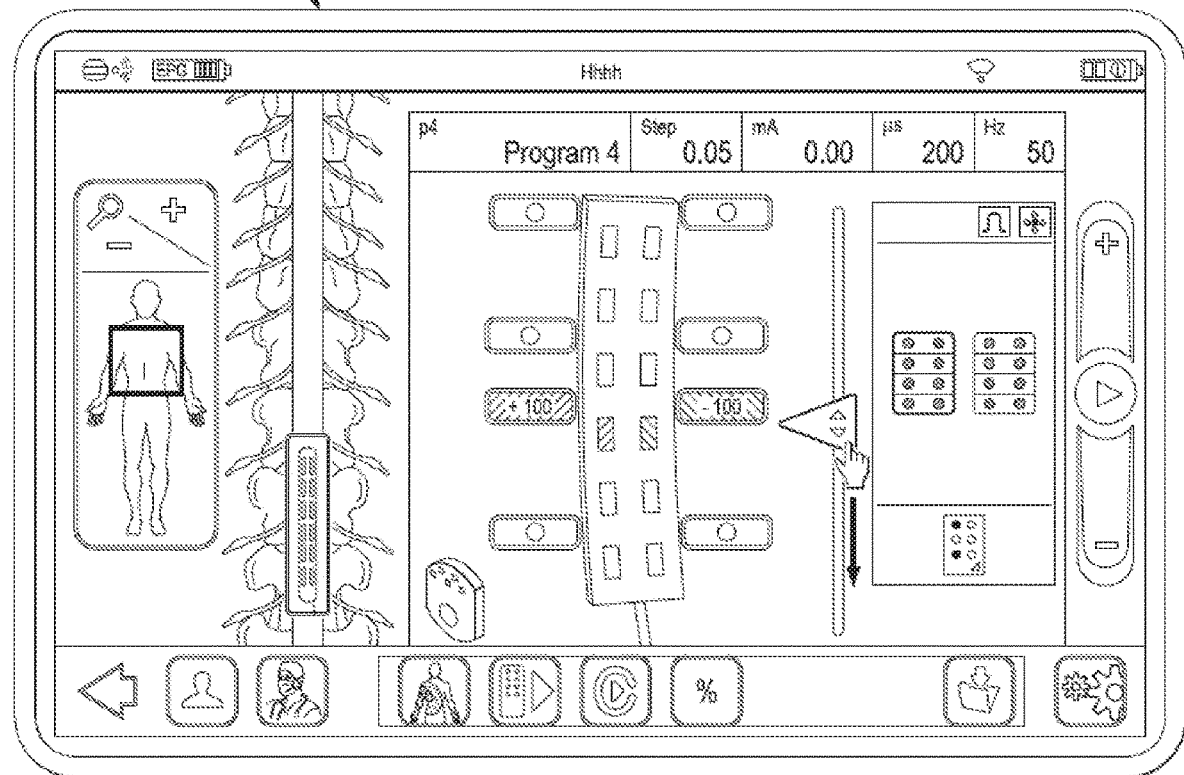

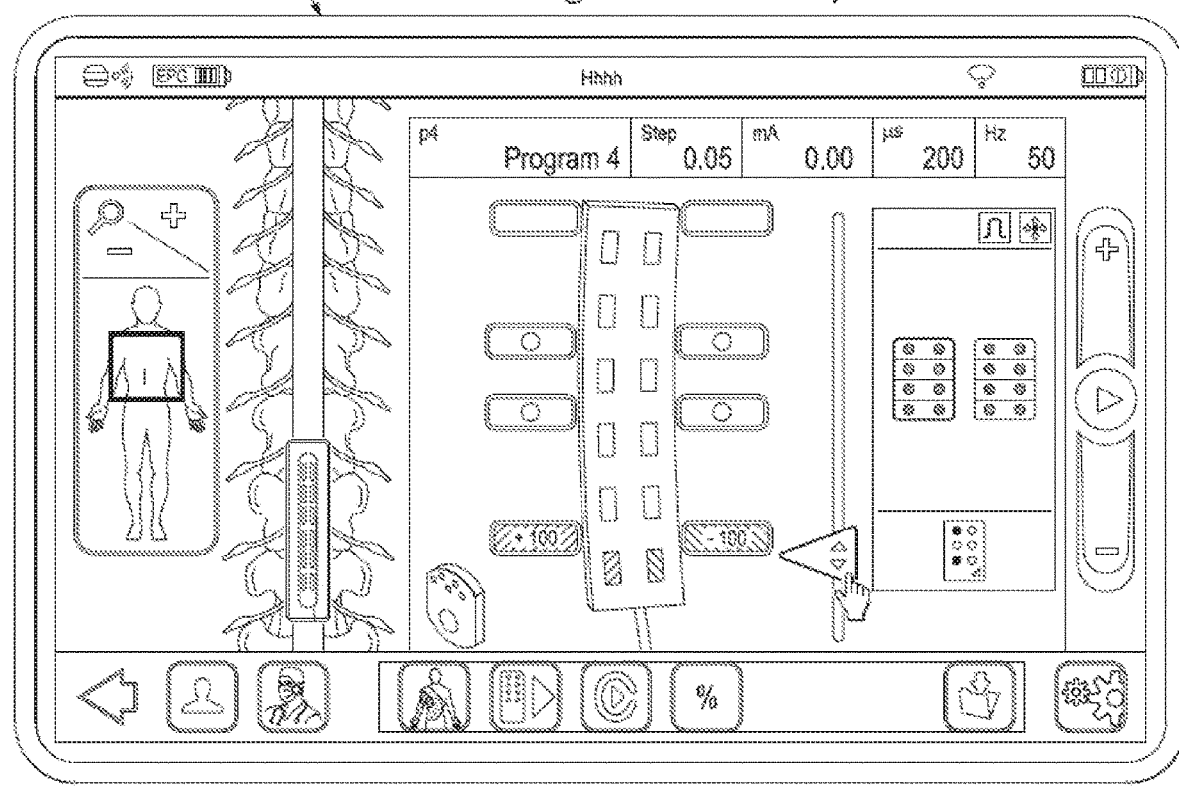

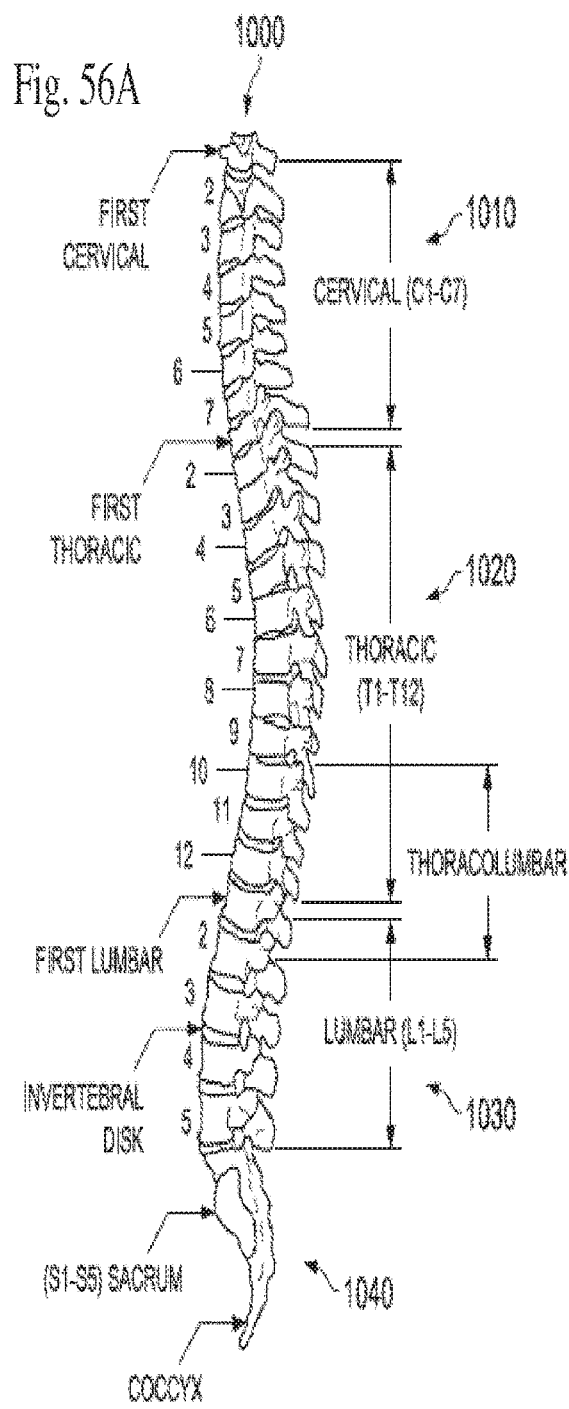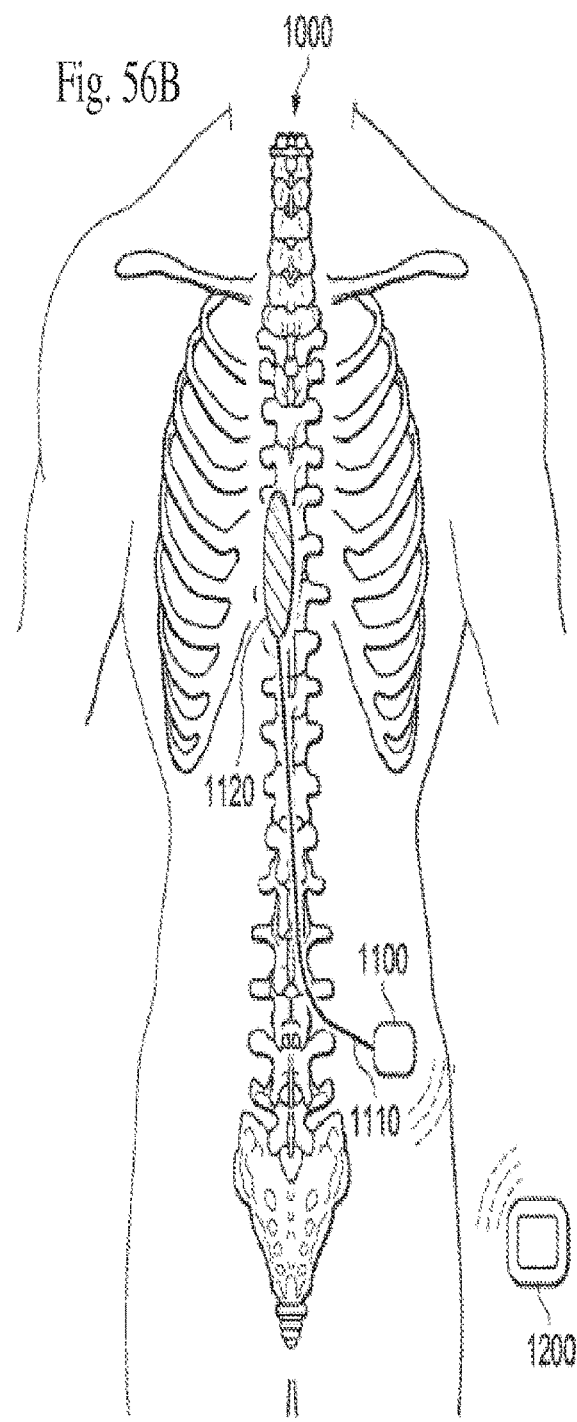

NAVIGATION OF A HIERARCHICAL USER INTERFACE OF A MEDICAL THERAPY PROGRAMMING DEVICE

PRIORITY DATA

The present application is a continuation of U.S. patent application Ser. No. 15/256,149, filed Sep. 2, 2016, which claim priority and benefit of U.S. patent application Ser. No. 14/279,841, filed on May 16, 2014, now U.S. Pat. No. 9,452,294, which claims priority to U.S. Provisional Patent Application No. 61/824,296, filed on May 16, 2013, the disclosures of each which are hereby incorporated by reference in their entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implantable medical devices (for example a neurostimulator) can be controlled using an electronic programming device such as a clinician programmer or a patient programmer. These programmers can be used by medical personnel or the patient to define the particular electrical stimulation therapy to be delivered to a target area of the patient's body, alter one or more parameters of the electrical stimulation therapy, or otherwise conduct communications with a patient. Advances in the medical device field have improved these electronic programmers in certain aspects involving speed and user-friendliness. However, existing electronic programmers still have a variety of shortcomings. For example, existing programmers may not be able to provide accurate and intuitive modeling and may lack features that allow the user to make quick and accurate diagnoses. In addition, the transfer of patient data may be cumbersome and slow.

Therefore, although existing electronic programmers for controlling implantable medical devices have been generally adequate for their intended purposes, they have not been entirely satisfactory in every aspect.

SUMMARY

One aspect of the present disclosure involves a method of programming electrodes on a lead. The method comprises: displaying a virtual representation of a lead, the lead including a plurality of electrodes; selecting a subset of the electrodes for programming, wherein each of the electrodes in the subset has one of two polarities, the two polarities being anode and cathode; assigning, to a first one of the electrodes in the subset, a first percentage of a total stimulation current; fixing, in response to a user input, the first percentage to the first electrode; identifying a plurality of second electrodes in the subset that have the same polarity as the first electrode; and thereafter automatically assigning, to each of the second electrodes, a respective second percentage of the total stimulation current, wherein a sum of the first percentage and the respective second percentages is equal to 100%.

Another aspect of the present disclosure involves an electronic device for programming electrodes on a lead. The electronic device comprises: a memory storage component configured to store programming code; and a computer processor configured to execute the programming code to perform the following tasks: displaying a virtual representation of a lead, the lead including a plurality of electrodes; selecting a subset of the electrodes for programming, wherein each of the electrodes in the subset has one of two polarities, the two polarities being anode and cathode; assigning, to a first one of the electrodes in the subset, a first percentage of a total stimulation current; fixing, in response to a user input, the first percentage to the first electrode; identifying a plurality of second electrodes in the subset that have the same polarity as the first electrode; and thereafter automatically assigning, to each of the second electrodes, a respective second percentage of the total stimulation current, wherein a sum of the first percentage and the respective second percentages is equal to 100%.

Yet another aspect of the present disclosure involves a medical system. The medical system comprises: an implantable medical device, the implantable medical device including a lead having a plurality of electrodes, wherein the implantable medical device is configured to deliver a medical therapy to a patient at least in part via the electrodes; and an electronic device that includes: a graphical user interface configured to receive an input from a user and display a visual output to the user; a memory storage component configured to store computer instructions; and a processor component configured to execute the computer instructions to perform the following tasks: displaying a virtual representation of the lead including the plurality of electrodes; selecting a subset of the electrodes for programming, wherein each of the electrodes in the subset has one of two polarities, the two polarities being anode and cathode; assigning, to a first one of the electrodes in the subset, a first percentage of a total stimulation current; fixing, in response to a user input, the first percentage to the first electrode; identifying a plurality of second electrodes in the subset that have the same polarity as the first electrode; and thereafter automatically assigning, to each of the second electrodes, a respective second percentage of the total stimulation current, wherein a sum of the first percentage and the respective second percentages is equal to 100%; wherein one or more of the displaying, the selecting, the assigning, the locking down, the identifying, and the automatically assigning are performed at least in part via the graphical user interface.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIGS. 2, 3A-3B, 4A-4B, 5A-5B, 6-17, 18A-18B, 19-22, 24-31, 32A-32D, 33-37, and 39-51 are graphical user interfaces on a clinician programmer according to various aspects of the present disclosure.

FIGS. 56A and 56B are side and posterior views of a human spine, respectively.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

In recent years, the use of active implanted medical devices has become increasingly prevalent. Some of these implanted medical devices include neurostimulator devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

Over the years, these electronic programmers have achieved significant improvements, for example, improvements in size, power consumption, lifetime, and ease of use. Nevertheless, the existing programmers still have various shortcomings, for example inaccurate modeling of patient anatomy, imprecise representation of the patient's pain/stimulation regions, inability to view the full medical history of the patient, limited transfer of data to and from the electronic programmer, lack of programming safety controls, and lack of an intuitive user interface.

The present disclosure offers an improved electronic programmer that overcomes the problems associated with existing electronic programmers. The electronic programmer will be discussed in greater detail below with reference to FIGS. 1-2, 3A-3B, 4A-4B, 5A-5B, 6-17, 18A-18B, 19-56 and 57A-57B.

Figure 1:
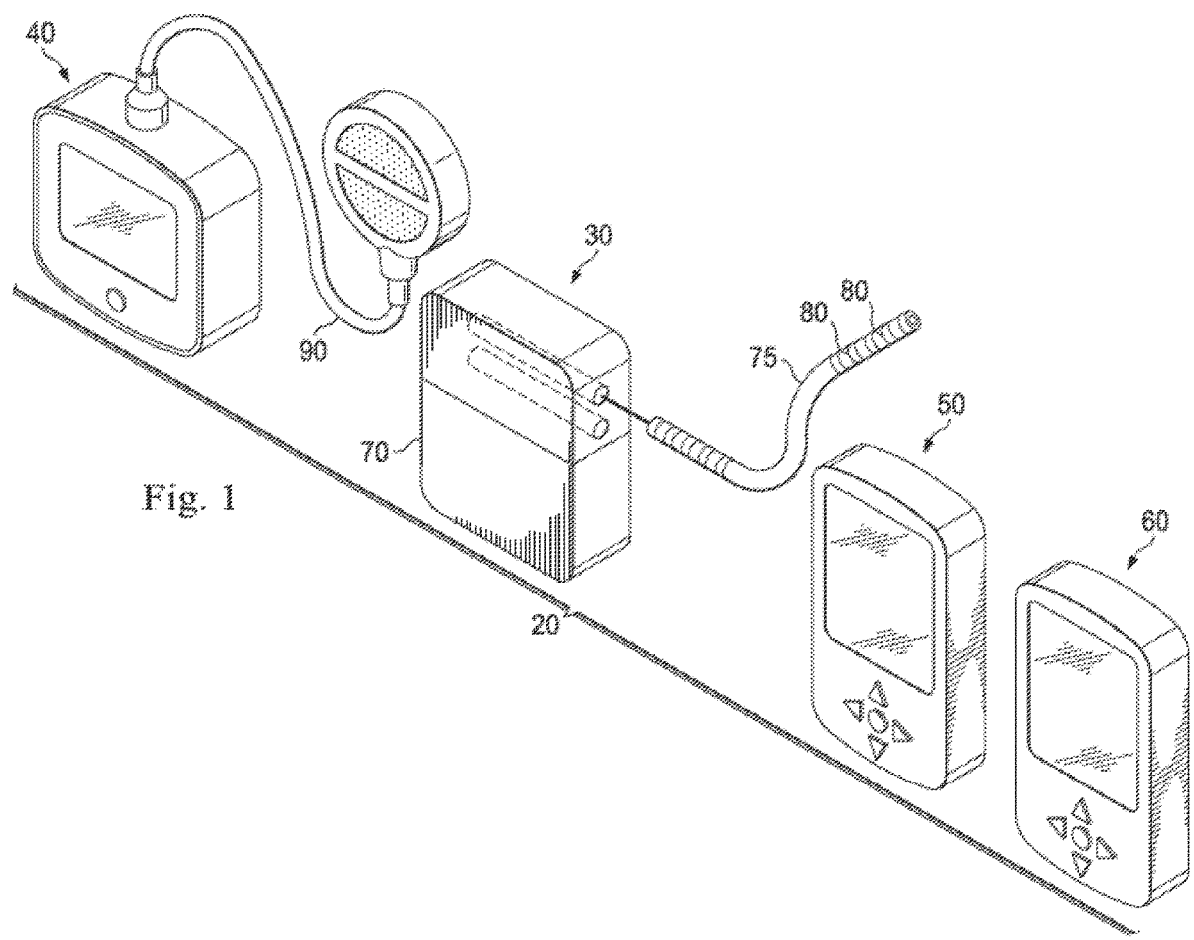
FIG. 1 is a simplified block diagram of an example medical environment in which evaluations of a patient may be conducted according to various aspects of the present disclosure.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters. In some embodiments, patient programmers may include a patient programmer charger (PPC) and/or a pocket programmer (PoP).

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

Various features of the user interface of the clinician programmer 60 will now be described in detail below. In some embodiments, the user interface may be displayed on a screen of a programmer, for example a capacitive or resistive touch-sensitive display. In other embodiments, the user interface may be displayed on a programmer and an external monitor simultaneously, for example in accordance with U.S. patent application Ser. No. 13/600,875, filed on August 31, entitled "Clinician Programming System and Method", the disclosure of which is hereby incorporated by reference in its entirety. As such, both the healthcare provider and the patient are able to view the user interface at the same time.

The various features of the user interface are organized into three sections, with section I pertaining to the modeling and representation of patient anatomy and pain/stimulation regions, section II pertaining to programming options available to a user (e.g., a clinician), and section III pertaining to certain tools and settings available in the user interface. Of course, it is understood that one or more of the features described in any of the sections may be relevant to other sections as well. The placement of any of the features in a particular section is done merely for the sake of simplifying organization of the present disclosure and does not limit the intended scope of that feature in any way.

I. Modeling and Representation of Patient Anatomy and Pain/Stimulation Regions and Implantable Items Customizable Human Body Models Referring to FIG. 2, a user interface 100 of the clinician programmer illustrates a 3D model of a human body 110. The 3D human body model 110 includes an entire human body, though the user interface 100 may be configured to view only a portion of the human body model 110 at a time. The human body model 110 can also be moved in all directions, rotated, resized, or otherwise manipulated. In some embodiments, the human body model 110 is customized for a specific patient. For instance, if a patient is tall (e.g., 6 feet or taller), the human body model 110 may be created (or later resized) to be "taller" too, so as to correspond with the patient's height. As another example, if the patient is overweight or underweight, the human body model 110 may be created (or later resized) to be wider or narrower, so as to correspond with the patient's weight. As other examples, if the patient has particularly long or short limbs, hands/feet, or a specific body build, the human body model 110 may be created (or later resized) to correspond with these body characteristics of the patient as well.

In some embodiments, the present disclosure offers a database that includes a plurality of predefined human body models that each correspond to a specific body type, for example a predefined body type for a 40 year old Caucasian male with a height of 6'1 and a weight of 200 pounds, or a 20 year old African American female with a height of 5'5 with a weight of 120 pounds, so on and so forth. In these embodiments, a healthcare professional or the patient can quickly select a predefined body type from this database that most closely matches his/her physical conditions/characteristics. In this manner, the healthcare professional need not spend too much time specifically customizing the human body model 110 to the patient, since a predefined human body model that is substantially similar to the patient is already available from the database. It is also understood that such database may be available to a network of healthcare professionals and may be downloaded to the electronic programmer upon verifying the necessary login credentials.

FIGS. 3-9 are graphical examples illustrating how a human body model can be customized to more accurately match the physical traits of a patient. FIGS. 3A-3B are graphical illustrations of an implanted medical device (e.g., a paddle lead) relative to a spine of a patient. In FIG. 3A, the patient is a short patient, and therefore the implanted medical device covers more vertebra levels. In comparison, the patient is a tall patient in FIG. 3B, and thus the implanted medical device covers fewer vertebra levels. This is because the spacing between the vertebra levels increase as the patient's height increases, but the length of the implanted medical device will remain the same regardless of the patient's height. Thus, FIGS. 3A-3B highlight the importance of matching the actual patient with a model as closely as possible, as the efficacy of the treatment is dependent on the accurate modeling.

Figure 4B:
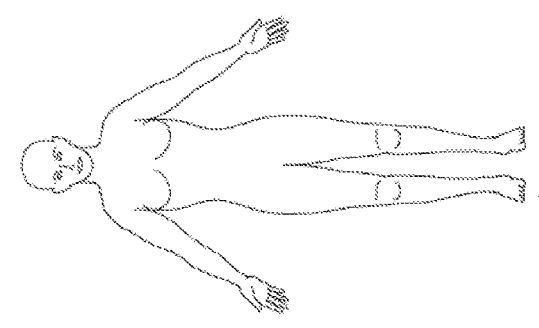
Figure 5B:
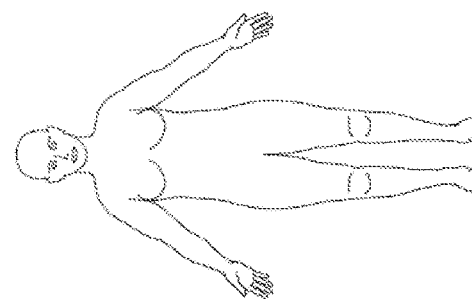
Figure 4A:
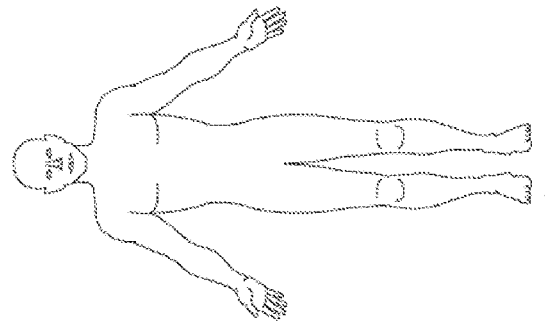
Figure 5A:
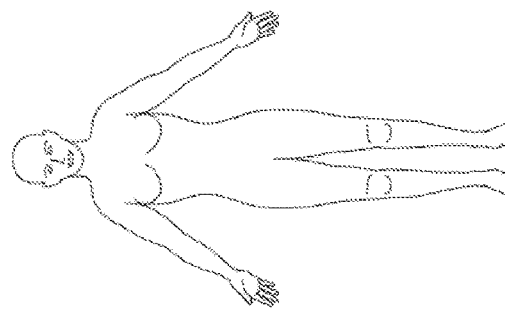
Figures 6, 7:
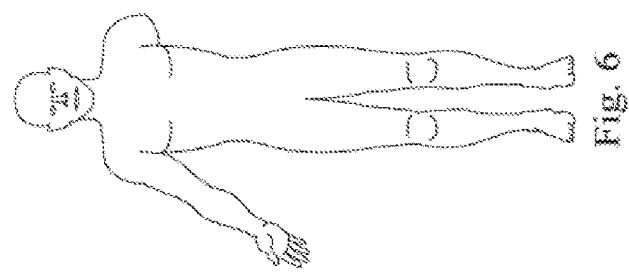
Figure 8:
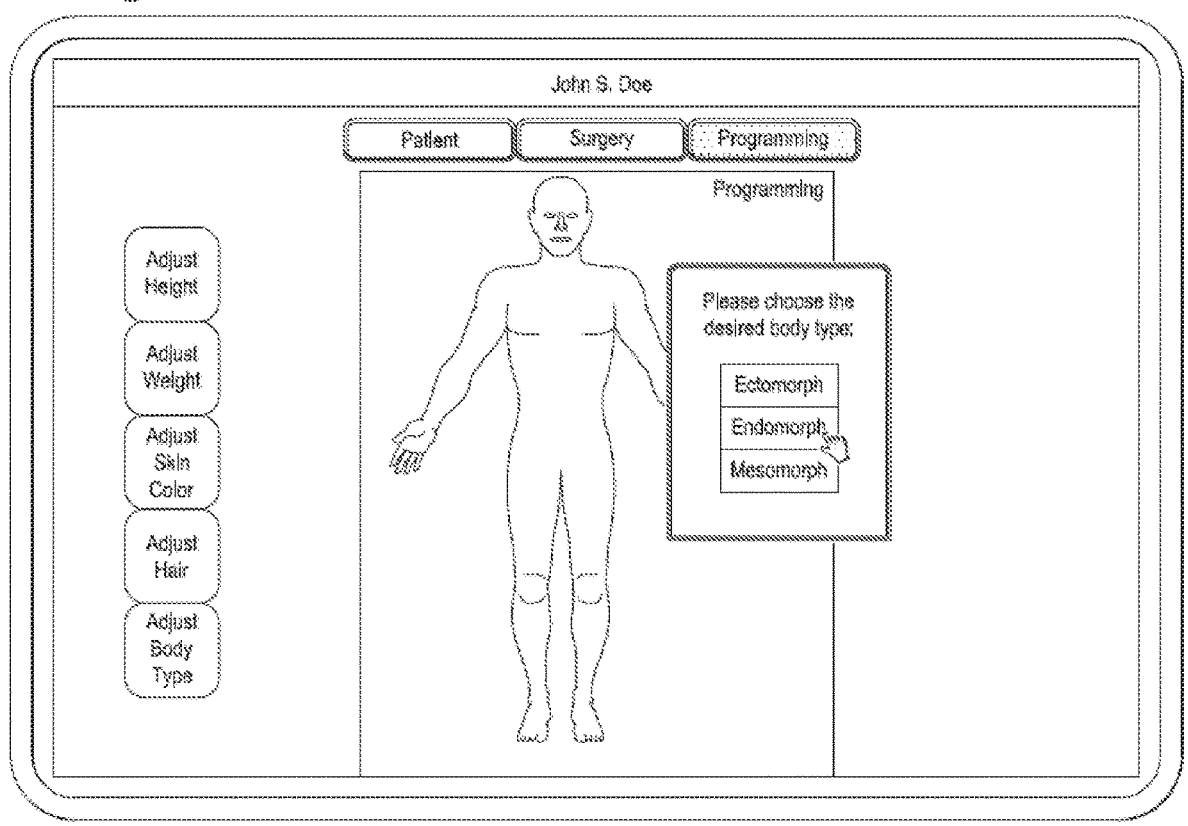

As discussed above, height is not the only variable that can be adjusted in customizing a human body model that closely matches the actual patient. Gender and weight are also among the variables that can be adjusted. As examples, FIG. 4A illustrates a standard male model, FIG. 4B illustrates a standard female model, FIG. 5A illustrates a tall and thin female model, and FIG. 5B illustrates a short and more heavy-set female model. Furthermore, another possible structural adjustment is the removal of appendages, which is illustrated in FIG. 6, where the model is missing a part of his left arm. The removal of appendages may be accomplished by not using all the vertices of the original model, for example. And although not specifically shown for reasons of simplicity, other variables that can be adjusted include skin color, hair color, eye color, etc.

Figure 9:
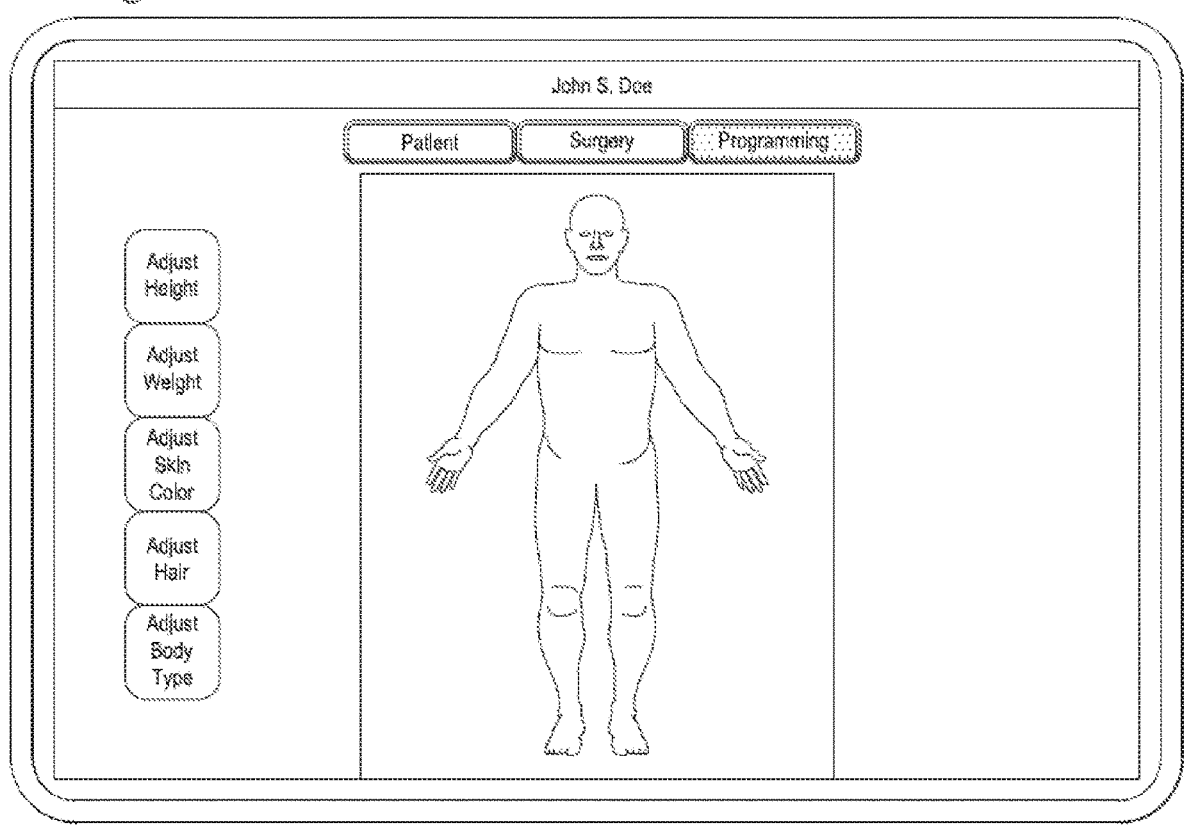

FIG. 7 is an example patient information record in which the user (who may or may not be the patient) may enter patient specifics such as height, weight, gender, body type, etc. discussed above. In some embodiments, the patient record may be used to automatically modify the human body model representing the actual patient. In other embodiments, the user may manually adjust the human body model manually. In yet other embodiments, the user may make manual adjustments to the human body model after a human body model has been automatically generated based on the patient information entered into the patient record. For example, in FIG. 8, a standard male model has been generated for patient "John S. Doe" based on the data entered into his patient record. The user wants to make further manual adjustments to the automatically-generated model, and thus a list of modification options appears, which includes "Adjust Height," "Adjust Weight," "Adjust Skin Color," "Adjust Hair," and "Adjust Body Type." The user wishes to make an adjustment to the body type and selects the option "Adjust Body Type." As a result, a list of body type options appears, which includes "Ectomorph" (heavy/rounded), "Endomorph" (lean), and "mesomorph" (muscular). Referring now to FIG. 9, an adjusted model is shown as a result of the user selecting "Ectomorph." Thus, the model is FIG. 9 is heavier and more rounded compared to the model in FIG. 8 before the adjustment. Of course, these adjustment options discussed above are merely examples, and additional adjustment options are envisioned in other embodiments. Additional details regarding customizing human body models are disclosed in Provisional U.S. Patent Application No. 61/695, 676, filed on Aug. 31, 2012, entitled "Method and System of Adjusting 3D Models of Patients on a Clinician Programmer", the disclosure of which is hereby incorporated by reference in its entirety.

Generation of Pain Maps and Stimulation Maps

Figure 2:
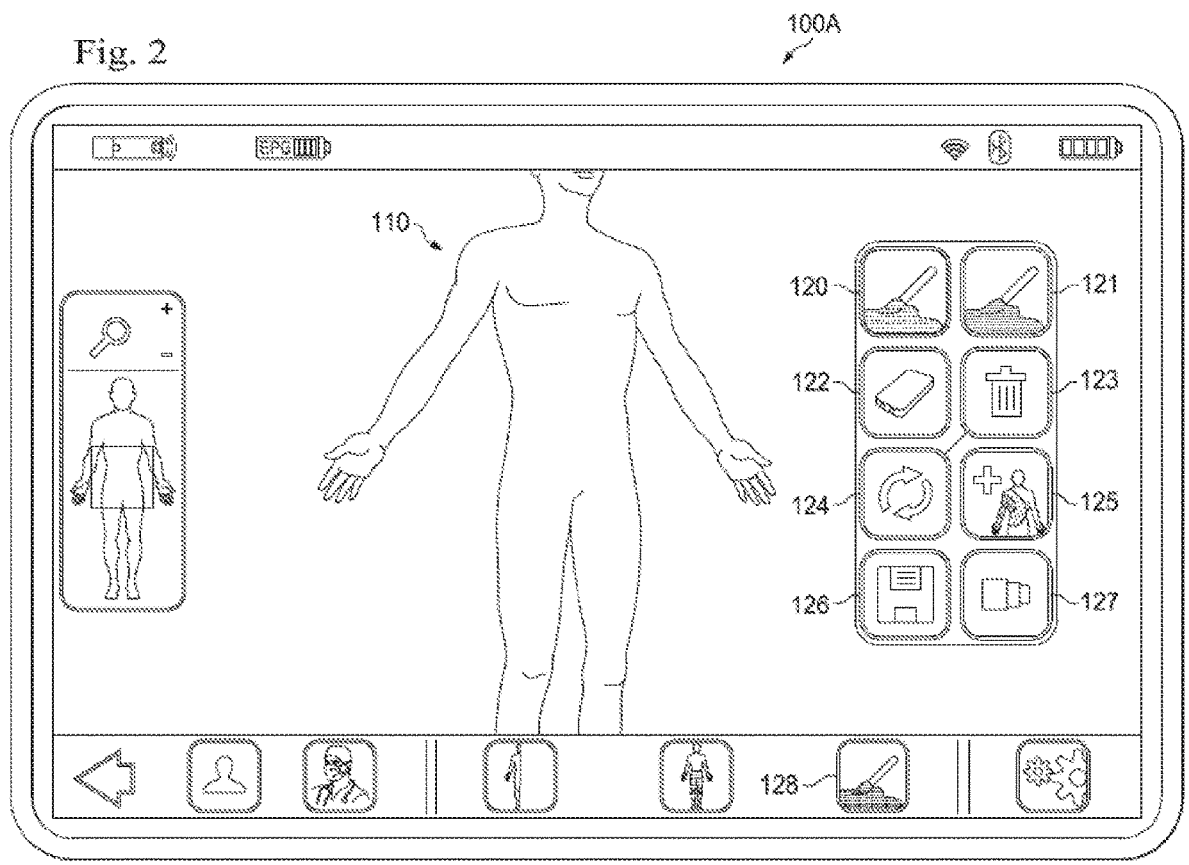
Figure 3A:
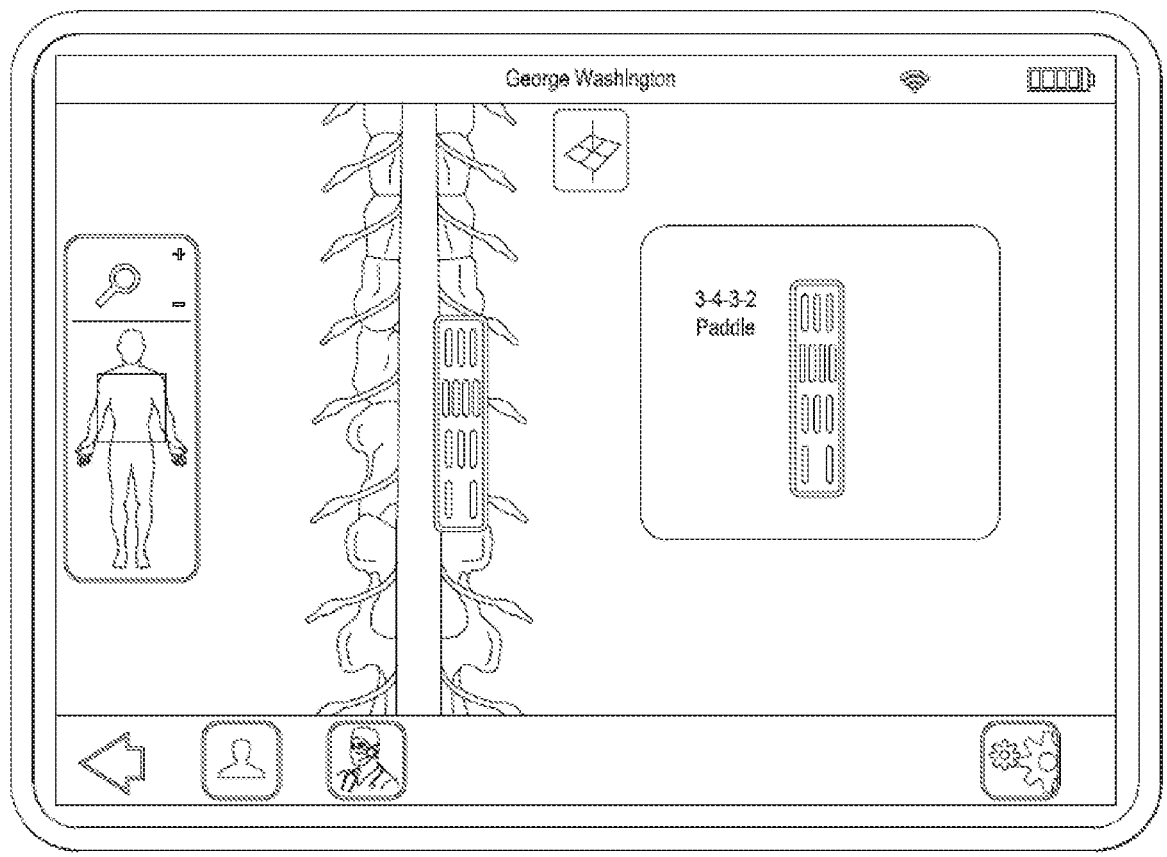
Figure 3B:
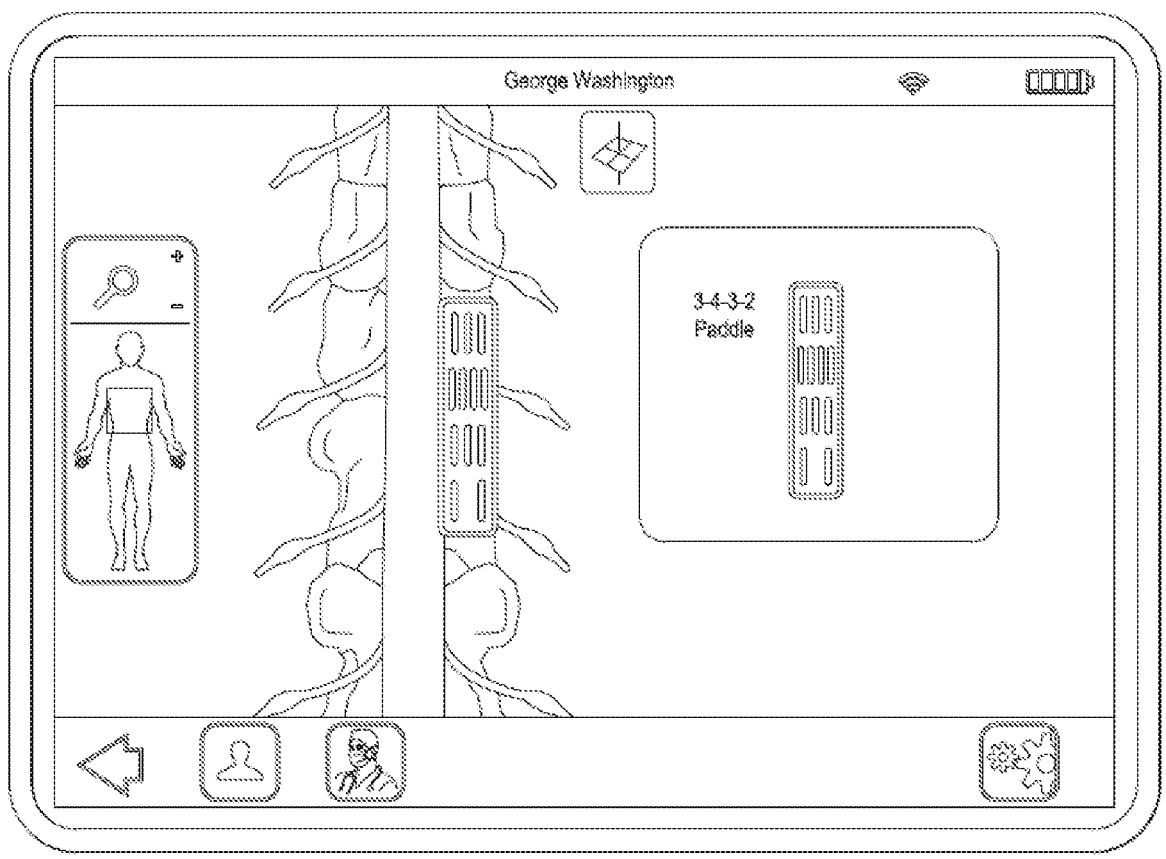

Referring now back to FIG. 2, the user interface 100 also displays a plurality of menu items 120-127 to assist with the generation and display of the pain maps and stimulation maps (not visible in FIG. 2). In the illustrated embodiment, the menu item 120 is used to generate a pain map or a stimulation map. After selecting the menu item 120, the patient can user his/her finger(s) as a simulated brush to draw or paint an area on the human body model 110 that corresponds to a region of pain the patient experiences. For example, if the patient feels pain in his/her shoulder, he/she can paint a pain map on the shoulder region of the human body model 110. The human body model 110 can also be rotated, so that the patient can paint the pain map in different regions of the human body model. The patient may revise the pain map to correspond as closely with the actual perceived regions of pain as possible. To facilitate the painting/drawing of the pain maps, the simulated brush may be of adjustable size.

The stimulation map may be created in a similar manner, except that the stimulation map corresponds with the perceived stimulation experienced by the patient. The pain map and stimulation map are drawn on a touch-sensitive screen in the illustrated embodiment. A graphics accelerator may be used to speed up the generation of these maps.

The menu item 121 is used to indicate the intensity of the pain or stimulation. For example, referring to FIG. 10, after the menu item 120 is used to create a "baseline" pain map that covers a region of the body in general, the menu item 121 (shown in FIG. 2) may be used to indicate a region where the pain is more intense. In the embodiment shown in FIG. 10, the patient may draw a region 140 as a "baseline" pain region. This region 140 may represent the body regions where the patient feels some degree of pain. The patient may also draw a region 142 within the region 142 as an "intense" or "acute" pain region. In other words, the patient may feel much more pain in the region 142 than in the rest of the region 140. The degree of the pain intensity may correspond with a color (or hue) of the region, and a variety of colors may be available to represent different degrees of pain. Thus, a pain map of the present disclosure may reveal various regions with different degrees of pain. In some embodiments, the more painful regions are represented by darker colors, and the less painful regions are represented by lighter colors. The opposite may be true in other embodiments.

Figure 10:
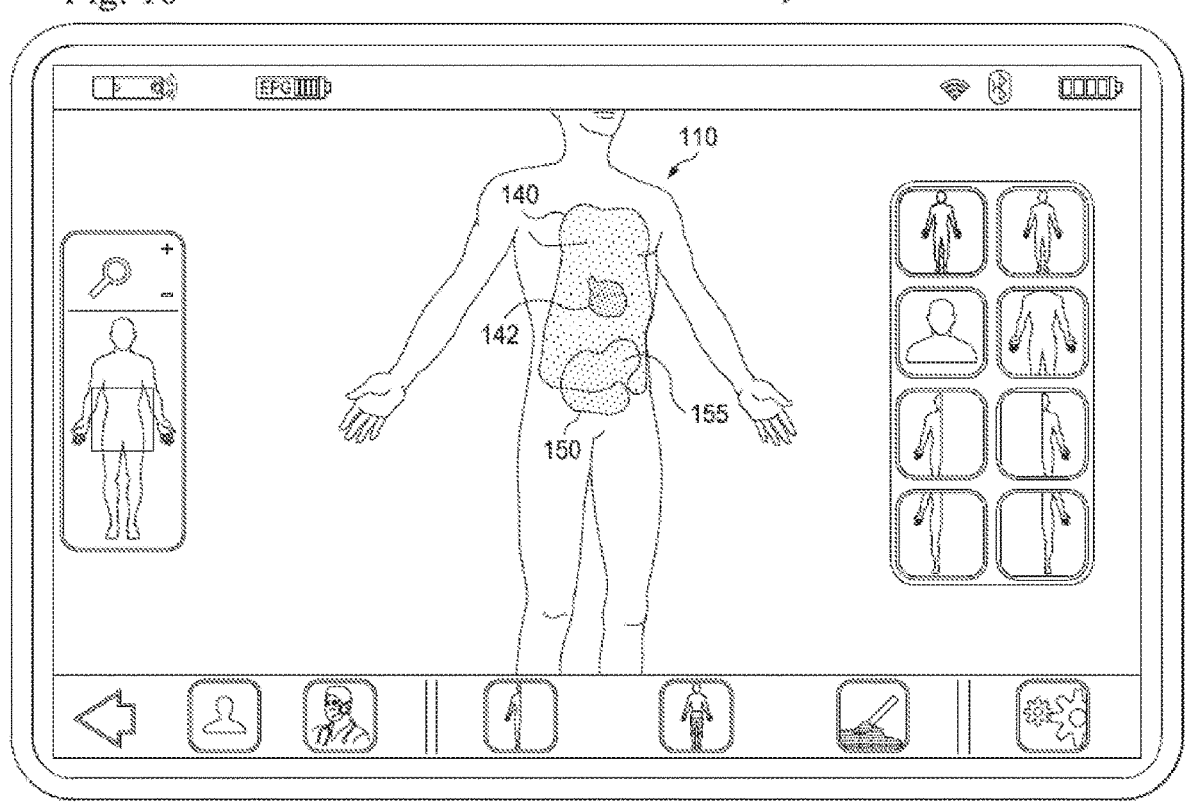

Similarly, the patient may also draw a region 150 to indicate a region on the body where the patient experiences stimulation. Note that the pain region 140 and the stimulation region 150 may be displayed simultaneously, as shown in FIG. 10. An overlapping region 155 (an overlapping between the pain region 140 and the stimulation region 150) may also be displayed, which is helpful in helping the healthcare professional in diagnosing and treating the patient.

It is understood that although pain maps are used as an example herein for illustration purposes, stimulation maps containing regions with different stimulation intensity may be generated in the same manner.

Referring back to FIG. 2, the menu item 122 is used to erase or remove portions of the pain map or the stimulation map. This is done when the patient needs to revise an existing pain map or stimulation map, for example when the pain map or stimulation map is dated and no longer accurately reflects the patient's perceived pain or stimulation.

The menu item 123 is used to delete an existing pain map or stimulation map.

The menu item 125 is used to generate a new pain map or a new stimulation map.

The menu item 126 is used to save changes to a pain map or a stimulation map.

Of course, these menu items 120-127 are merely examples. Some of these menu items may be removed, and other menu items may be added in alternative embodiments to carry out the generation and editing of the pain map and stimulation map.

The present disclosure also allows for predefined pain or stimulation regions. For example, referring now to FIG. 11, the user interface 100 shows a plurality of menu items 160-167 that each correspond to a predefined pain or stimulation region on the human body model 110. For example, in the embodiment shown, the menu item 160 may correspond to a predefined pain region in the right arm of the patient; the menu item 161 may correspond to a predefined pain region in the left arm of the patient; the menu item 162 may correspond to a predefined pain region in the waist and thighs of the patient; the menu item 163 may correspond to a predefined pain region in the abdomen of the patient; the menu item 164 may correspond to a predefined pain region in the right lower leg of the patient; the menu item 165 may correspond to a predefined pain region in the lower left leg of the patient; the menu item 166 may correspond to a predefined pain region in the right foot of the patient; and the menu item 167 may correspond to a predefined pain region in the left foot of the patient.

Figure 11:
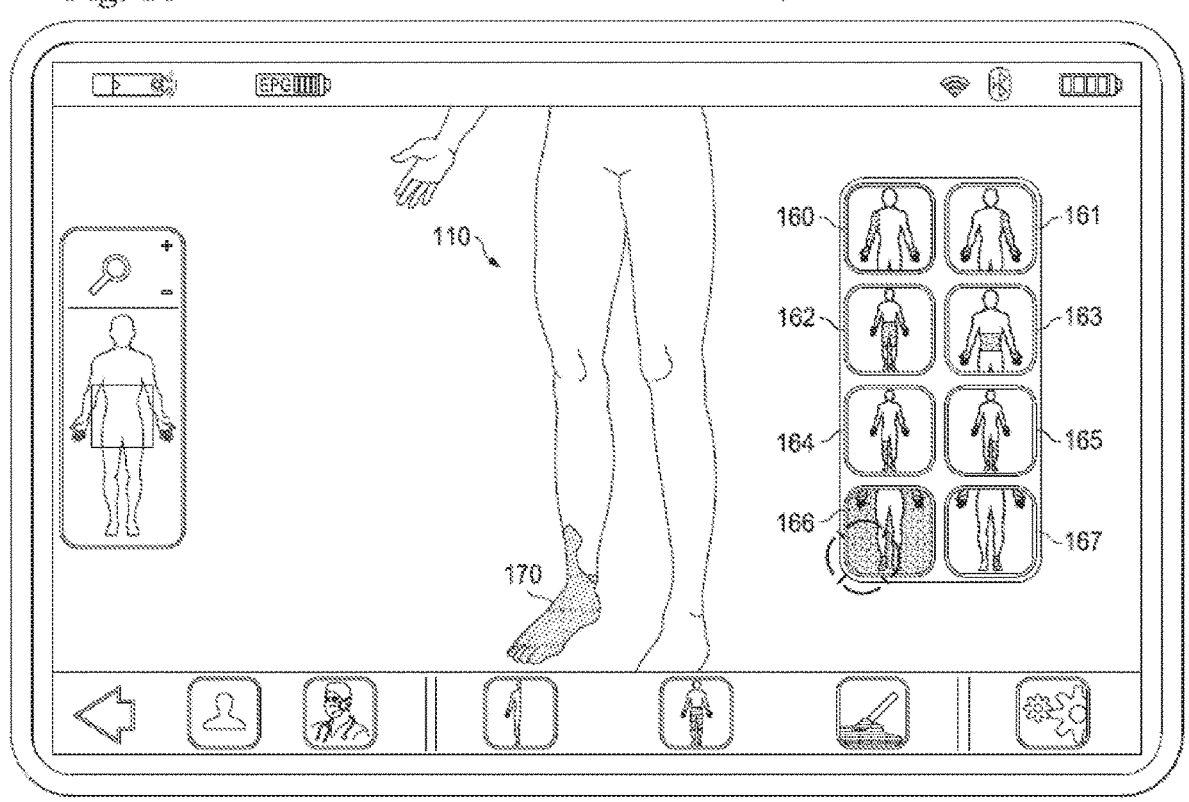
Figure 12:
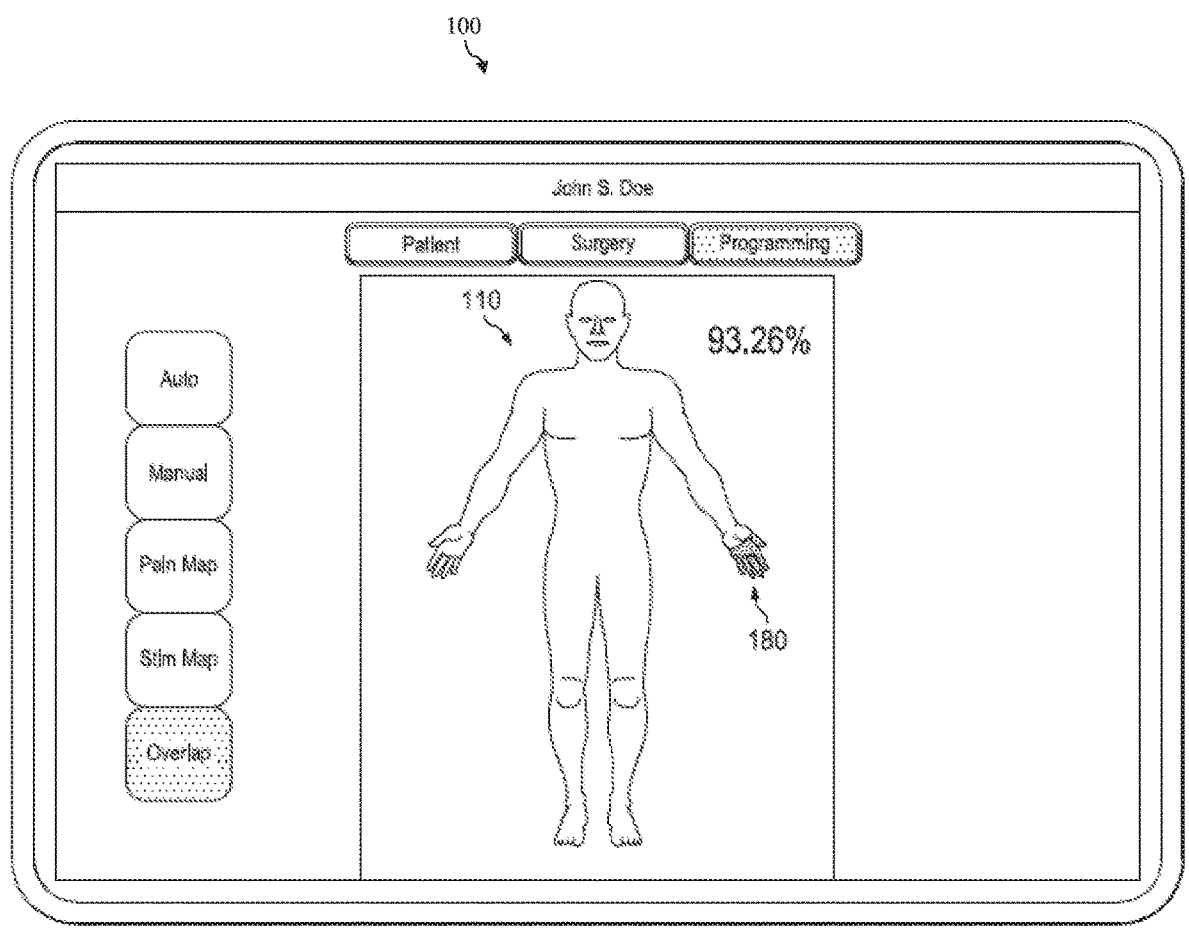

In the embodiment shown in FIG. 11, the menu item 166 is selected, which automatically generates a pain region 170 that covers the right foot of the human body model 110. The pain region 170 can then be revised by the patient to create a pain map that more accurately matches with the pain experienced by the patient. In the same manner, a predefined stimulation region may be automatically generated and then revised to create a desired stimulation map.

The correlations between stimulation parameters (e.g., milliamps, polarity, pulse width, frequency, lead position) or activity parameters (e.g., sitting, standing, sleeping, running, etc.) and perceived stimulation maps are a valuable part of map analysis, because they indicate the degree to which a parameter is related to a certain effect. Map correlations, which can be carried out between individual stimulation programs ("programs") and effective or perceived stimulation maps, are also possible between groups of programs ("programs sets") and an effective stimulation map. A more detailed discussion of stimulation parameters, programs and program sets is found in U.S. patent application Ser. No. 13/601,631, filed on Aug. 31, 2012, and entitled "Programming and Virtual Reality Representation of Stimulation Parameter Groups" to Norbert Kaula, et al., the contents of which are hereby incorporated by reference in its entirety. Furthermore, a detailed discussion of pain/stimulation map generation is found in Provisional U.S. Patent Application No. 61/695,721, filed on Aug. 31, 2012, entitled "Method and System of Creating, Displaying, and Comparing Pain and Stimulation Maps", the contents of which are hereby incorporated by reference in its entirety.

Comparing Pain Map and Stimulation Map Coverage

The present disclosure further allows for a determination of an overlap between a pain map and a stimulation map. For example, referring now to FIG. 12, after a pain map and a stimulation map have been generated, the user interface 100 can be used to determine an overlap 180 between the pain map and the stimulation map. The overlap may vary as a percentage from 0% to 100%. It may be desirable to have a close match between the pain map and the stimulation map, as that may indicate an optimal and efficient stimulation of the pain regions for the patient. For purposes of providing an example, the overlap between the pain and stimulation maps is computed to be at 93.26% in the embodiment shown. In addition, the pain and stimulation maps may be weighted differently, for example by using a slider tool (not illustrated herein), with a readout of the weights.

In various embodiments, any of the maps in Table 1 below may be compared, either one to another, or in combinations.

The possibilities range from maps recorded at the initial session through the current session, and include pain maps (PAIN); stimulation program maps (STIM-Px), where x may vary up to a predetermined number (e.g. 4); and stimulation program set maps (STIM-Sx), where y is determined by the number of programs (x).

For example, if there are three stimulation programs (STIM-P1, STIM-P2, STIM-P3), then there are four possible stimulation program sets (STIM-P1+STIM-P2+STIM-P3, STIM-P1+STIM-P2, STIM-P1+STIM-P3, STIM-P2+STIM-P3).

TABLE 1

| Map List | | |
|---|---|---|
| $PAIN_{init}$ | ... | $PAIN_{curr}$ |
| $STIM\text{-}Px_{init}$* | ... | $STIM\text{-}PX_{curr}$ |
| $STIM\text{-}Sy_{init}$* | ... | $STIM\text{-}Sy_{curr}$ |

*Each stimulation category includes subcategories corresponding to stimulation and the activity parameters discussed above.

Figure 13:
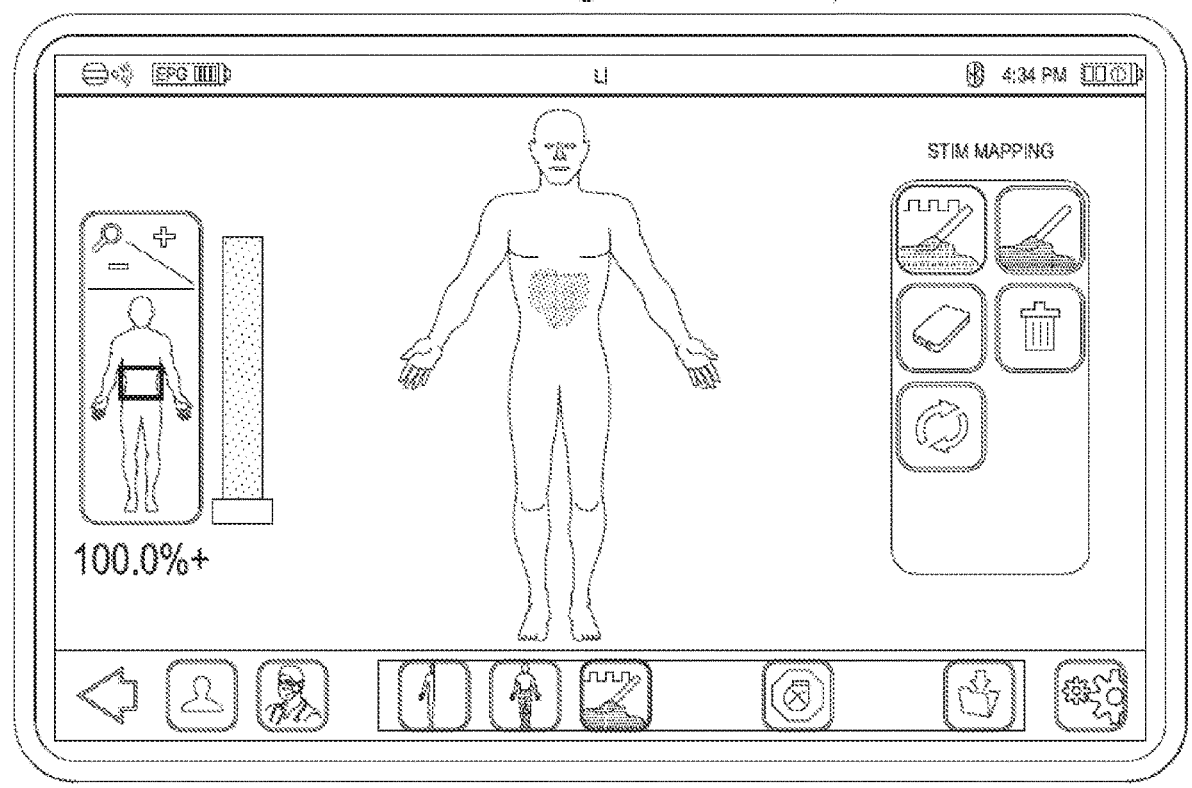

FIG. 13 illustrates another example of the overlap coverage between a pain map and a stimulation map. In this example, the pain map is disposed entirely within the stimulation map. In other words, the stimulation map covers a 100% of the pain map, and its coverage extends beyond the pain map. Therefore, the user interface 100 displays a 100%+ to indicate that 100% of the pain map has been covered by the stimulation map. Note that the 100%+ coverage is not necessarily a good thing. Ideally, the pain map and the stimulation map should have an identical coverage. In that ideal scenario, the stimulation will effectively treat every area of pain, but will not produce unnecessary stimulation (which may be uncomfortable) to areas where the patient feels no pain. In this manner, the pain map and stimulation map overlap coverage will help the user diagnose the effectiveness of the stimulation map coverage, which may then be adjusted or fine-tuned by the user for further improvement.

A Plurality of Available Human Body Model Starting Locations

Figure 14:
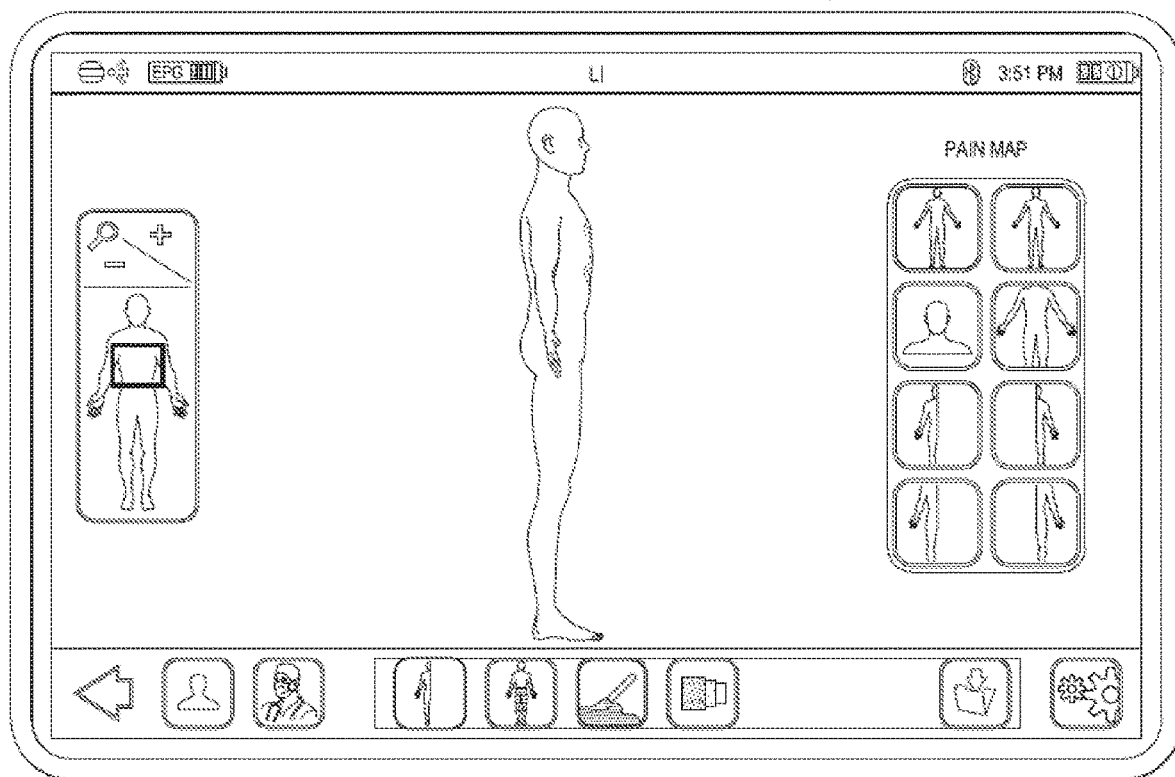
Figure 15:
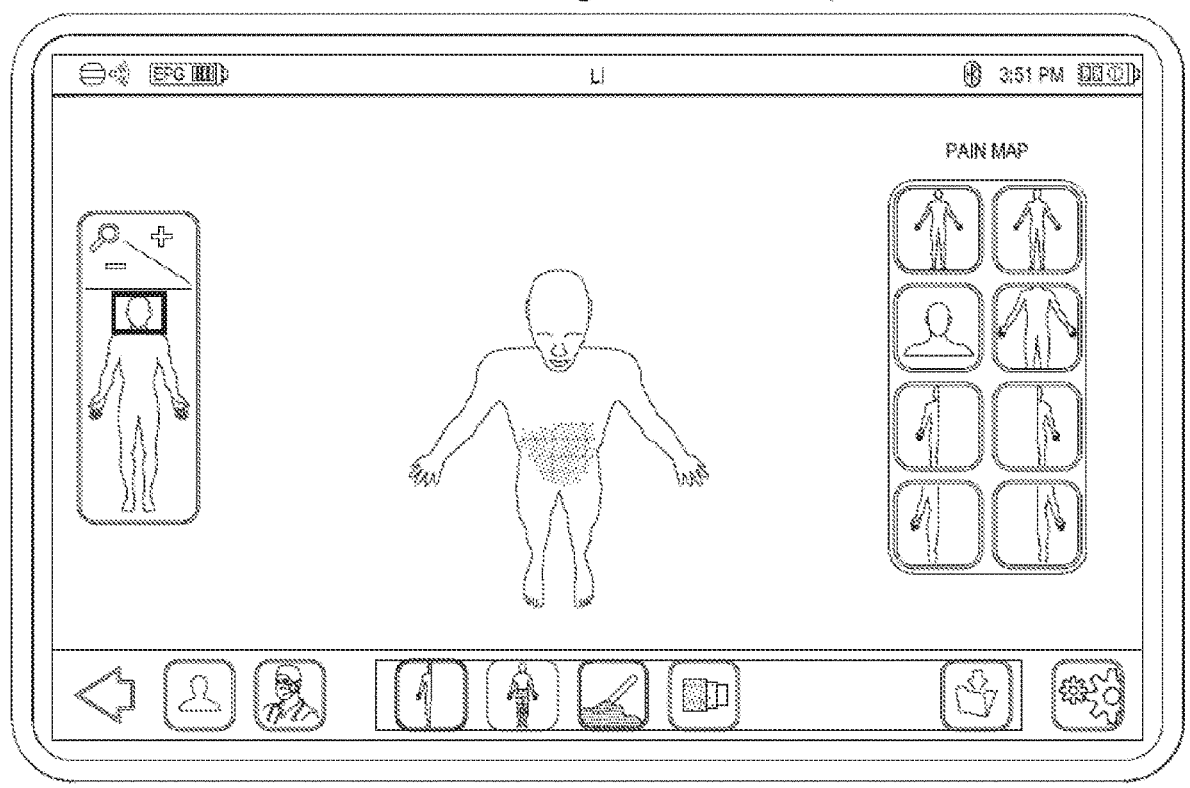

According to various aspects of the present disclosure, the human body model used to generate the pain map and stimulation map may also have a plurality of predefined starting locations for the user to choose from. FIGS. 14-15 illustrate some of these predefined starting locations as examples. As shown in FIGS. 14-15, a plurality of icons appear on the right side of the user interface 100. Each of the icons corresponds to a particular portion of the human body model. As the user clicks on a particular icon, the corresponding portion of the human body model will be selected as the starting locations for the human body model on which a stimulation map and/or a pain map and be drawn. In FIG. 14, the user clicks on the "right hand" icon, and correspondingly the human body model shown in the user interface 100 is automatically adjusted to have the right hand of the human body model face the user. In FIG. 15, the user clicks on the "head" icon, and correspondingly the human body model shown in the user interface 100 is automatically adjusted to have the head of the human body model face the user. In each case, a target starting location is automatically provided for the user in a quick and convenient manner. It is understood that the user may also manually manipulate the human body model—for example by rotating, moving, or resizing it—to arrive at a desired target starting location to generate the pain map or stimulation map. But that process takes time, and these available starting locations provide more convenience for the user and thereby render the pain/stimulation map generation process more user friendly.

Visualization of Migration History of Pain Maps and Stimulation Maps

The pain maps and stimulation maps as discussed above can be stored in a database. In some embodiments, the database resides on the clinician programmer itself. In some other embodiments, the database resides on a remote server, i.e., the cloud. In yet some other embodiments, the database resides on an implantable medical device, for example an implantable pulse generator. It is also understood that the database, or a portion thereof, may be simultaneously stored in more than just one location. For example, the database (or portions thereof) may be simultaneously stored in the clinician programmer, the remote server, and the implantable medical device.

Figure 16:
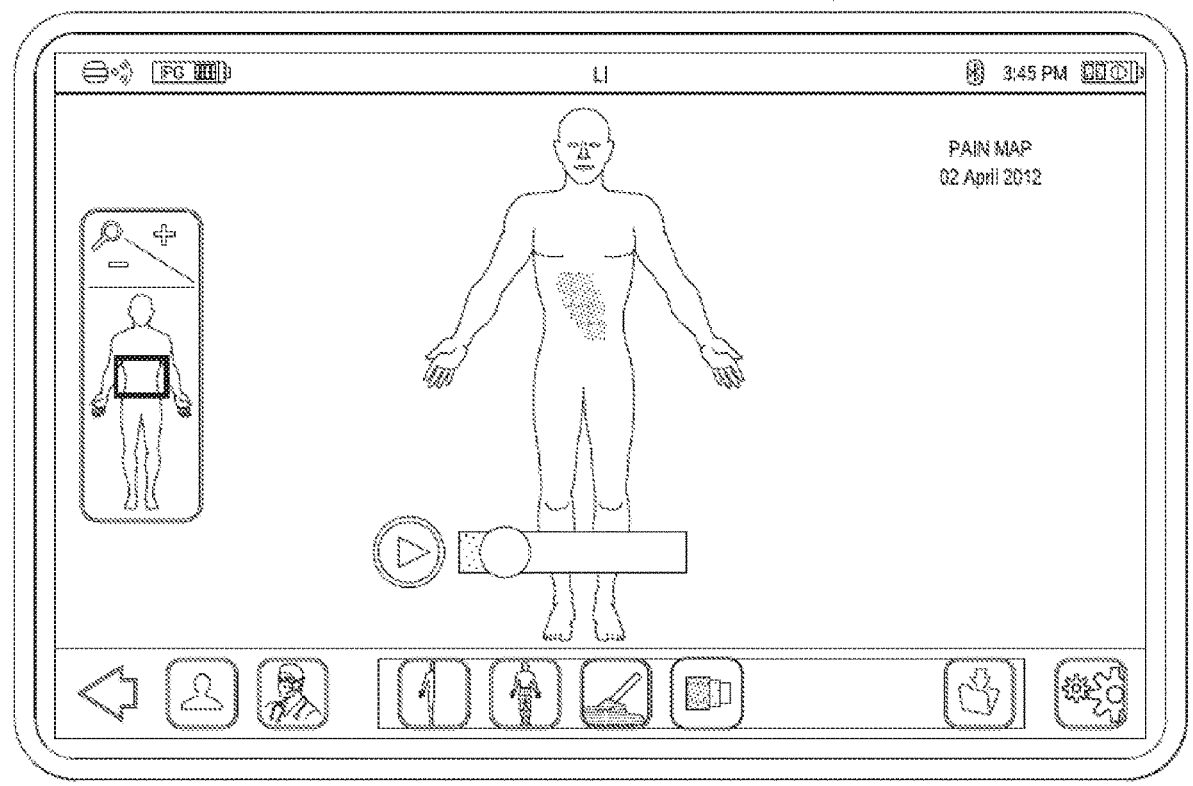

The database of pain/stimulation maps allows for a visualization of a migration history of pain maps or stimulation maps over time. For example, referring to FIGS. 16-17, the user interface 100 may display a slider control mechanism to visually indicate a pain map at a plurality of time slots. In the illustrated embodiment, the slider control mechanism has a slider that can be moved toward the left of the screen or toward the right of the screen. The position of the slider corresponds to the pain map at a particular point in time. As the slider is moved from the left to the right, more and more recent pain maps are retrieved from the database and displayed by the user interface 100. For example, the pain map shown in FIG. 16 is taken on Apr. 2, 2012, whereas the pain map shown in FIG. 17 is take on May 2, 2013. A plurality of other pain maps may exist between Apr. 2, 2012 and May 2, 2013, but they are not specifically illustrated herein for reasons of simplicity. It is understood, however, that as the user drags the slider from the left to the right, the user interface 100 is continuously updated with more and more recent pain maps that are visually displayed. Similarly, if the user drags the slider from the right to the left, the user interface 100 would be continuously updated with older pain maps from the past. Note that the user may also simply click on the play button next to the slider control mechanism, which will automatically play the migration history of the pain map over time.

Therefore, the user can easily see and understand the migration history of the pain maps, which represent the change of the pain experienced by the patient over time. The visualization of the pain map migration history is intuitive for the user and allows him/her to formulate a more effective treatment plan accordingly. It is understood that although pain maps are used here to visually illustrate a type of migration history, stimulation map migration history may also be implemented in a similar manner. In other words, the slider control mechanism may also be used to visually illustrate a migration history of the stimulation maps over time, thereby further facilitating the diagnosis and treatment of the patient's pain.

Note that the slider control mechanism is used herein simply as one example for controlling the visualization of the migration history of pain/stimulation maps. In alternative embodiments, other suitable types of control mechanisms may be used, for example fast-forward or rewind buttons/arrows, or virtual toggles, switches, or dials may each be used to "navigate" through time. In some embodiments, the user may also manually enter a particular point in time and retrieve the pain/stimulation map to correspond with that time manually.

Obtaining 2D Representation of 3D Pain/Stimulation Maps

The discussions above describe how a pain map or a stimulation map can be generated on a 3D human body model. Thus, the pain/stimulation map discussed above may be referred to as 3D pain/stimulation maps. The 3D pain/stimulation maps allows a patient to accurately portray the pain and stimulation experienced by the patient, and they also allow the healthcare professional to better diagnose the pain and to develop a suitable treatment protocol for the patient.

However, there are times when it is desirable to obtain a 2D representation of the 3D pain/stimulation map. For instance, the 3D pain/stimulation maps are typically data-intensive (i.e., they may be large files), which make their sharing difficult. As a result, may take an excessively long period of time to upload a 3D pain map from a clinician programmer to a remote database, and/or to download that pain map from that database to a clinician programmer. In comparison, a 2D pain/stimulation map is typically much less data-intensive (e.g., with a percent of the data for a 3D pain/stimulation map) and as such can be easily shared. As another example, 3D pain/stimulation maps may not be easily printed. Thus, it may be desirable to print a 2D representation of the 3D pain/stimulation map. The following discussions describe how to obtain a 2D representation of a 3D pain/stimulation map according to the various aspects of the present disclosure.

At least two types of 2D pain/stimulation maps may be obtained from a 3D pain/stimulation map. One type of the 2D pain/stimulation map is derived as a "snapshot" (also referred to as a projection) of the 3D pain/stimulation map. The "snapshot" type 2D pain/stimulation map may be obtained by rotating the 3D pain/stimulation map to a suitable perspective or viewing angle, and then projecting the 3D pain/stimulation map to a flat surface. Thus, the "snapshot" 2D pain/stimulation map is a projection of the 3D human body model with the pain/stimulation map drawn on it. Alternatively stated, the "snapshot" 2D pain/stimulation map captures an instantaneous picture of the 3D pain/stimulation map, as seen by a person viewing the 3D pain/stimulation map at that time.

Another type of the 2D pain/stimulation map is derived as a "wrapping texture" or a "wrap cloth" of the 3D pain/stimulation map. This is done by showing an entire surface area of the 3D human body model (or a selected portion thereof) by flattening or completely stretching it out. The 3D pain/stimulation map on the body model is therefore flattened or stretched out too. Another way of looking at the generation of the "wrapping texture" type 2D pain/stimulation map is that, a two-dimensional flat digital "cloth" is wrapped around the 3D human body model. As such, the cloth takes after the shape and contours of the 3D human body model. The patient then paints the pain/stimulation map on this piece of digital "cloth." The resulting pain/stimulation map therefore exhibits 3D characteristics as long as the cloth itself is wrapped around the 3D human body model. To obtain the 2D pain/stimulation map, the digital cloth is removed from the 3D body model and flattened or stretched out. At this point, the digital cloth returns to a 2D form. Consequently, the painted pain/stimulation regions on the digital cloth now also flat and exhibits 2D characteristics.

It is understood that the digital cloth may be a single piece of cloth in some embodiments, but may also include multiple pieces of cloth in alternative embodiments.

It is understood that the 3D pain/stimulation map and the 2D pain/stimulation maps discussed above may contain reference points, which allow the 2D pain/stimulation map to match up correctly with the 3D pain/stimulation map. For example, in order to reconstruct a 3D pain/stimulation map from one or more 2D pain/stimulation maps, their respective reference points should match up.

Regardless of which type of 2D pain/stimulation map is obtained, the amount of data involved for the 2D pain/stimulation map is much less than its 3D counterpart. For example, the data required for the "snapshot" type 2D pain/stimulation map only needs to be sufficient to represent a single projection of the 3D map or model, rather than needing data to represent the map or model from all different perspectives and viewing angles. As another example, for the "wrapping texture" type 2D pain/stimulation map, only the digital cloth itself may be needed for the sharing thereof. The data associated with the actual 3D human body model is not needed. In other words, in order to share the 3D pain/stimulation map, only the 2D pain/stimulation map is needed, and then the 3D pain/stimulation map may be reconstructed after the receipt of the 2D pain/stimulation map.

For instance, a patient John Doe may generate a 3D pain/stimulation map based on a predefined human body model type (e.g., a 35-year old 6'0 Caucasian male weighing 200 pounds) as discussed above. A corresponding "wrapping texture" type 2D pain/stimulation map may then be obtained by flattening the digital "cloth." The 2D pain/stimulation map may be uploaded to and saved in a remote electronic database, for example in a manner consistent with the discussions above. The actual 3D human body model need not be sent, as that 3D human body model is already available in that electronic database (or can be readily downloaded from another suitable electronic database).

Suppose now that John Doe has moved to a different part of the country. He makes a visit with a new healthcare provider. The healthcare provider may have access to the remote electronic database that includes the 3D human body model corresponding to John Doe's physiology (as well as a plurality of other predefined human body types). These body types may already be downloaded onto the healthcare provider's clinician programmer (or can be readily downloaded). Therefore, to reconstruct the 3D pain/stimulation map for John Doe, the healthcare provider merely needs to access the electronic database where the 2D digital cloth having the pain/stimulation map drawn thereon is stored. The 2D digital cloth can be quickly downloaded onto the healthcare provider's clinician programmer, since it is a 2D object and therefore is not very data-intensive. The clinician programmer can then reconstruct the 3D pain/stimulation map by "wrapping" the digital cloth on the 3D human body model corresponding to John Doe's physiology. Note that in this reconstruction process, the actual human body model need not be transmitted by John Doe's previous healthcare provider. Again, only the 2D digital cloth having the pain/stimulation map needs to be shared. The new healthcare provider just needs to locate the correct 3D human body model from the database, download the 2D digital cloth, and wrap the cloth around the 3D human body model in order to reconstruct John Doe's 3D pain/stimulation map.

It is understood that, in addition to the wrapping texture 2D pain/stimulation map, the snapshot type 2D pain/stimulation map may also be used to reconstruct the 3D pain/ stimulation map. For example, a plurality of snapshot 2D pain/stimulation maps may be obtained from a 3D pain/stimulation map. Each of the snapshot 2D pain/stimulation maps may represent a different perspective or a different angle. Later on, these snapshot 2D pain/stimulation maps may be collectively used to piece together the original 3D pain/stimulation map.

FIGS. 18A-18B and 19-22 are example screenshots of a user interface 350 for viewing 3D and 2D pain/stimulations maps according to the various aspects of the present disclosure. In some embodiments, the user interface 350 may be displayed on a screen of a programmer, for example a capacitive or resistive touch-sensitive display.

Figure 18A:
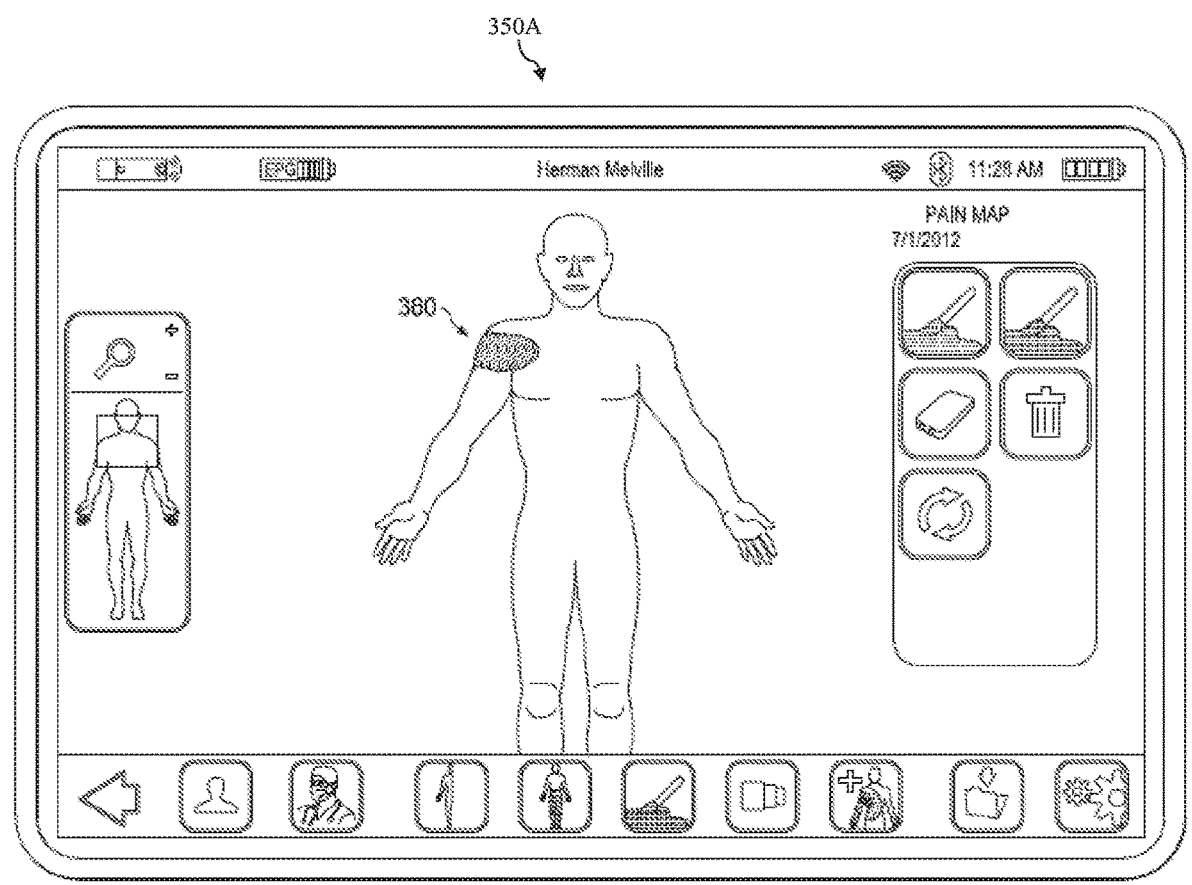
Figure 18B:
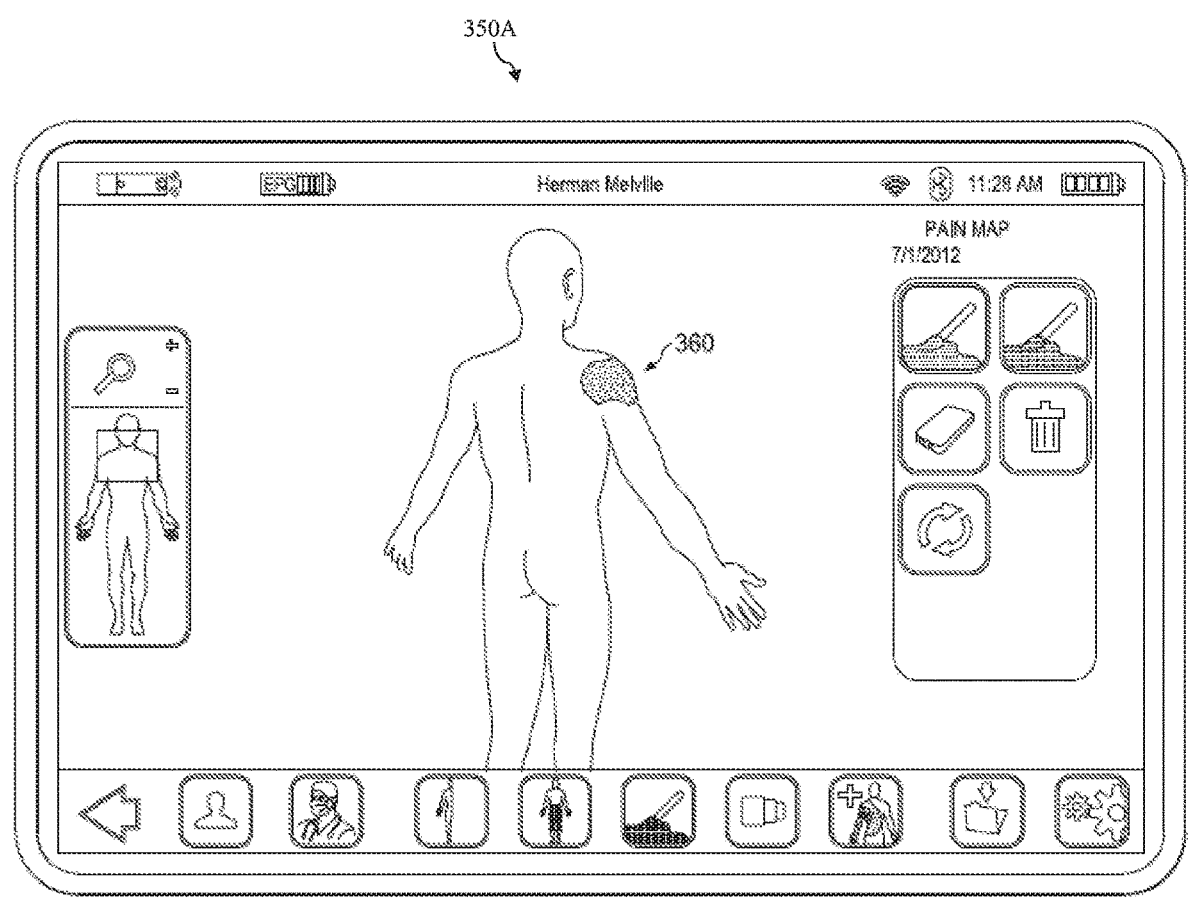

Referring to FIGS. 18A-18B, the user interface 350A illustrates an example 3D pain map 360 from two different perspective angles. In the illustrated embodiment, the pain map 360 is located in or near a right shoulder of the 3D human body model. After the 3D pain map 360 is completed, 2D representations of the 3D pain map may be generated, for example by clicking a virtual button (not illustrated herein) in the interface 350.

Figure 19:
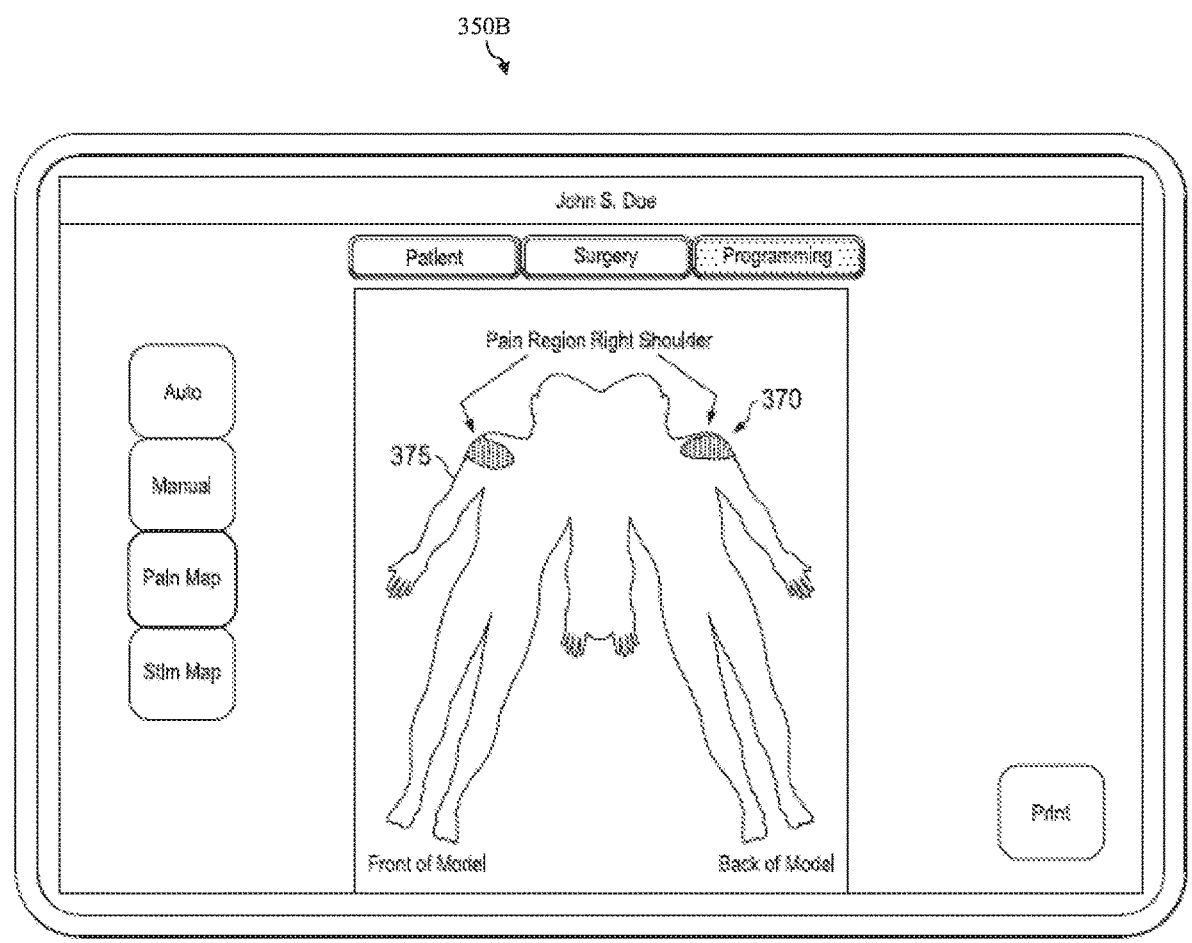

An example of the 2D pain map corresponding to the 3D pain map 360 is shown in FIG. 19. The user interface 350B shows a 2D pain map 370 that is a "flattened" version of the 3D pain map 360. In other words, the 2D pain map 370 is a wrapping texture type 2D pain map. A digital "cloth" 375 is used to wrap around the 3D human body model. The pain region is drawn on the digital cloth 375. Therefore, the 2D pain map 370 is obtained when the digital cloth 375 is flattened to its 2D form. In some embodiments, the digital cloth is flattened into the 2D form by splitting the 3D human body model along the vertices (defining the shape of the 3D model) on the side of the model.

The 2D pain map 370 of FIG. 19 contains substantially less data than the 3D pain map 360 of FIGS. 18A-18B. In some embodiments, the 2D pain map 370 has less than 10% of the data associated with the 3D pain map 360. Therefore, the 2D pain map 370 can be easily shared over a network or printed. To reconstruct the 3D pain map 360, an electronic programmer merely needs to download the 2D pain map 370 and apply it over the same 3D human model on which it was originally created. As discussed above, the particular 3D human body model may be selected from a list of predefined human body models from a database. These predefined human body models each have a set of unique physical characteristics, such as height, weight, age, gender, body build, or ethnicity.

Figure 20:
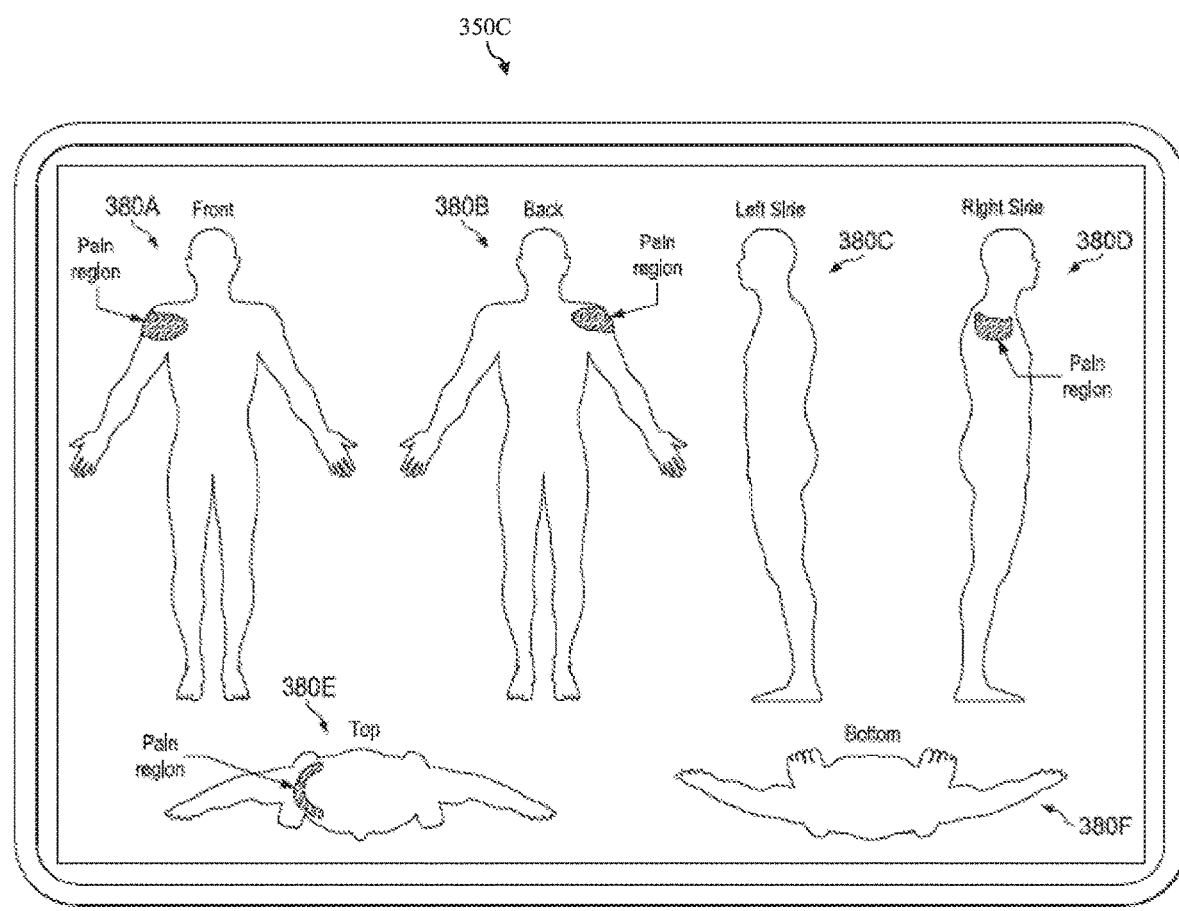

Another example of the 2D pain map corresponding to the 3D pain map 360 is shown in FIG. 20. The user interface 350C shows various 2D "snapshot" type pain maps 380A-380D of the 3D pain map 360 taken at different angles. The snapshot 2D pain map 380A is derived by projecting the front of the 3D pain map 360 to a flat surface, the snapshot 2D pain map 380B is derived by projecting the back of the 3D pain map 360 to a flat surface, the snapshot 2D pain map 380C is derived by projecting the left side of the 3D pain map 360 to a flat surface, and the snapshot 2D pain map 380D is derived by projecting the right side of the 3D pain map 360 to a flat surface. Again, these 2D pain maps 380A-380D contain substantially less data than the 3D pain map 360. Therefore, the printing and sharing of these 2D pain maps 380A-380D are much easier than the printing and sharing of the 3D pain maps. Of course, the discussions above also apply to 3D and 2D stimulation maps.

The present disclosure also allows for custom-zoomed printed regions. To illustrate, an example 3D pain map 390 is shown by the user interface 350D in FIG. 21. The pain region is on the left food and a lower left leg portion in the illustrated embodiment. Thus, for a more detailed view of the pain region, the user interface 350D zooms in to a portion of the lower left leg portion of the human body model. If additional detail is needed, the user interface 350D allows for further zooming. In addition, the user interface 350D allows for rotation repositioning of the part of the human body model showing the 3D pain map 390 as well.

Figure 21:
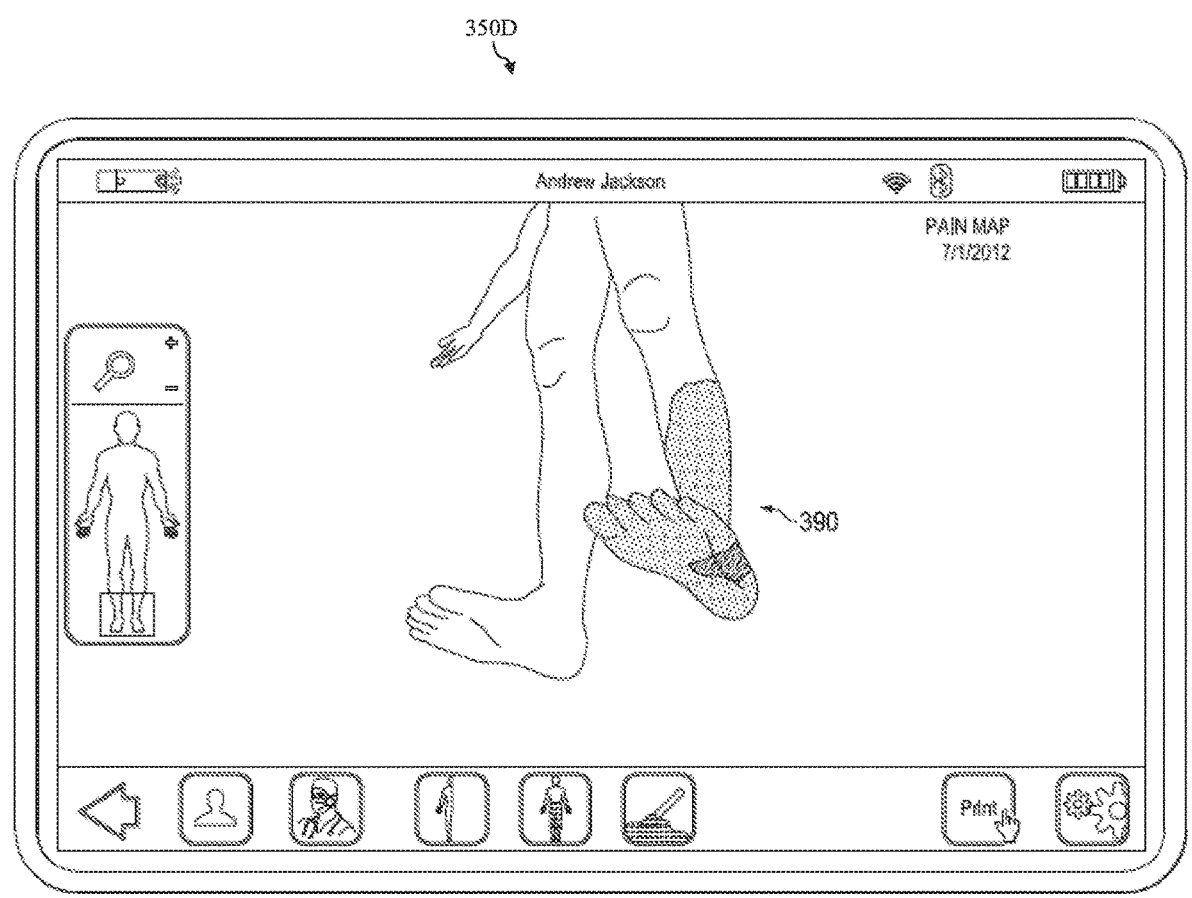
Figure 22:
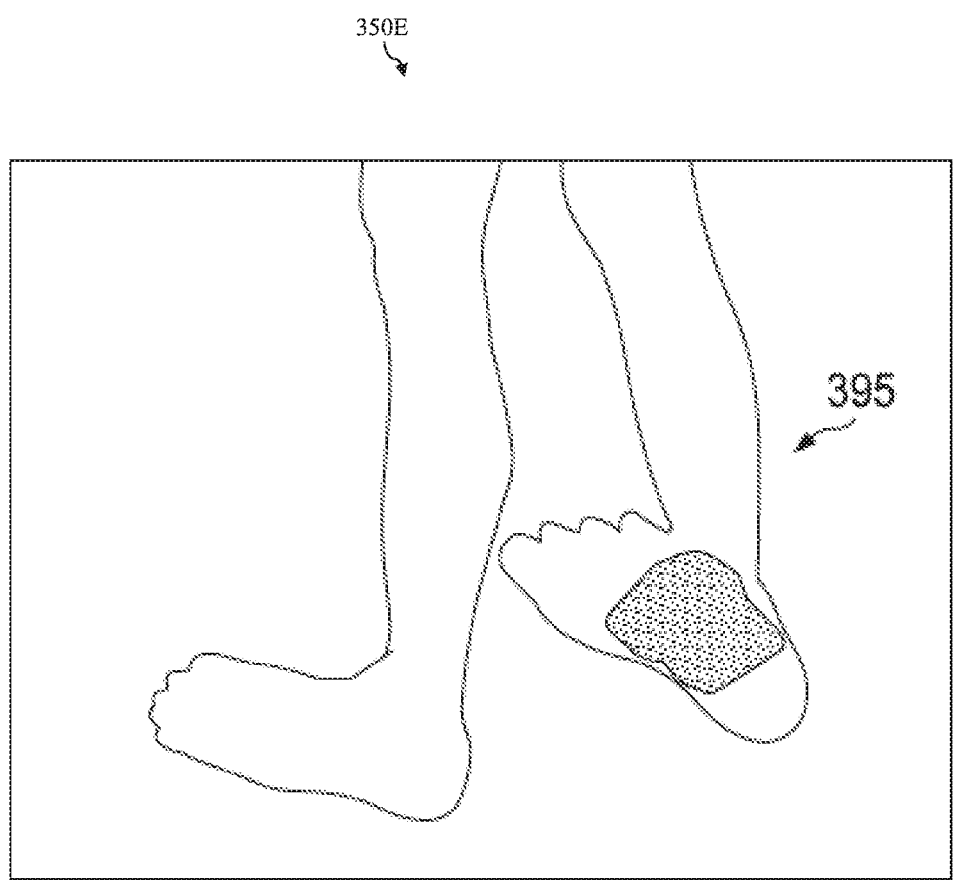

Referring now to FIG. 22, the user interface 350E shows a 2D pain map 395 that is derived from the 3D pain map 390 of FIG. 21. As was the case with the 3D pain map 390, the 2D pain map 395 also includes a "zoomed in" view near the left foot and lower leg of the human body model. As discussed above, this custom zoomed 2D pain map 395 is easier to print and share, which is at least in part due to its much smaller data size compared to its 3D counterpart.

Figure 23:
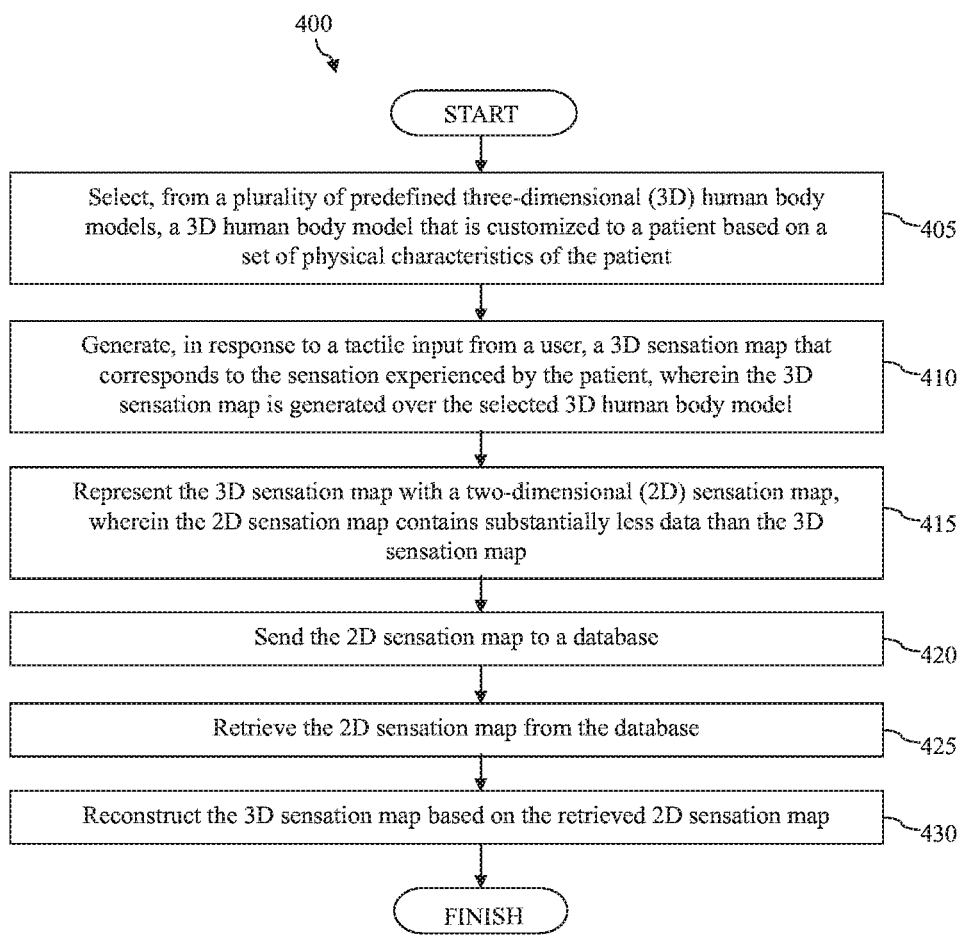
FIG. 23 is a flowchart illustrating example process flows for generating and displaying pain/stimulation maps according to various aspects of the present disclosure.

FIG. 23 is a flowchart illustrating an example process flow for graphically representing a sensation such as pain or stimulation experienced by a patient. The method 400 includes a step 405, in which a 3D human body is selected from a plurality of predefined three-dimensional (3D) human body models. The selected 3D human body model is customized to the patient based on a set of physical characteristics of the patient. In some other embodiments, the plurality of predefined 3D human body models is stored in the database. In some other embodiments, the plurality of predefined 3D human body models each have a unique set of physical characteristics including one or more of the following: height, weight, age, gender, and ethnicity. In some other embodiments, the selected 3D human body model has a closest physical characteristics match with the patient.

The method 400 includes a step 410, in which a 3D sensation map that corresponds to the sensation experienced by the patient is generated in response to a tactile input from a user. The 3D sensation map is generated over the selected 3D human body model. In some embodiments, the step 410 includes wrapping a digital cloth around the selected 3D human body model, wherein the digital cloth contains one or more sensation regions drawn by the user. The 3D sensation map includes at least one of: a 3D pain map that includes a 3D visualization of a pain experienced by the patient in a first body region of the patient; and a 3D stimulation map that includes a 3D visualization of a stimulation experienced by the patient in a second body region of the patient. In some embodiments, the user is the patient. In other embodiments, the user may be a healthcare professional.

The method 400 includes a step 415, in which the 3D sensation map is represented with a two-dimensional (2D) sensation map. The 2D sensation map contains substantially less data than the 3D sensation map. For example, in some embodiments, the 2D sensation map contains less than 10% of the data associated with the 3D sensation map. In some embodiments, the step 415 includes taking the digital cloth off of the selected 3D human body model and flattening the digital cloth to a 2D form. In some other embodiments, the step 415 includes projecting the 3D sensation map onto a flat surface.

The method 400 includes a step 420, in which the 2D sensation map is sent to a database.

The method 400 includes a step 425, in which the 2D sensation map is retrieved from the database.

The method 400 includes a step 430, in which the 3D sensation map is reconstructed based on the retried 2D sensation map. In some embodiments, the step 430 is performed using the selected 3D human body model.

In some embodiments, the steps 405-420 are performed by a first portable electronic device, and the steps 425-430 are performed by a second portable electronic device. The first and second portable electronic devices may each include one of: a clinician programmer, a patient programmer, and a computer tablet, and wherein the first and second electronic devices are configured to communicate with external devices according to a wired or wireless communications protocol.

Individually Rotatable Implantable Items in a Spinnable Virtual Carousel

Figure 24:
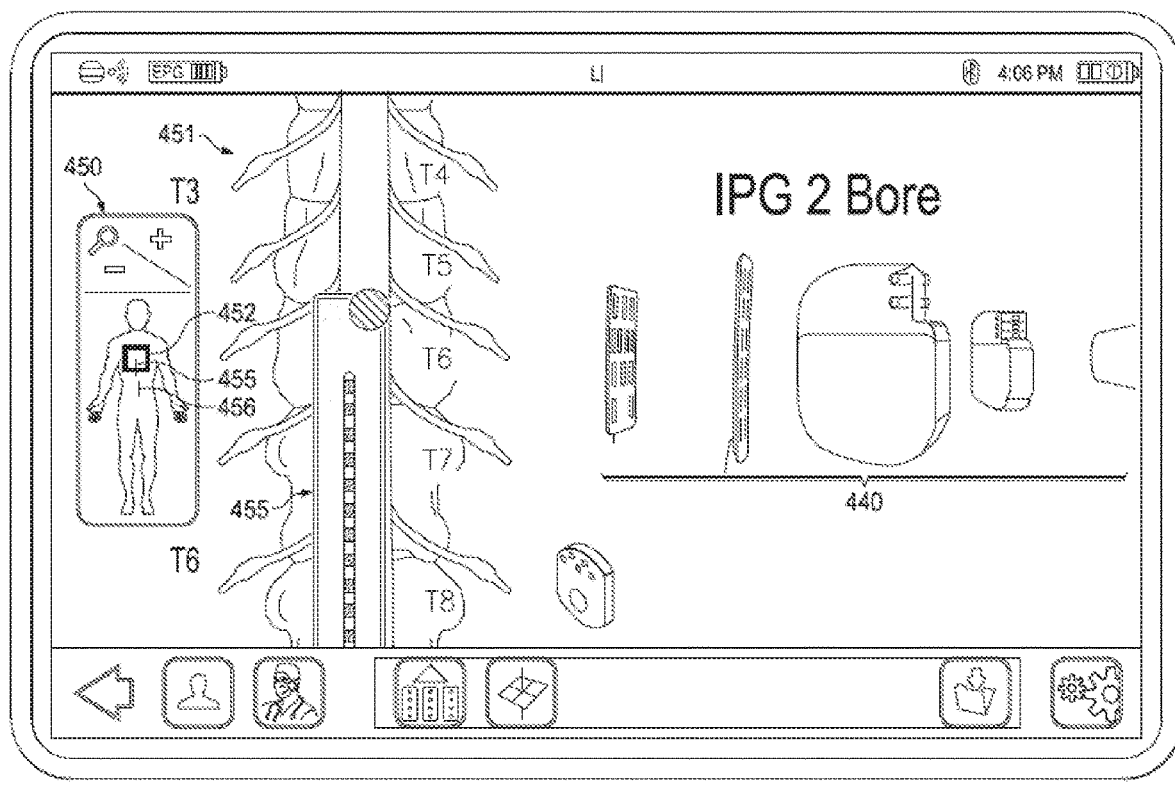

Referring now to FIG. 24, the user interface 100 of the clinician programmer includes a spinnable digital carousel 440 that shows the virtual reality representations of a plurality of medical devices. The virtual reality representation of each medical device may include an accurate movable and individually rotatable 3-D model of the medical device. The medical devices may be of different types, for example different types of leads, paddles, and pulse generators (including both implantable pulse generators (IPG) and external pulse generators (EPG).) These different types of medical devices are arranged in the carousel 440, which is spinnable. As the user spins the carousel 440, for example by moving his finger to the left or right on the touch screen, the models of different medical devices may be brought to the front of the carousel 440. The medical device at the front of the carousel 140 may be considered an active selection of the user (i.e., the device is activated). As the digital carousel 440 is being spun, each implantable medical device is also individually rotated, for example rotated with respect to its central axis. Stated different, as the digital carousel 440 is being spun, the various implantable medical devices making up the digital carousel 440 are also individually rotated, thereby giving the user different perspectives or viewing angles of these medical devices. By doing so, the digital carousel allows a more intuitive and detailed view of each implantable medical device. Once a medical device is selected/activated through the carousel 440, it can be dragged outside of the carousel 440 for further customization and manipulation. Additional descriptions of the digital carousel and virtual reality representations of medical devices in general are found in U.S. patent application Ser. No. 13/601,449, filed on Aug. 31, 2012, entitled "Virtual Reality Representation of Medical Devices" to Kaula et al., the disclosure of which is hereby incorporated by reference in its entirety.

Lead Representation on a Crude Human Body Model

The user interface 100 on the clinician programmer also includes a crude human body model 450 situated adjacent to an anatomical environment 451 of the human body model. The crude human body model 450 includes a navigation box 452. The user can quickly access a particular location of the human body model by moving the box 452 to that location. As the box 452 is being moved, the anatomical environment 451 of the human body model (e.g., a spine herein) is updated to reflect the change. The user interface 100 also offers a zoom feature (e.g., "+" and "−" signs) that within the crude human body model 450 that can be used to show a closer view (by zooming in) or a farther view (by zooming out) of the human body model. In other words, when the zoom feature is activated to zoom in the human body, a more detailed view (e.g., showing fewer vertebrae) of the anatomical environment 451 is shown. Conversely, when the zoom feature is activated to zoom out of the human body, a less detailed view (e.g., showing more vertebrae) of the anatomical environment 451 is shown.

In the embodiment illustrated in FIG. 24, one or more leads are selected as implantable medical devices and are thereafter positioned in the anatomical environment 451. One of such leads is illustrated as lead 455, which is placed near regions T5-T8 of the spine. The crude human body model 450 offers a simplified visual representation of the lead 455, which is shown as a line segment positioned inside the navigation box 452, since the navigation box 452 corresponds to the portion of the anatomical environment 451 visible on the screen to the user. Note that another lead 456 is also illustrated in the crude human body model 450, but it is located outside the navigation box 455. This indicates to the user that another lead is already placed in a part of the anatomical environment 451 not shown on the current screen. In other words, the other lead 456 is placed near a lower portion of the spine not visible in what is shown in FIG. 24. Thus, the lead representation in the crude human body model 450 is intuitive for the user, since it serves as a reminder to the user that additional leads are already placed.

Lead Fragmentation

Figure 25:
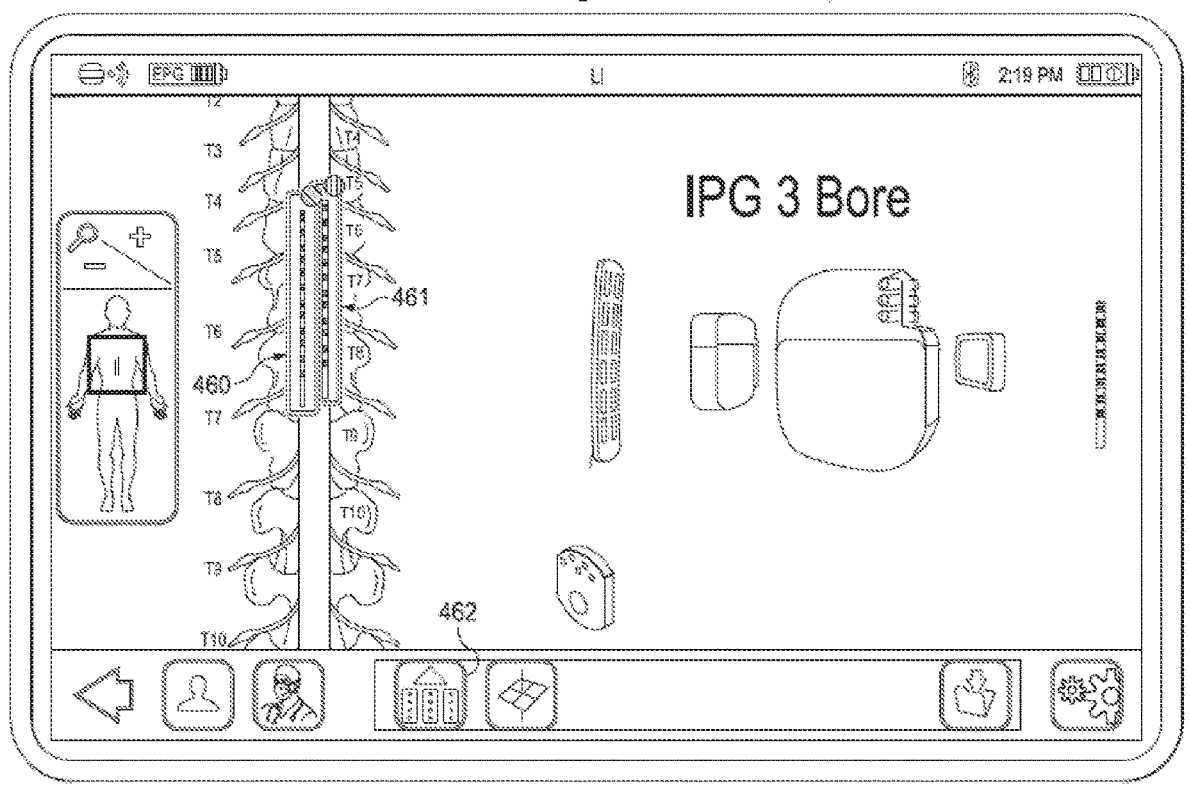
Figure 26:
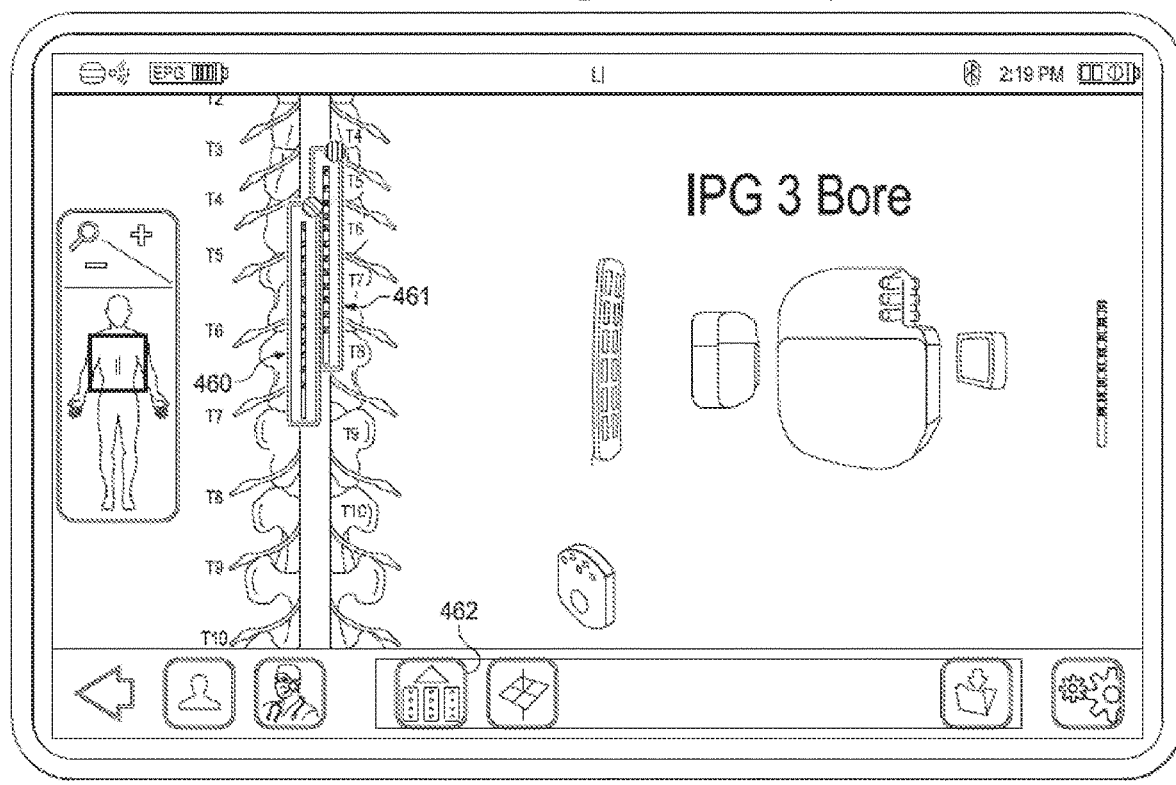

Sometimes multiple leads are positioned too close to each other, which makes them hard to be selected and handled individually. The present disclosure allows each lead fragmentation to quickly separate these closely-spaced leads. An example of lead fragmentation is shown in FIGS. 25-26. Referring to FIG. 25, two leads 460 and 461 are situated in close proximity to each other on a portion of the spine. As the present disclosure allows for a touch screen interface, the individual selection of either the lead 460 or the lead 461 may be somewhat inconvenient. That is, since these two leads 460 and 461 are situated in such close proximity, a selection of the lead 460 may also inadvertently select the lead 461, and vice versa.

To overcome this problem, the user may click on a virtual lead-fragmentation button 462 (or another suitable triggering mechanism), and the leads 460-461 in close proximity will automatically be spaced more apart, as shown in FIG. 26. In other words, the activation of the button 462 automatically increases the distance or spacing between adjacent leads in close proximity (for example leads within a predefined distance/spacing threshold of one another), thereby making each lead more individually-selectable without inadvertently selecting another non-target lead. As a result, user satisfaction is increased.

Automatic Lead Orientation Adjustment

Figure 27:
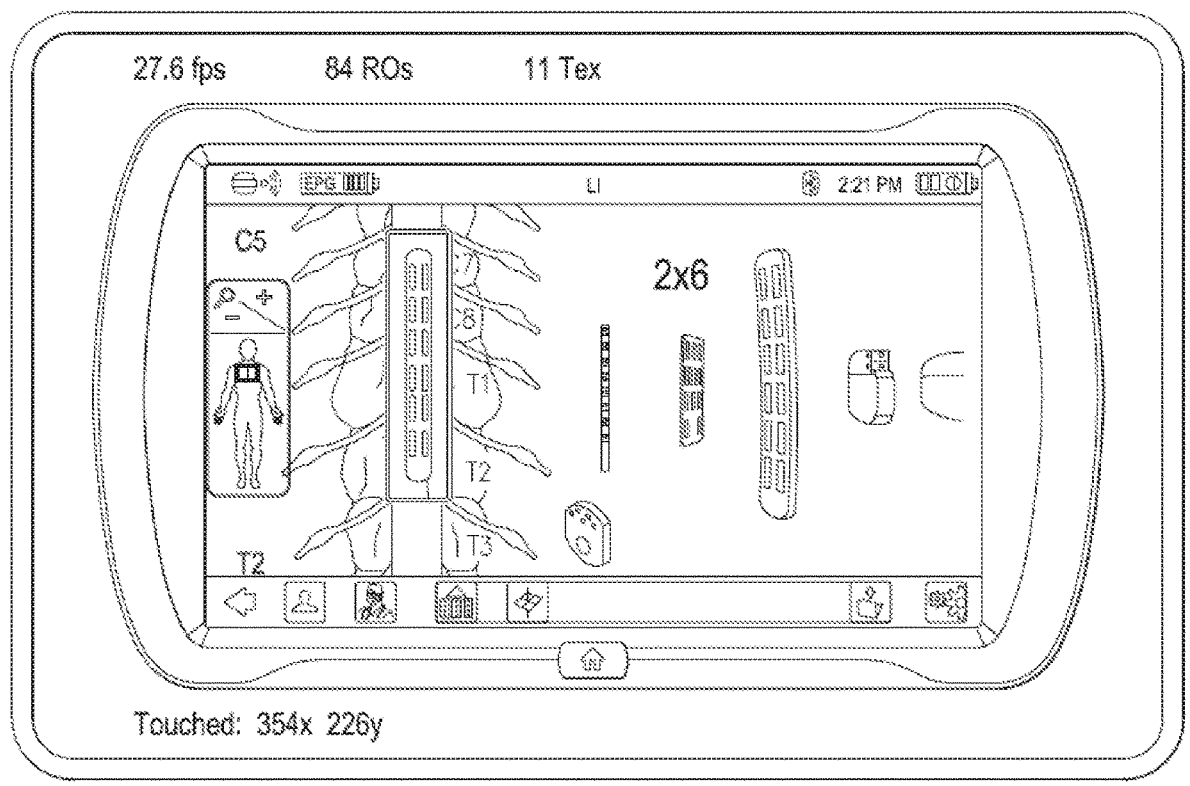
Figure 28:
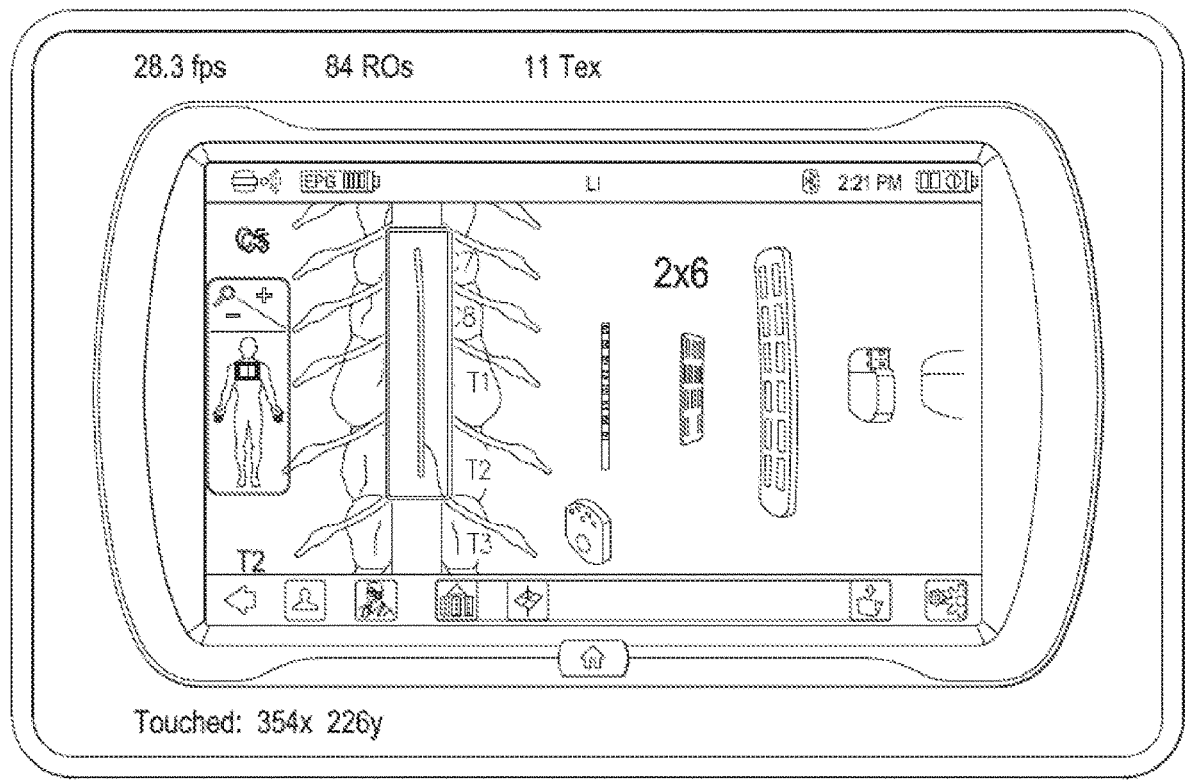

The virtual representation of implantable medical devices may be automatically rotated to imitate its realistic orientation when it is implanted. In more detail, referring to FIG. 27, a 2×6 paddle lead (a lead having 12 electrodes arranged in 2 columns and 6 rows) is selected from the virtual carousel and moved to a desired target implant location on the spine. Initially, as shown in FIG. 27, the electrodes of the lead are facing the user. This offers the user a visual illustration of the type of lead that is being implanted. Next, in FIG. 28, the lead will automatically rotate itself such that the electrodes are facing the spine, rather than the user. This is indicative of the lead's true implanted position and orientation with respect to the spine. In some embodiments, the lead may also be rotated upside-down (from its initial position in the virtual carousel) in order to accurately reflect the orientation and disposition of the electrodes. The automatic adjustment of the lead's orientation and/or position as discussed above helps prevent user confusion or misunderstanding as to the true orientation and/or disposition of an implanted lead.

II. Available Programming Options and User Interface Features

Easy Navigation Using a Home Button

The present disclosure offers support for multiple users to access and interact with the clinician programmer. This may present certain challenges with respect to navigation through the various parts of the user interface. For example, different users may need to be logged on and off (or in and out), which may occur while the user is not necessarily at a "login screen" designed for logging on and off. Traditional clinician programmers support only one user (i.e., whoever turns on the programmer), and therefore there is no need for that user to log on and off, since he/she is the sole user of the clinician programmer. In comparison, the clinician programmer discussed herein may support users A, B, and C, for example. For each user, regardless of where the user is in terms of navigating the user interface, he/she can quickly return to a home screen and subsequent log out through the use of a "home button".

Figure 29:
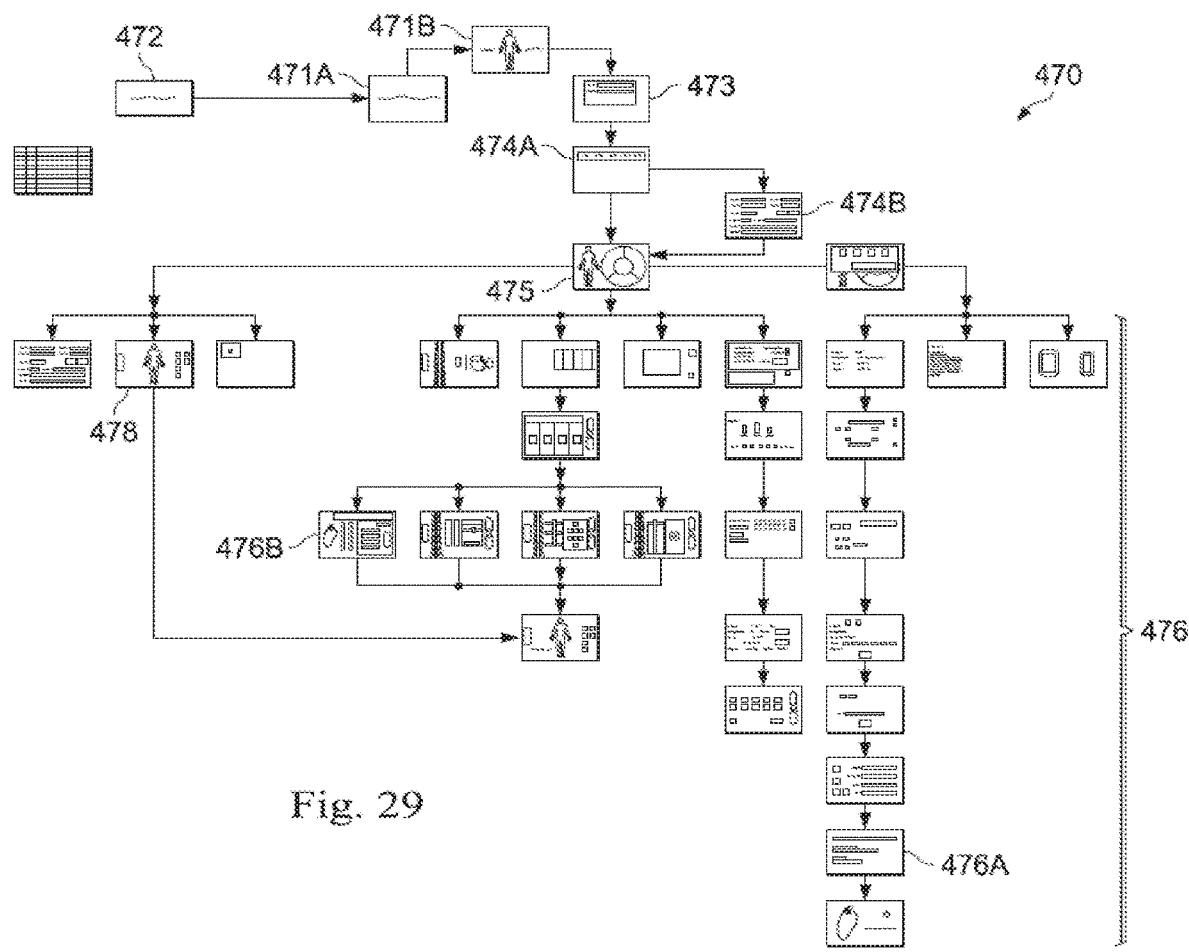
Figure 30:
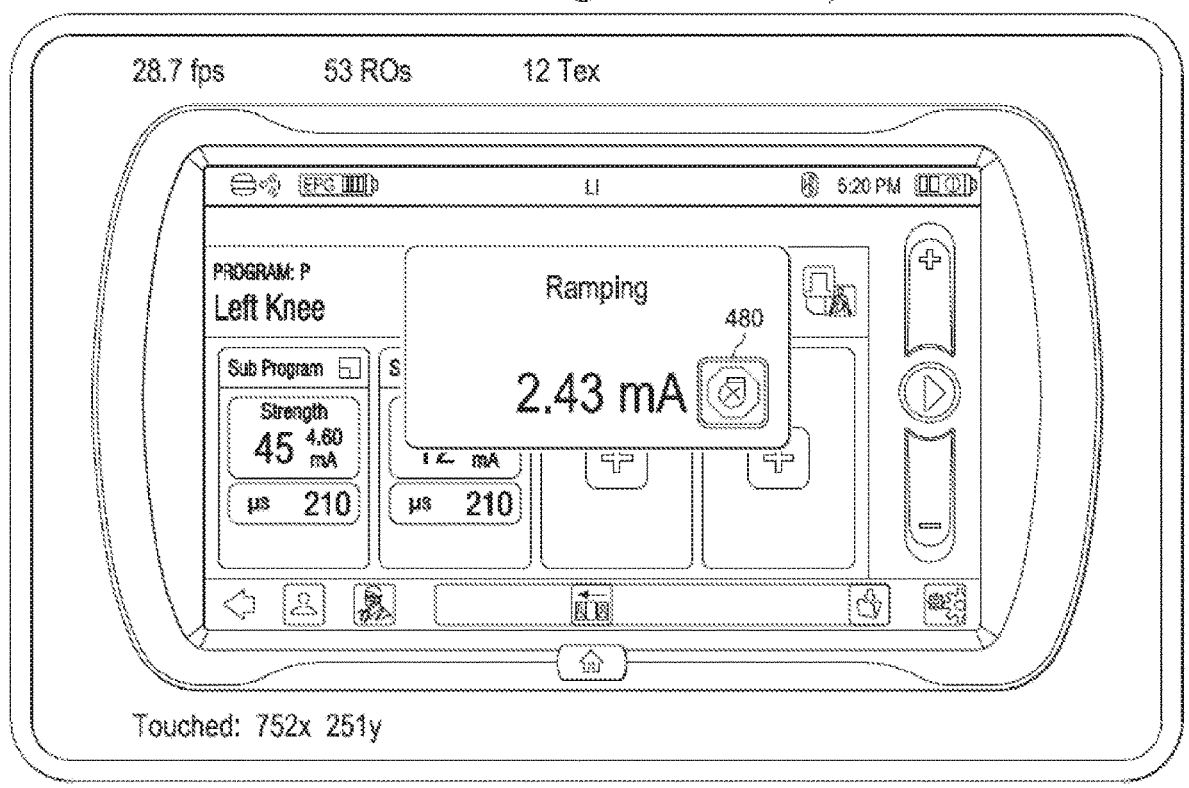

FIG. 29 illustrates an example user interface hierarchy 470, which is arranged in a tree-like format. One or more welcome screens 471A-471B sit at the top of the hierarchy 470. The welcome screens 471A-471B are the portions of the user interface 100 that greet the user as the user turns on (at step 472) the clinician programmer. Following the welcome screens 471A-471B is the login screen 473, where users A, B, or C can log on with the entry of a correct combination of username and password. Once the user logs on, he/she may create or edit information for a patient. For example, the user may create a new patient in a screen 474A, and then subsequently edit the information for that user in a screen 474B. The user may also select existing users for programming at the screen 474A. Once a patient is selected, the user is taken to a home screen 475. The home screen 475 offers a plurality of programming options and settings for the user, through which the user can formulate detailed treatment plans and analyses for the target patient and/or obtain treatment reports for the patient. These programming options and settings are illustrated with the plurality of screens 476.

For any given user, suppose he is at a particular screen 476A of the user interface, and he wishes to quickly return to the home screen 475. He can press a home button to do so. The same is true is the user is at a different screen 476B of the user interface. In some embodiments, the home button may be implemented as a "soft" button 478 that appears on every screen of the user interface. In other embodiments, the home button may be implemented as a hard or physical button located on the clinician programmer itself. In any case, a click of the home button takes the user back to the home screen 475 regardless of where the user currently is at the user interface hierarchy. In addition, the home button can assist the user to quickly return to the logon screen 473. If the user is currently at the home screen 475, another click of the home button will take the user back to the logon screen 473, where the user can log himself out. However, if the user is at one of the screens 476 (e.g., screen 476A or 476B), two clicks of the home button can take the user to the logon screen 473 (i.e., one click of the home button takes the user back to the home screen 475, and a second click of the home button takes the user back to the logon screen 473).

In comparison, traditional clinician programmers do not offer the logon screen 473 or the home screen 475, since any user can gain access to the entire programmer once it is turned on.

The present disclosure also offers different levels of users. For example, a group of users may be classified as super users, another group of users may be classified as administrative users, and yet another group of users may be classified as normal users. The role of super users is strictly to reset passwords of the two other groups: the administrative users and normal users. The provider/manufacturer may generate the passwords of all super users. Each clinician programmer manufactured will be assigned a unique super user password, and the password is disclosed to the owner of the clinician programmer. Users logged into the clinician programmer using this account may not change the super user password. In the case that the owner of the clinician programmer loses the password, the owner may request the original password from the manufacturer. In the event that multiple unsuccessful login attempts were made under the super user account, the clinician programmer should seed and generate a new password in a deterministic method defined by the manufacturer. Also in this case, the owner of the clinician programmer may request the newly generated password from the manufacturer.

The role of the administrative user (administrator) is to create edit and remove normal users, reset passwords for normal users, and assign privileges to normal users. In addition, a user logged in as an administrator has access to all areas of the clinician programmer. The clinician programmer defines four major areas that are to be protected by privileges:

Clinician programmer settings
Patient Record
Database (internal and/or external)
Pulse Generator & Stimulation Control Certain areas of the clinician programmer settings include backlight timer, power-save timer, screen brightness, sound volume, time and date setting, Wi-Fi connection, Bluetooth connection, default stimulation frequency, default minimum stimulation amplitude, default maximum stimulation amplitude, and default stimulation pulse width. The administrator user may choose to grant or restrict access to the clinician programmer settings area to a specific normal user. The advantage of privilege assignment is that normal users that should not adjust default stimulation parameters are prohibited from making changes in this section. The administrator is thus given the flexibility to assign which users have access to this area. Patient records are a critical and confidential part of the clinician programmer. These may contain patient's demographic data, patient treatment information, patient's physician information, patient's stimulation and pain mapping data and patients implants information. Adding, editing and/or removing patient record should be delegated to users that are familiar with patient treatment.

Activities performed within the clinician programmer are stored within the database that resides in the clinician programmer. In this method, the database maybe exported to a central database whereby multiple clinician programmers may share activities amongst each other. For example, if a certain health care professional treated a certain patient in a prior session and is absent during the current session, without sharing of the activities on a clinician programmer, it is impossible to understand the treatment record of the patient. In this case, multiple clinician programmers maybe synchronized by utilizing a centralized database. However, a scenario may arise whereby certain health care professionals should not have access to this sharing of information. Granting or restricting database editing and/or sharing provides a means to make the said scenario feasible.

The clinician programmer provides a means to control parameters being passed to the pulse generator as well as stimulation control. In a health care providing setting, there may be a scenario where an administrator may wish to restrict access to a clinician programmer user from manipulating pulse generator information. This may include restriction from being able to connect to an external pulse generator. Furthermore, there may be a case whereby certain users should not be allowed to turn on stimulation to a patient. The clinician programmer will allow stopping of clinician to any user as a safety measure.

In addition to assigning privileges to normal users, the administrator may also gain access to areas that are hidden from all other users. The clinician programmer implements algorithms that are customized to the needs of researchers and physicians. As normal users must not access these specialized areas, the clinician programmer provides a means to restrict access to these areas.

The role of a normal user is simply to gain access to the clinician programmer. It also gives access to areas that the user is privileged to access. In its simplest form, it guarantees usage of the clinician programmer only to authorized users. Furthermore, according to the privileges set by the administrator user, the normal user may gain access to these areas for patient data entry or treatment.

Again, the home button of the present disclosure can assist any of these types of users discussed above in quickly navigating through the user interface, for example to quickly return to the home screen 475 or quickly return to the logon screen 473.

Quick Stimulation Off with Ramping

As a safety control feature, the present disclosure offers a way for the user or patient to quickly turn off stimulation during ramping. In more detail, referring now to FIG. 30, the clinician programmer disclosed herein prompts the user to set a stimulation target current for the implanted medical device (e.g., implantable pulse generator). Rather than outputting that target stimulation current right away, the clinician programmer ramps up to the target stimulation current in a plurality of small steps, for example in 50 to 100 steps. In some embodiments, as the user presses a play button, the stimulation current is steadily ramped up to the target current. As the stimulation current is being ramped up, the patient may experience discomfort before the target stimulation current is reached. When this occurs, the clinician programmer may be used to stop the stimulation current ramping up process immediately. The cutting off of the stimulation may be done by the user (under the patient's response) pressing a stimulation off button, which can be a soft button 480 in the user interface or a hard physical button implemented on the clinician programmer itself. The cutting off of the stimulation may also be done by the patient using a patient device, for example a patient feedback device or a patient programmer.

Deactivation of Slider when Stimulation is on

Figure 31:
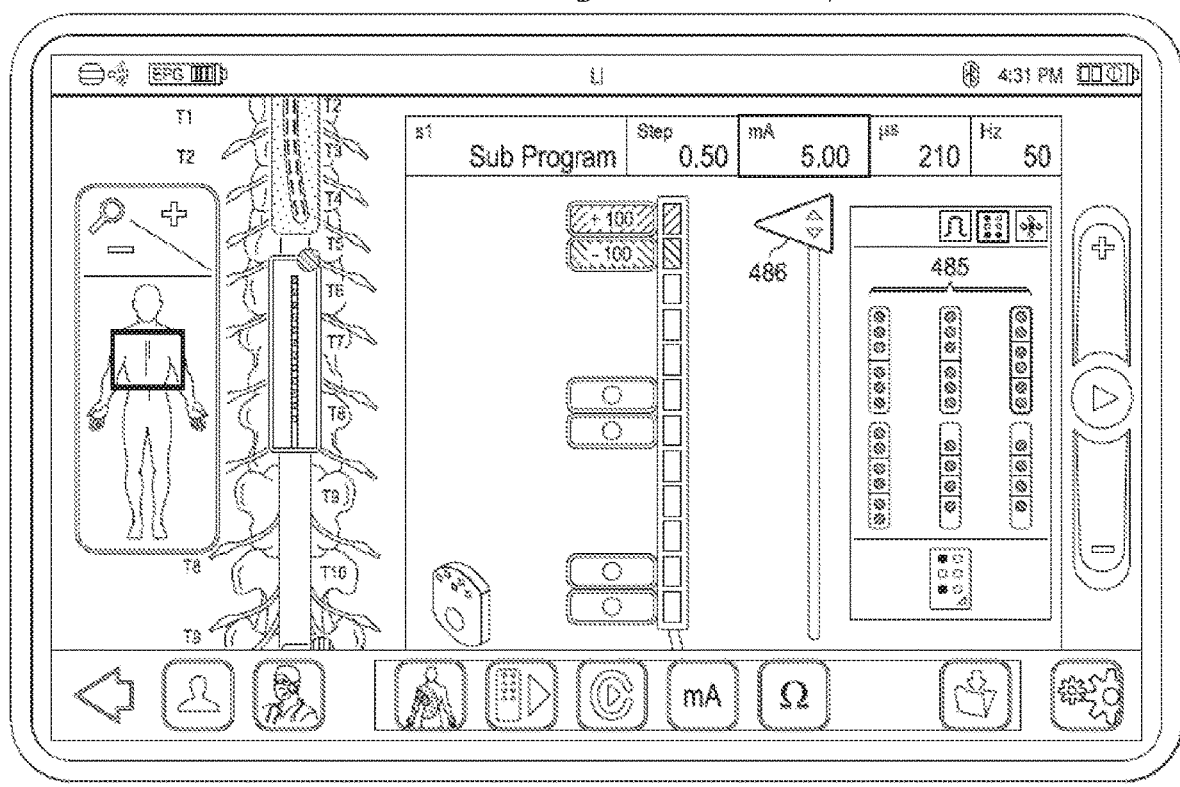
Figure 32A:
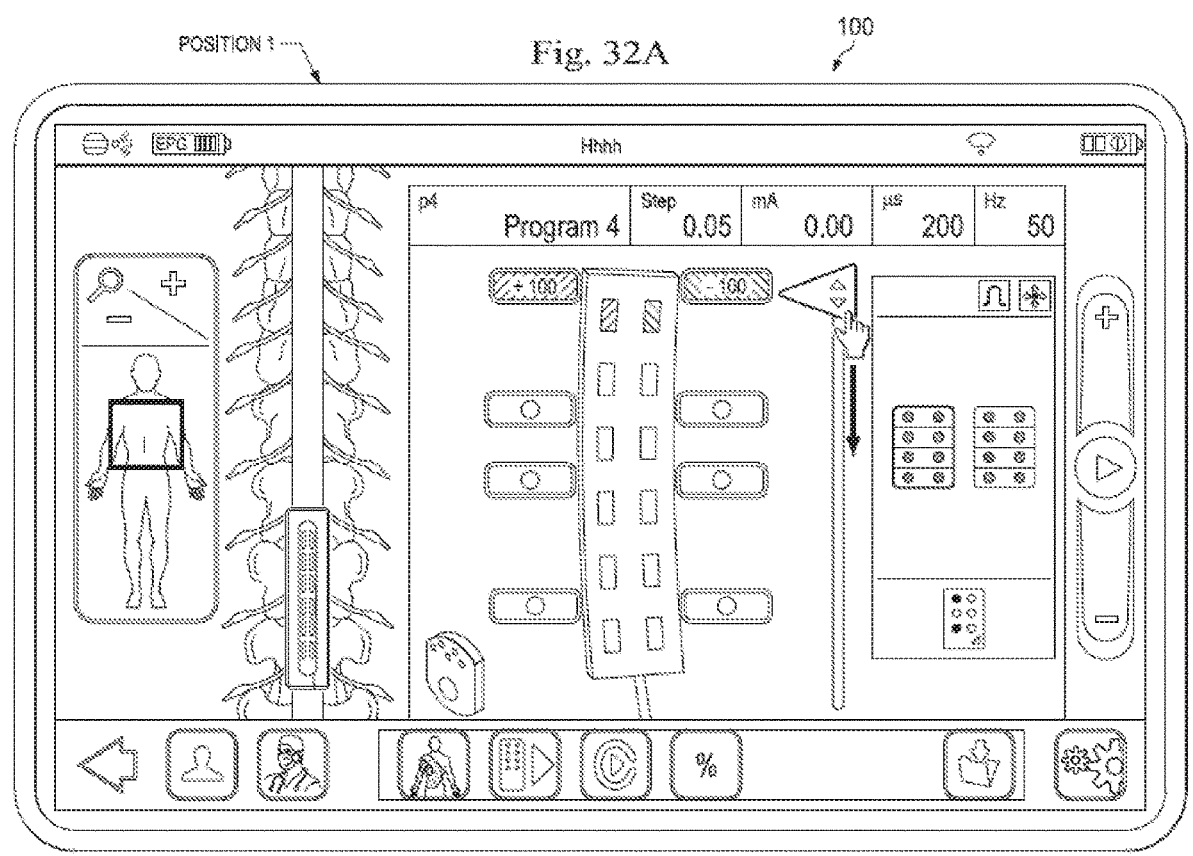
Figure 32B:
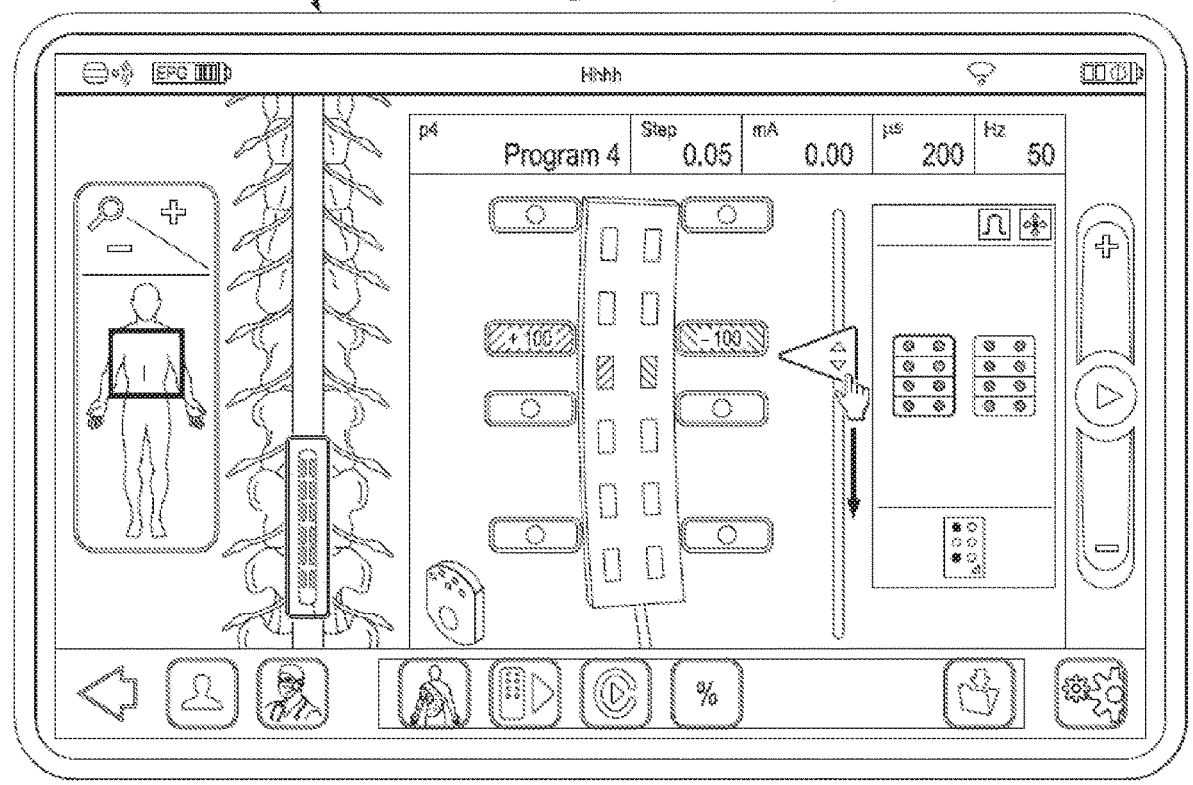

As another safety control feature, the present disclosure hides a slider (used for navigating the electrodes on a lead) when stimulation is on. In more detail, referring now to FIG. 31, the user interface 100 offers a menu of preset patterns 485 for electrodes. These preset patterns 485 are preprogrammed templates for electrodes, or pre-defined electrode configurations. A healthcare professional can choose between manual programming or the preset patterns 485. As shown in FIG. 31, a selected preset pattern is displayed on the lead representation in the center of the screen. The healthcare professional may change between positions on the lead using a slider 486 located between the lead representation and the pattern options menu. In other words, as the slider 486 is slide down, different electrodes on the lead become highlighted for programming. An example of using the slider, referring to FIG. 32, which shows positions 1, 2, 3, and 4. The slider is at a different position for each of the four illustrated positions, and each position corresponds to a different set of electrodes being highlighted for programming.

Figure 33:
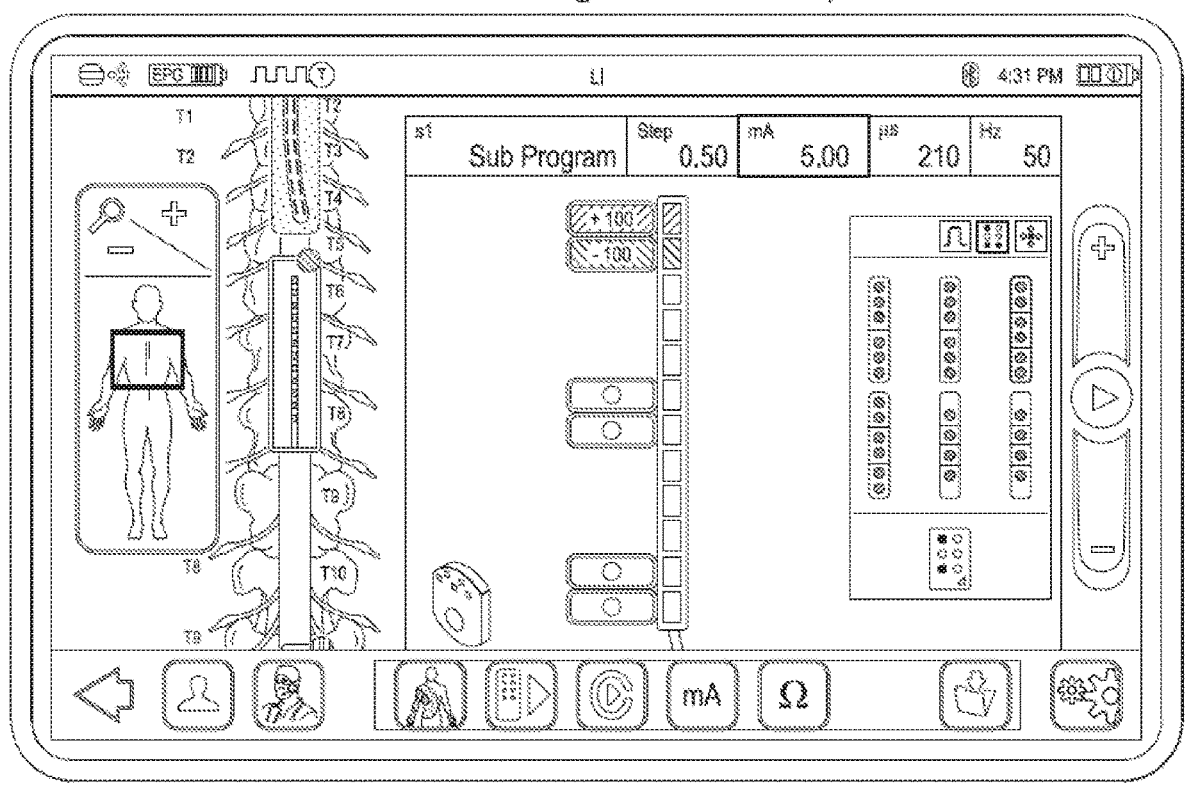

However, if the stimulation is on while the slider is being used to change electrode positions, the patient may feel discomfort or pain, particularly if different sets of electrodes are located relatively far away from one another, and thus moving down the slider will trigger electrodes to deliver pulses in regions of the body where no pain is felt and no stimulation is needed. Thus, as a safety control feature, the slider becomes hidden while stimulation is on, as shown in FIG. 33. It is only when stimulation is off (such as shown in FIG. 31) that the slider 486 will become visible again.

Dynamically Adjustable Charge Density Safety Limit Controls

As yet another safety control feature, the present disclosure allows the maximum stimulation amplitude to be automatically set (or automatically adjustable) depending on one or more factors such as the number of contacts, pulse width, or frequency. For example, with a first set of contacts and a first pulse width, the user interface of the clinician programmer automatically sets a maximum stimulation current that can be programmed by the user. In some embodiments, the user sets a stimulation current using a sliding mechanism. In these cases, the maximum stimulation current is set by preventing the user from moving the sliding mechanism beyond a certain threshold, i.e., the maximum current limit. In other words, the maximum current limit manifests itself similar to an invisible bar that prevents the current from moving beyond that point. Now, suppose the user changes to a second set of contacts (e.g., by deleting or adding one or more contacts). The maximum stimulation current is automatically adjusted correspondingly. As the user attempts to set the current using the sliding mechanism, the "invisible current limit" is at a different position on the sliding mechanism, thereby preventing the user from setting a current value greater than the limit. Similarly, if pulse width is changed by the user, the current limit may be automatically adjusted again. These automatic current limit adjustments reduce the likelihood of inadvertent pain or discomfort for the patient.

In some other cases, the changes in electrode contact configuration may violate the lead limits to the point where the automatic adjustment discussed above will no longer be feasible. In those situations, the user interface of the clinician programmer may not allow the user to make those changes to the electrode contact configuration and may display a warning message to the user, for example a message such as "Contact change would violate lead limits. Reduce program's amplitude or pulse limits or add contacts."

Visual Display of Battery Life and Longevity

Figure 34:
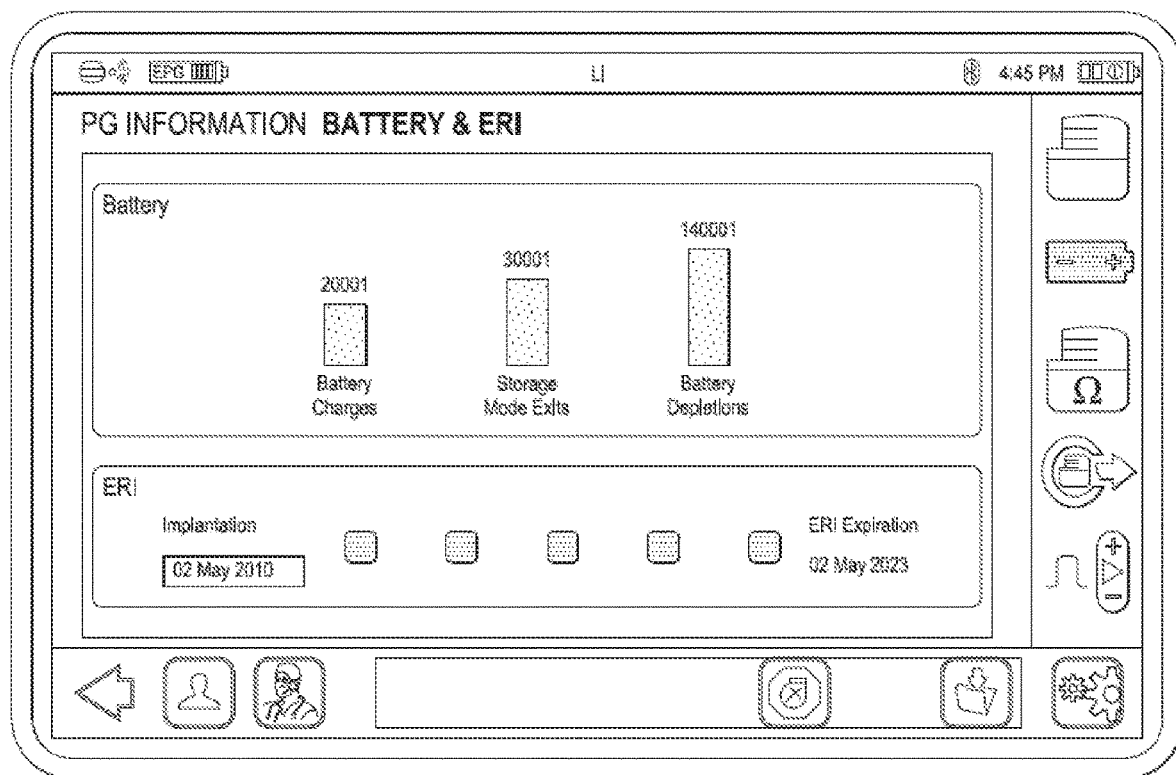

Referring now to FIG. 34, the user interface 100 of the clinician programmer may display a battery life and longevity in response to user request. The battery may refer to the battery of the implanted medical device, such as the pulse generator implanted in the patient. In the illustrated embodiment, the user interface 100 may inform the user of information such as the number of battery charges (e.g., 20001), the number of storage mode exits (e.g., 30001), or the number of battery depletions (e.g., 140001). Such information may help the user or any healthcare professional in evaluating and investigating the patient's battery problems. For example, if a patient comes in and complains that his battery life is getting too short, the user may determine from the battery life screen shown in FIG. 34 that the patient has let the battery die too many times (excessive number of battery depletions). Armed with this information, the user may recommend certain course of options to the patient. The battery life and longevity screen of the user interface 100 may also display information regarding the estimated battery life. For example, the implantation date may be May 2, 2013, and the estimated battery expiration date may be May 2, 2013. The bars located between these dates may be color-coded to indicate the health of the battery status too, as different colors may indicate different grades of battery health.

Automatic Current Balancing with Lock Control

As one of the many advanced features of the user interface 100, the clinician programmer of the present disclosure allows for automatic current balancing and lock control. In other words, the amount of current through a set of cathodes (or a set of anodes) will be automatically distributed, after one or more of the cathodes (or anodes) is "locked" into having a fixed percentage of the total cathodic current or anodic current. This is explained in more detail in FIGS. 35-38.

Figure 35:
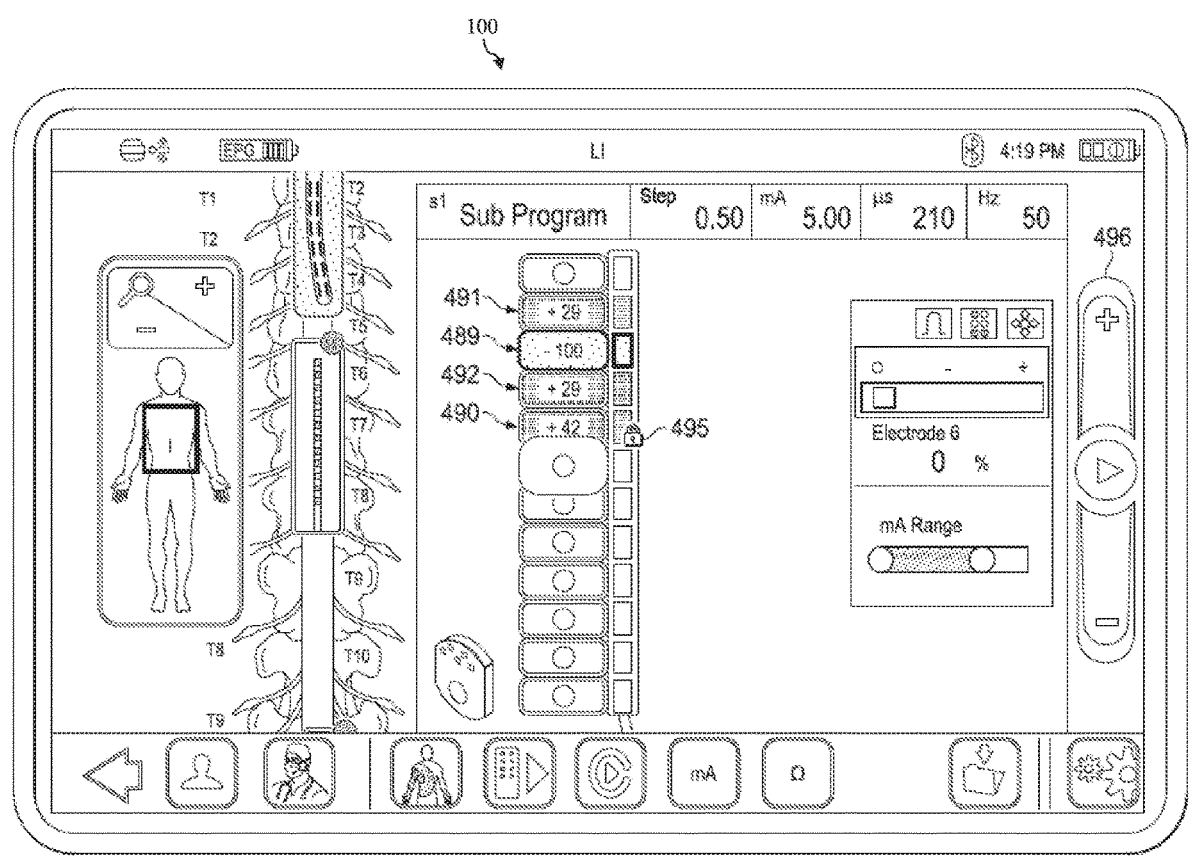

Referring to FIG. 35, suppose the user has programmed one cathode 489 and three anodes 490-492. The total amount of cathodic current is therefore distributed 100% through the lone cathode 489. The total amount of anodic current (equal to the amount of cathodic current) will have to be distributed through the three anodes 490-492, however. Typically, the total anodic current will be split substantially evenly between the three anodes 490-492. Therefore, the percentage of anodic current through the anodes 490-492 will be 33%, 33%, and 34% (no decimals in this embodiment). In other words, the total anodic current is automatically distributed substantially equally among all of the anodes 490-492. In the illustrated embodiment, the difference between the percentages of total stimulation current (be it the anodic current or the cathodic current) assigned to each electrode (whether it is for anodes or cathodes) is less or equal to 1% of the total stimulation current. In other embodiments, the difference may be less than 1%, for example 0.1% or 0.1%. Stated differently, in these alternative embodiments, the anodes 490-492 in the example shown in FIG. 35 may be automatically assigned 33.3%, 33.3%, and 33.4% of the total anodic current, respectively, or even 33.33%, 33.33%, and 33.34% of the total anodic current, respectively.

The present disclosure also allows for lock control. For example, one of the three anodes 490 may be "locked" into a particular percentage of total anodic current, in this case 42% of the total anodic current. In some embodiments, the locking may be done by the user pressing down on (and holding) the target electrode via the graphical user interface 100. In other embodiments, the locking may be done via another suitable interactive engagement via the user interface 100. A visual indicator 495 (such as a picture of a lock or another suitable symbol) may be displayed adjacent to the "locked" electrode (in this case the anode 490) to indicate its "locked" status.

As a result of the anode 490 being "locked", the anode 490 will be assigned to a fixed percentage number (42% in this case) of the total anodic current, regardless of the actual total amount of the anodic current. For example, if the total anodic current is 5 mA, then the actual amount of anodic current through the anode 490 will be 42%×5 mA=2.1 mA. If the total anodic current is increased to 10 mA, then the actual amount of anodic current through the anode 490 will be 42%×10 mA=4.2 mA. This percentage (42%) of anodic current assigned to the anode 490 will remain the same as long as the anode 490 is "locked." Meanwhile, the rest of the anodic current will be automatically split between the remaining anodes 491-492. Therefore, each of the remaining anodes 491-492 will receive 29% of the total anodic current ((100%−42%)/2=29%).

Figure 36:
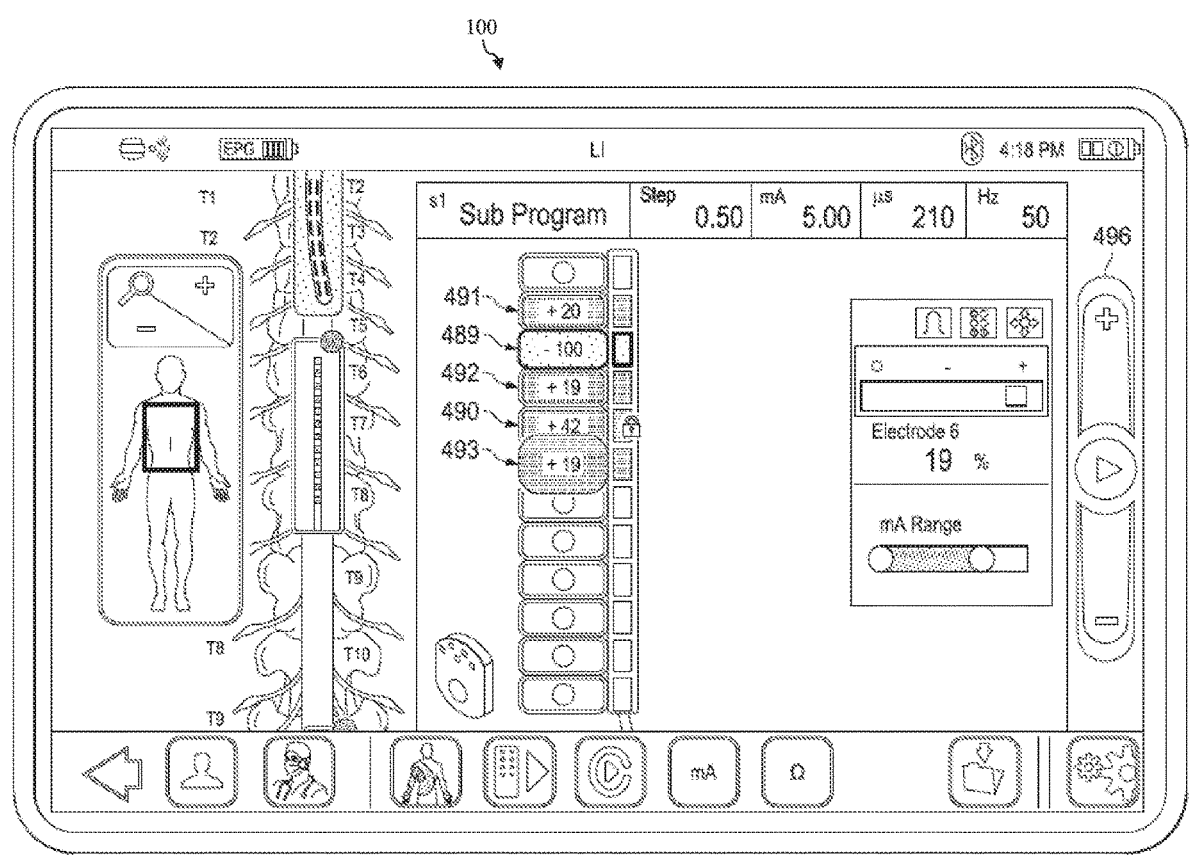
Figure 37:
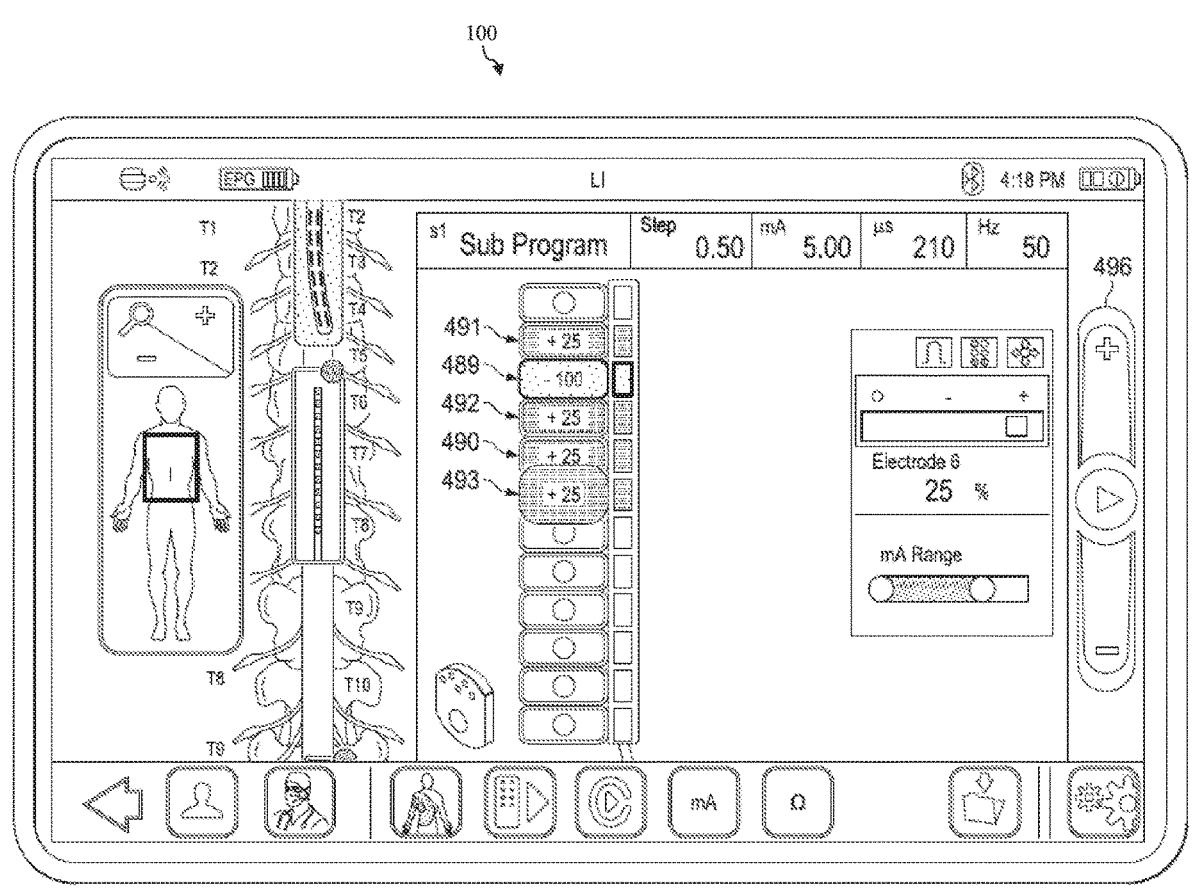

Referring now to FIG. 36, suppose the user has added an additional anode 493 while the anode 490 is still locked. In that case, the remaining percentage of the anodic current (still 58%) will be split substantially equally between the three other unlocked anodes 491-493. In the illustrated embodiment, since 58% cannot evenly be divided by 3, the anode 491 may be automatically distributed 20% of the total anodic current, while the anode 492 and the newly-added anode 493 may be automatically distributed 19% of the total anodic current. Of course, it is possible that the anodes 491-493 each be assigned approximately 19.3% of the total anodic current in alternative embodiments.

Had the anode 490 not been locked down, however, the addition of the new anode 493 will cause the four anodes 490-493 to each be distributed about 25% of the total anodic current. In fact, referring now to FIG. 37, as soon as the anode 490 is released from being "locked" (for example by long pressing it again), the total stimulation current (anodic current in this case) will be automatically divided (substantially evenly) among the four anodes 490-493, with each anode receiving about 25% of the total anodic current.

It is understood that the "locking" of the current for any particular electrodes does not necessarily prevent the user from manually changing the current for that particular electrode. For example, even though the anode 490 in FIG. 36 is "locked" into 42% of the total stimulation current, a user may engage with a virtual control mechanism 496 to adjust the percentage of total stimulation current that is assigned to the anode 490. In this case, a press on the "+" sign increases the percentage of current by 1%, and a press on the "−" sign decreases the percentage of current by 1%. In other embodiments, different types of virtual control mechanisms may be used, such as virtual sliders, virtual knobs, virtual keys, or even fields that allow text entry. In any case, as the percentage number of the stimulation current assigned to any "locked" electrode is adjusted, the remaining percentage of the total stimulation current may then be automatically redistributed to the remaining activated electrodes having the same polarity as the "locked" electrode. For example, in the embodiment illustrated in FIG. 36, if the current percentage assigned to the anode 490 is changed "on the fly" from 42% to 40%, then the current percentage assigned to each of the remaining anodes 491-492 will be automatically changed to 30% "on the fly" as well, even if the anode 490 is still "locked".

In alternative embodiments, the locking of a particular electrode may also be a "hard lock" such that once a current percentage is assigned to the electrode and it is locked, the user cannot freely change the current percentage. Instead, the user needs to "unlock" the electrode first before being able allowed to change the current percentage assigned to it. Regardless, once the particular one or more electrodes are "locked", the remaining current will still be automatically distributed among the rest of the electrodes having the same polarity as the "locked" electrodes.

It is also understood that although anodes are used as examples herein, the same concept applies to cathodes as well. Again, the automatic current balancing discussed herein refers to the percentage of total anodic/cathodic current assigned to each electrode, rather than the actual amount of anodic/cathodic current assigned to each electrode.

Figure 38:
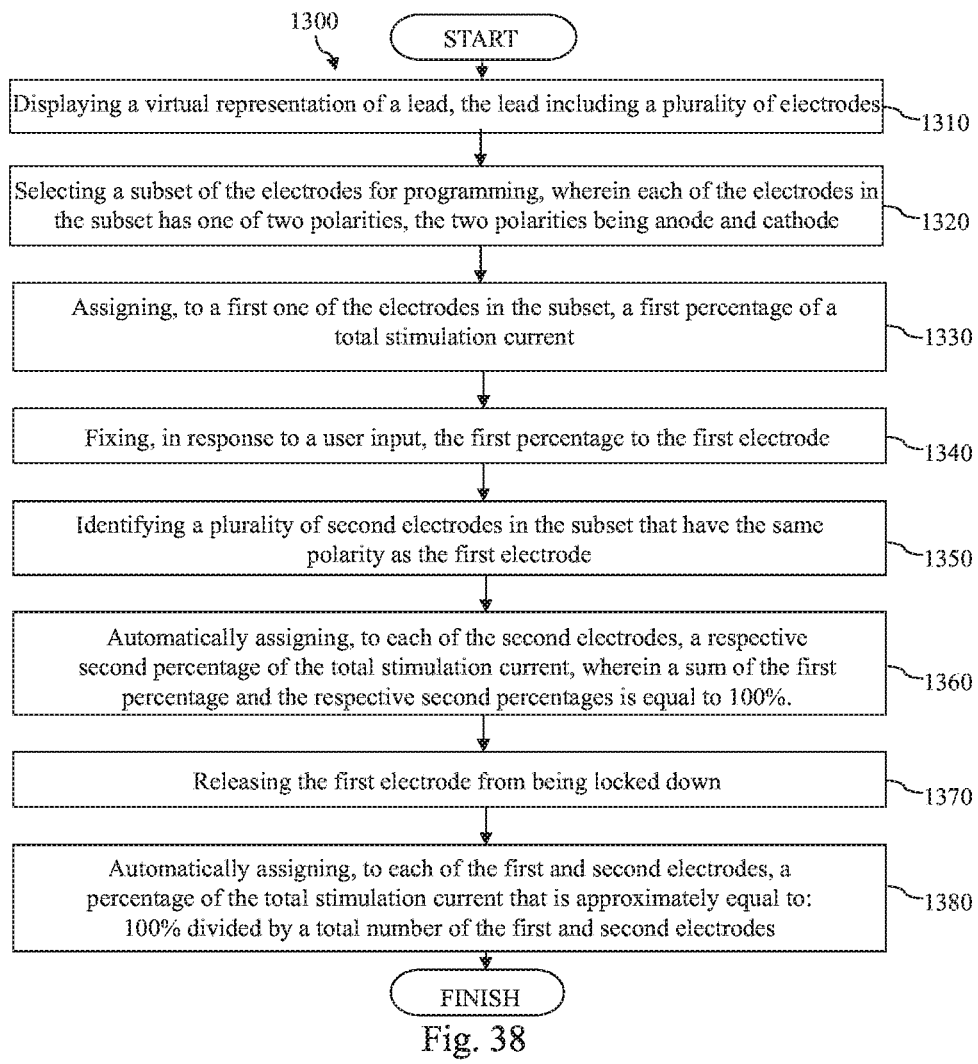
FIG. 38 is a flowchart illustrating example process flows for automatic current balancing and lock control according to various aspects of the present disclosure.
Figure 39:
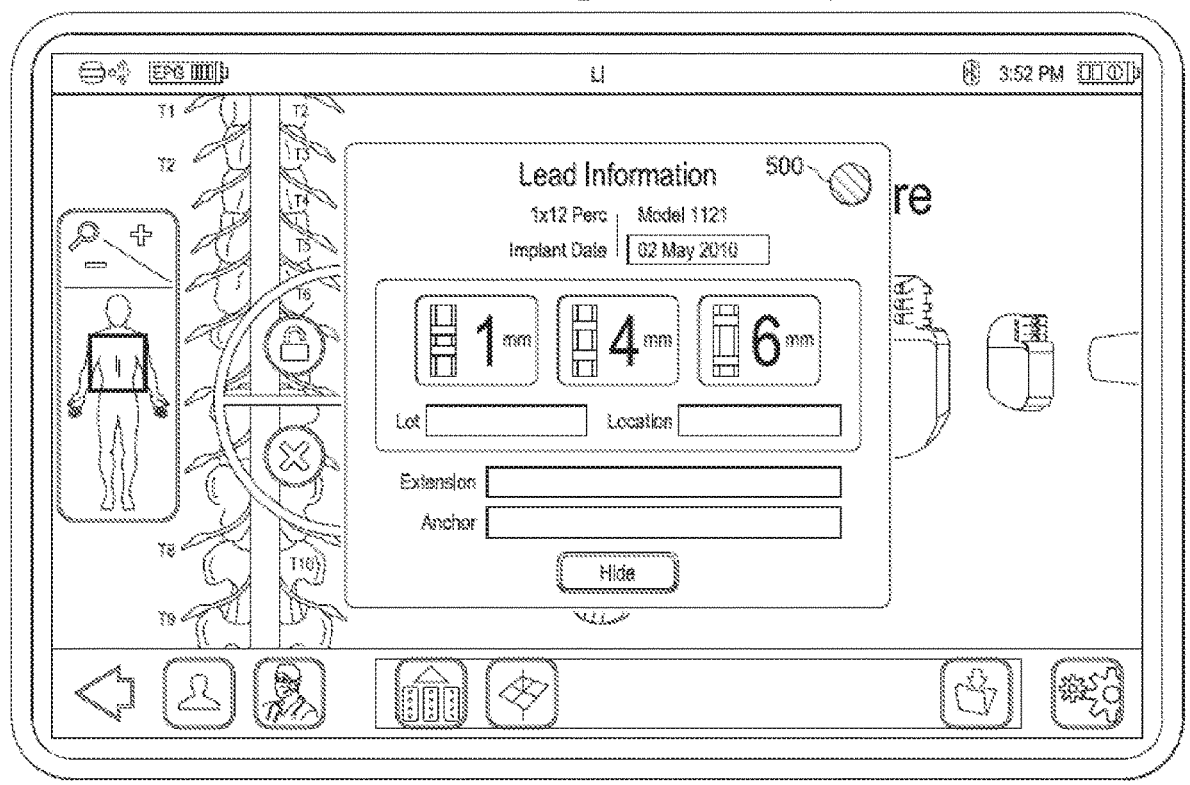

Referring now to FIG. 38, a flowchart illustrating a method 1300 of programming electrodes on a lead is illustrated. The method 1300 includes a step 1310 of displaying a virtual representation of a lead, the lead including a plurality of electrodes.

The method 1300 includes a step 1320 of selecting a subset of the electrodes for programming, wherein each of the electrodes in the subset has one of two polarities, the two polarities being anode and cathode.

The method 1300 includes a step 1330 of assigning, to a first one of the electrodes in the subset, a first percentage of a total stimulation current. In some embodiments, the step 1330 of automatically assigning comprises calculating the respective second percentages based on the following mathematical formula: the respective second percentages are each approximately equal to (100%−the first percentage)/(a total number of the second electrodes). In some embodiments, the total stimulation current is one of: a total anodic current or a total cathodic current. In some embodiments, the respective second percentages are within 1% of one another. In some embodiments, the first percentage is different from each of the respective second percentages.

The method 1300 includes a step 1340 of fixing, in response to a user input, the first percentage to the first electrode. In some embodiments, the step 1340 comprises displaying a symbol adjacent to the first electrode, the symbol indicating that the percentage of stimulation current of the first electrode has been fixed to the first percentage.

The method 1300 includes a step 1350 of identifying a plurality of second electrodes in the subset that have the same polarity as the first electrode.

The method 1300 includes a step 1360 of automatically assigning, to each of the second electrodes, a respective second percentage of the total stimulation current. A sum of the first percentage and the respective second percentages is equal to a predetermined percentage. In some embodiments, the predetermined percentage is 100%. Note that in some embodiments, just the sum of anodic stimulation currents and the sum of the cathodic stimulation currents have to be equal, even if less than 100%.

The method 1300 includes a step 1370 of releasing the first electrode from being locked down.

The method 1300 includes a step 1380 of automatically assigning, to each of the first and second electrodes, a percentage of the total stimulation current that is approximately equal to: 100% divided by a total number of the first and second electrodes. In some embodiments, a sum of the first and second electrodes is less than a total number of the electrodes in the subset.

In some embodiments, one or more of the steps 1310-1380 are performed via a touch-sensitive graphical user interface of a clinician programmer.

It is also understood that the method 1300 may include additional steps that may be performed before, during, or after the steps 1310-1380. For example, the method 1300 may include a step of displaying a window by the virtual representation of the lead, wherein the window contains one or more programming parameters of one of the electrodes of the lead. As another example, the method 1300 may include a step of selecting a third electrode for programming, the third electrode having the same polarity as the first and second electrodes, as well as a step of automatically assigning, to the third electrode and each of the second electrodes, a respective third percentage of the total stimulation current, wherein a sum of the first percentage and the respective third percentages is equal to 100%. In some embodiments, the step of automatically assigning the respective third percentage comprises calculating the respective third percentages based on the following mathematical formula: the respective third percentages are each approximately equal to (100%−the first percentage)/(a total number of the second and third electrodes). Other additional steps may be performed but are not discussed herein for reasons of simplicity.

Display of Lead History Information

The clinician programmer of the present disclosure is configured to retrieve and display information relating to a lead. For example, referring now to FIG. 39, when a lead is connected to an implantable pulse generator (IPG) or external pulse generator (XPG), the clinician programmer will "remember" which bore of the IPG or EPG the lead is connected to, which in the illustrated embodiment is represented by the color of the bore indicator 500. Other types of lead information retained by the clinician programmer includes the type of lead, manufacturer information of the lead, the implant date of the lead or the implant date of the IPG associated with the lead, orientation of the lead as it was implanted, and the implant location of the lead and/or the implant location of the IPG. In some embodiments, the specific portions of the spine near the lead may also be indicated, such as T4-T5, C2-C3, etc.

The retaining and retrieval of lead history may be beneficial to the user of the clinician programmer. For example, suppose the patient goes to India (or another foreign country) on vacation, a different physician uses a clinician programmer to interrogate the IPG. The clinician programmer may then be able to retrieve information relating to the lead and see that the lead has migrated, for example by comparing the retrieved lead history information to a fluoroscopy.

Display of Impedance History Information

Figure 40:
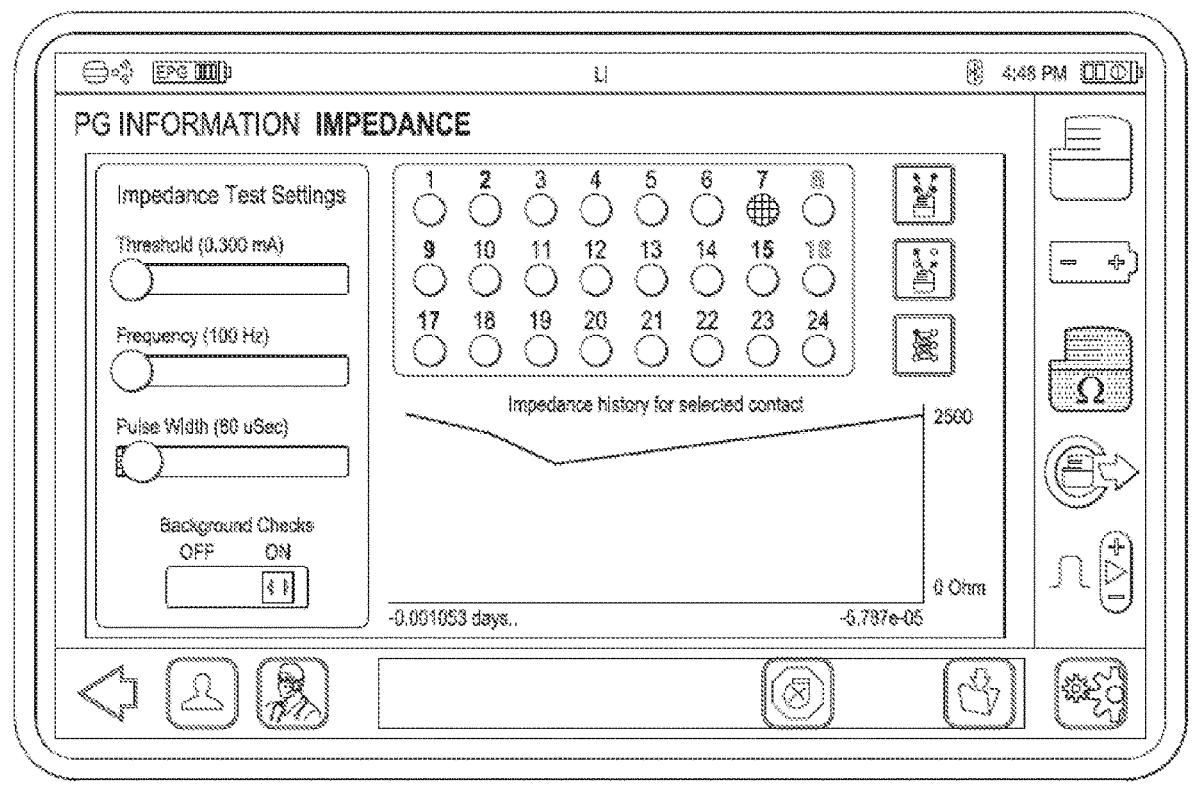
Figure 4I:
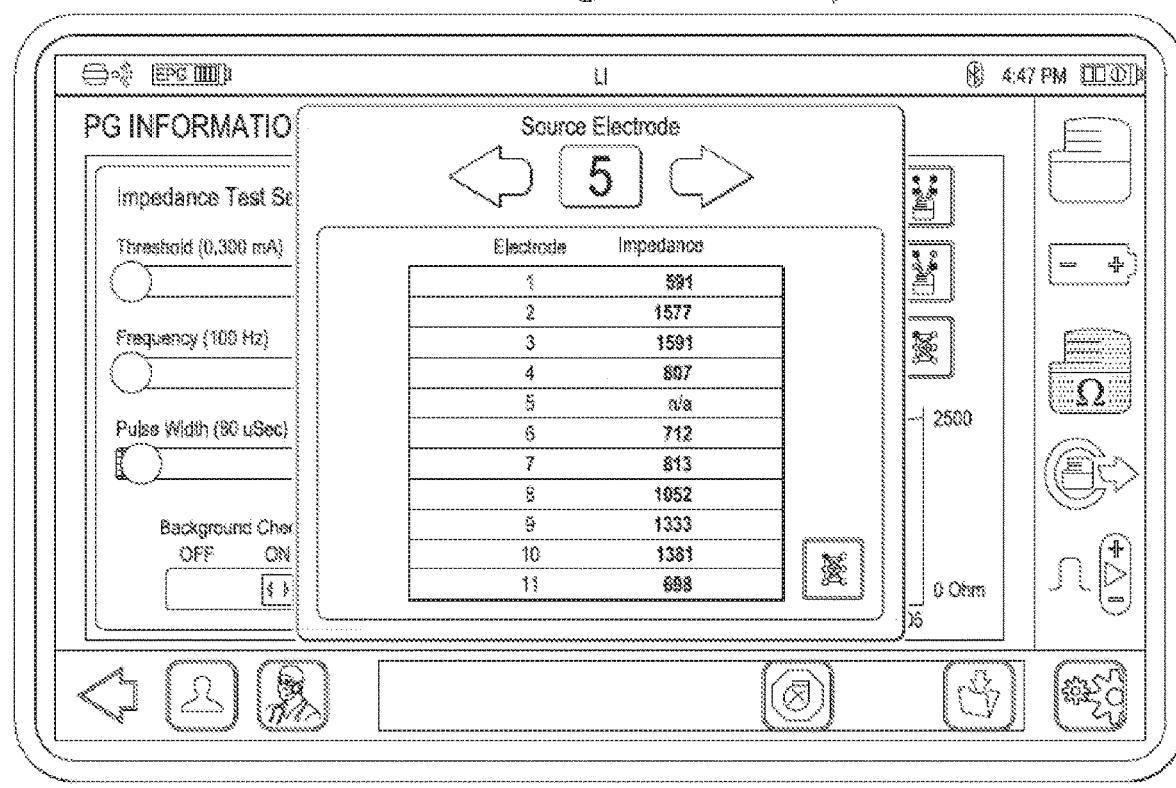

The clinician programmer of the present disclosure is configured to retrieve and display an impedance history of the output channels of the lead. For example, 24 output channels are shown in FIG. 40. Each of the output channels corresponds to one electrode contact. It is desirable to monitor the impedance history of each channel. For example, the impedance for each channel is a summation of all impedance elements in series, which may include the IPG, contact lead, lead body, contact itself, and/or body tissue. Most of these elements are resistive in nature, though the body tissue may contain reactive components and may behave more like an R-C component. The impedance for each channel may be monitored for as long as needed to establish an impedance history, for example an impedance history over a few weeks, a few months, or even a few years.

An example impedance history is shown in FIG. 40 as a plot. The example impedance history plot is for a particular selected channel (e.g., channel 7 in the illustrated embodiment but may be any of the channels 1-24 in other embodiments). The X-axis of the plot represents time, and the Y-axis of the plot represents impedance. In some other embodiments, the impedance history for multiple channels may be plotted concurrently. The contacts representing the channels 1-24 in FIG. 40 may also be color-coded to indicate the impedance of that channel. For example, a green contact may indicate low impedance, an orange contact may indicate medium impedance, and a red contact may indicate high impedance. This offers the user a quick visual impedance landscape of the channels. Furthermore, the impedance history may also be shown as text, such as that shown in FIG. 41, where the impedances for a number of electrodes are displayed.

Impedance history is a useful tool in making diagnosis and trouble-shooting. After surgery, the impedance history for each channel usually follows an expected pattern if all is normal. However, if there are mechanical problems, the impedance history will reflect these problems. For example, if an abnormally high impedance is observed, that corresponds to an open circuit condition, which may indicate a lead has been snapped (or another potential open circuit in the channel). On the other hand, if an abnormally low impedance is observed, that corresponds to a short circuit condition, which may indicate a wire in the lead is touching another wire (or another potential short circuit in the channel). The healthcare professional may then try to repair the channel to fix the problem indicated by the impedance history.

It is noted that for mechanical problems such as open/short circuit conditions discussed above, the change in impedance usually will be dramatic. However, if the impedance history does not have a dramatic variation but nevertheless deviates from an expected pattern, then that may indicate an underlying problem with the tissue. For example, if the tissue is being inflamed, the impedance may experience a drop over time. Such drop in impedance may not be dramatic but is still noticeable to indicate a problem exists. Similarly, other problems with the tissue may manifest themselves in various impedance history patterns. Therefore, the impedance history may be used to not only discover and trouble a mechanical problem with the channel, but also an underlying condition for the tissue that needs to be addressed.

Transferring Content Between Pulse Generators

The clinician programmer of the present disclosure is configured to replace contents from one pulse generator to another. For example, the contents such as pain and stimulation maps and various programming parameters of a first pulse generator may be easily transferred to a second pulse generator with the click of a button in the user interface of the clinician programmer. The first pulse generator may be an IPG or an EPG, and the second pulse generator may also be an IPG or an EPG. Thus, the content replacement may take place from an IPG to an IPG, from an EPG to an EPG, from an IPG to an EPG, or from an EPG to an IPG.

In some embodiments, the first time a clinician programmer is connected to a pulse generator, the clinician programmer interrogates the pulse generator whether the pulse generator has been programmed by a clinician programmer of the present disclosure. Such clinician programmer may or may not be the programmer that is currently interrogating the pulse generator. If the pulse generator answers yes, then the clinician programmer will retrieve all the relevant information stored on the pulse generator, for example patient demographic information, stimulation programs (including the various stimulation parameters), number and type of leads connected to the pulse generator, where the leads have been connected to, orientation of the leads, and/or pain maps and stimulation maps. All of this information may be used to automatically create a patient record. The patient record may be stored on the clinician programmer or on a remote database. The patient record may be considered "contents" of the pulse generator and may be quickly loaded onto a different pulse generator according to the present disclosure.

Figure 42:
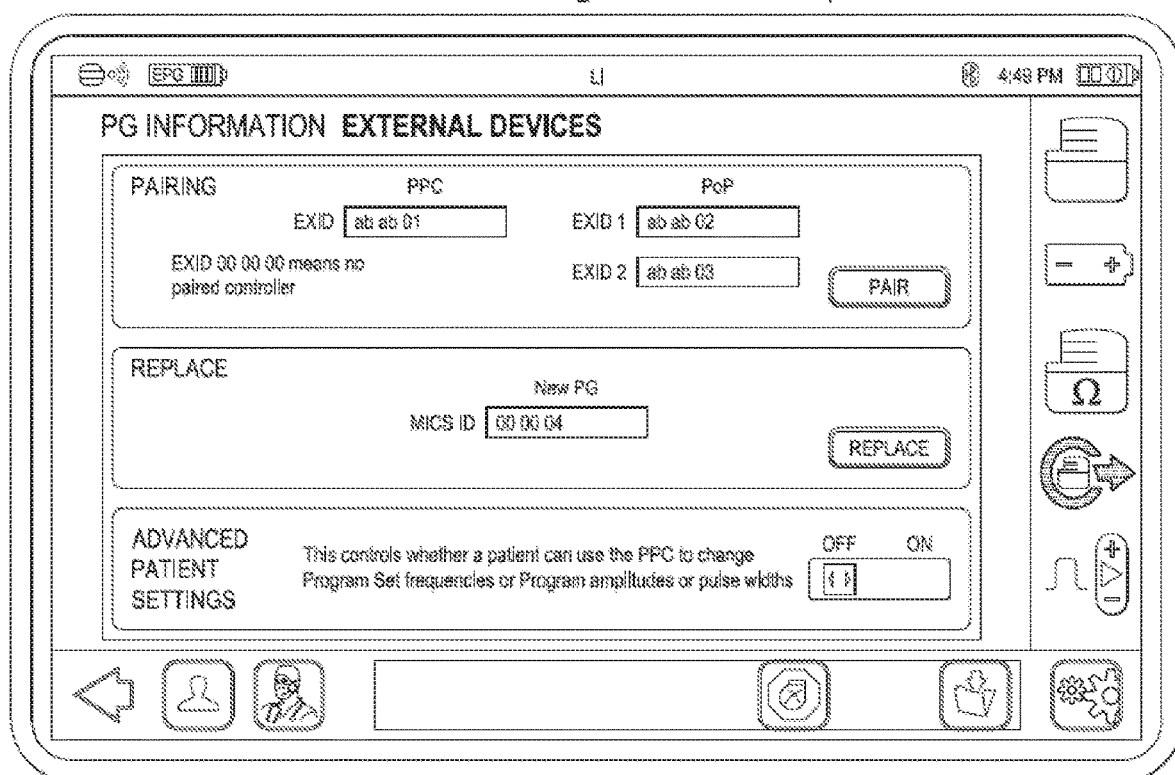

Referring to FIG. 42, the portion of the user interface 100 that allows for such easy content replacement is shown. The new pulse generator (onto which the contents of the old pulse generator should be transferred) is identified through a Medical Implant Communication Service (MICS) ID, in this case 00 00 04 as an example. After inputting the MICS ID, the user merely needs to click on the button "REPLACE", and the contents (e.g., the patient record as discussed above) of the old pulse generator (including pain/stimulation maps, patient information, and/or stimulation parameters) are downloaded or transferred to the new pulse generator associated with the MICS ID 00 00 04. This quick transfer of pulse generator content saves the clinician from having to manually input information stored from one pulse generator to another.

Restoring Pulse Generator to its Default State

Figure 43:
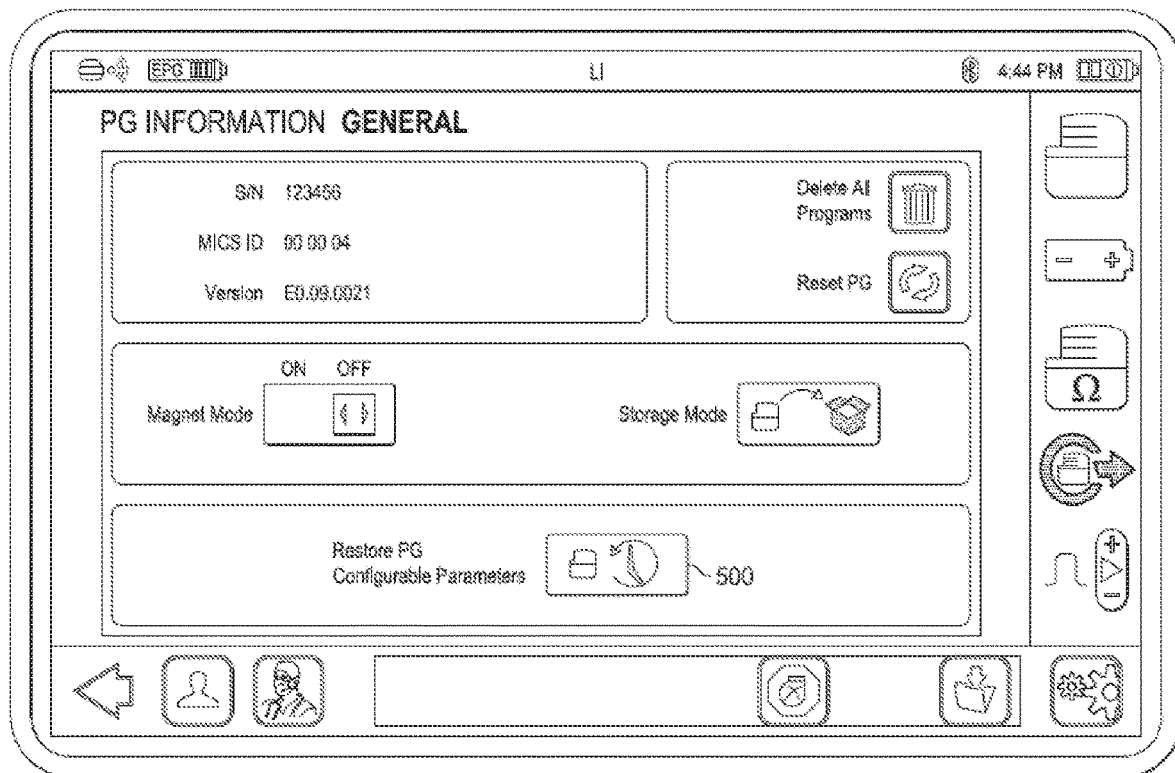
Figure 44:
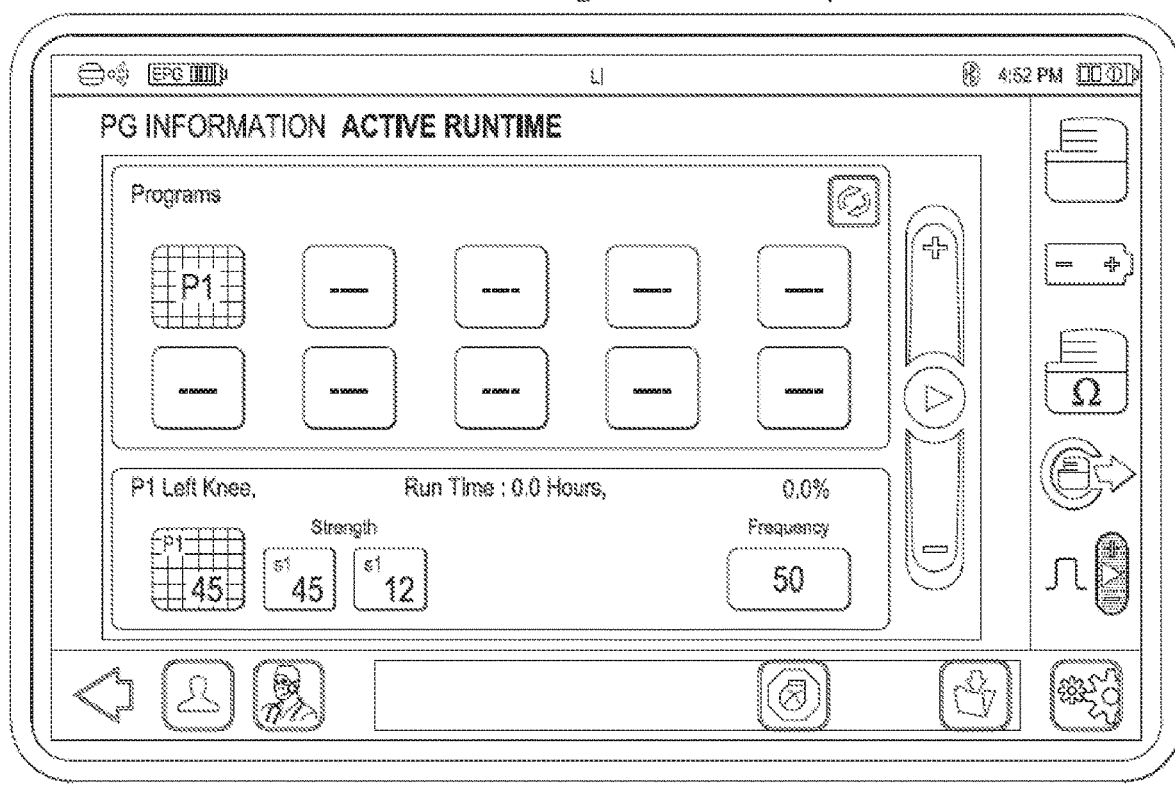

The clinician programmer of the present disclosure is configured to restore a pulse generator to its default state. The first time the clinician programmer is connected to the pulse generator, for example an IPG, the clinician program copies the state of the IPG and saves it. The state of the IPG may include information such as configurable device parameters, trim lists, lead constants, etc. The state of the IPG may then be saved in a remote database or in the clinician programmer itself. At a later point in time, if the IPG ever gets into a state where it is unusable, the clinician programmer can be used to restore the IPG to its initial state, since the clinician programmer has already copied the state information from the IPG previously. For example, as shown in FIG. 43, the user can click on a button 505 of the user interface 100 to restore the IPG to a usable state.

Patient Stimulation Control Using Clinician Programmer

The clinician programmer of the present disclosure is configured to provide patient stimulation control. In more detail, as a healthcare professional (i.e., the user) is trying to determine what works best for the patient, the clinician programmer functions in a trial mode. When a patient goes home, patient stimulation is being controlled by a patient programmer or another suitable portable control device that the patient can carry. Now suppose the patient comes in to the healthcare professional's office but forgets to bring his/her patient programmer (e.g., left it in his/her car). The patient may still request the healthcare professional to adjust the stimulation. The healthcare professional may use the clinician programmer to carry out this task, for example using a user interface shown in FIG. 44. The user interface shown in FIG. 44 essentially emulates how a patient programmer can be used to adjust the stimulation parameters. Therefore, using a clinician programmer (that functions similar to a patient programmer in this aspect), the stimulation can be adjusted and started for the patient before the patient is sent home.

3D View of Spine and Implants and Visual Display of Excitation Fields

Figure 45:
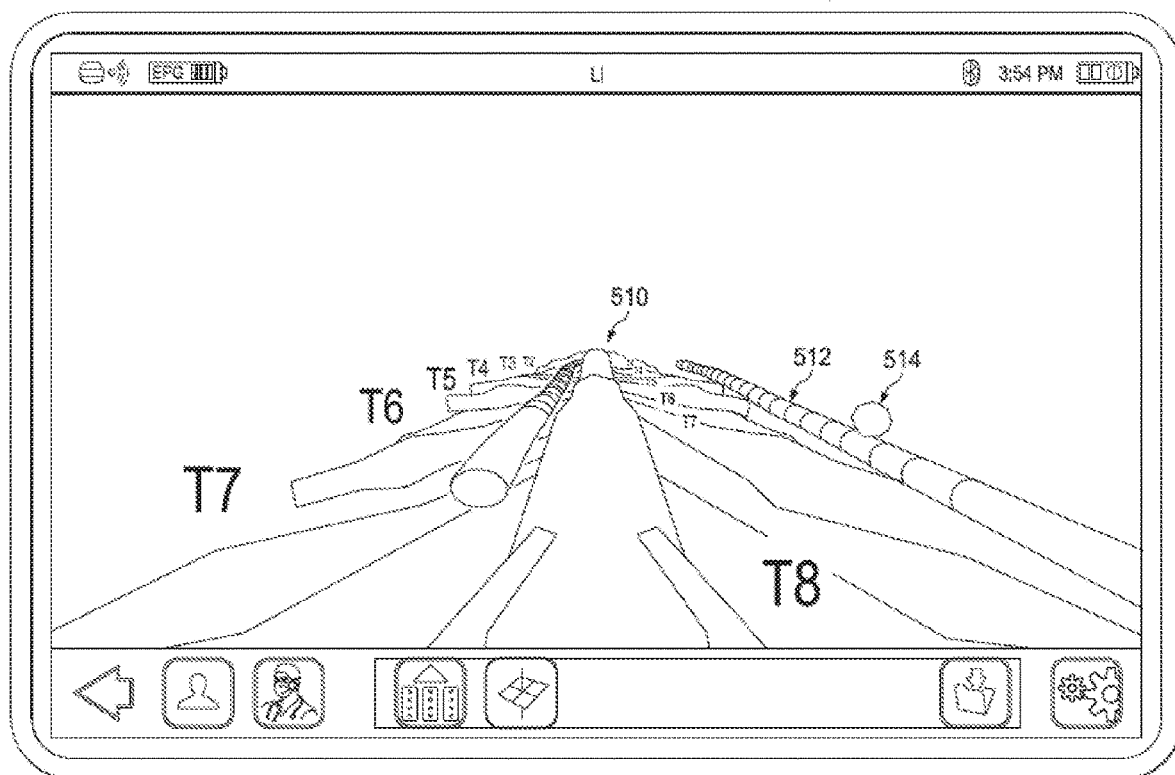

Referring now to FIG. 45, the clinician programmer of the present disclosure is configured to provide a 3D view of a portion of the spine 510 as well as one or more implantable medical devices (such as leads) 512 next to the spine 510. The 3D view allows the user to envision the implant situation more accurately. In addition, an excitation field may be illustrated in the 3D view. In more detail, anodes and cathodes do not provide the same amount of stimulation to the nerves, even if they are programmed to have equal stimulation currents. In fact, anodes typically require 3-5 times more current than cathodes to achieve the same degree of stimulation for the nerves. In other words, the nerves do not "see" electric fields, they see "excitation fields" provided by the electrodes, which are different depending on whether the electrode is an anode or a cathode. In some embodiments, the excitation fields are calculated or derived as a function of the electric field generated by the electrodes. For example, the excitation fields may be derived as a derivative of the electric field.

To help illustrate what the nerves actually experience, the user interface 100 of the clinician programmer visually displays excitation fields in the 3D view of the spine. For example, an example excitation field 514 is shown in FIG. 45 next to an activated electrode. The excitation field 514 is an excitation field associated with an anode. Now, assuming the same amount of current is applied to the same electrode, but the polarity of the electrode is switched to a cathode. A different excitation field 515 shown in FIG. 46 would be generated and experienced by the nearby nerves. Note that the excitation field 515 is substantially greater in size than the excitation field 514, since the excitation field 515 is associated with a cathode, and the excitation field 514 is associated with a cathode, and as discussed above cathodes generate much bigger excitation fields than anodes.

It is understood that the excitation fields 514 and 515 illustrated herein are merely examples to show that the clinician programmer herein can show what the nerves actually experience (e.g., by applying corrections to the electric fields). The excitation fields 514-515 do not necessarily reflect the exact shape and size of real excitation fields.

III. Settings and Preferences

User Preferences and Default Stimulation Parameters for Each User

The clinician programmer of the present disclosure has various settings that can be used for the user's programming convenience as well as safety control. For example, referring to FIG. 47, the portion of the user interface 100 shown involves associating default stimulation parameters for each user. As discussed above, the clinician programmer can be used by a plurality of users. Each user may have its own preference for setting or programming the stimulation parameters. For example, a user A may prefer to have a full range of amplitude control, but may prefer to start the frequency from 1 Hz and operate within a range from about 1 Hz to about 30 Hz. Similarly, the user A may prefer to always work with a pulse width range from about 0.1 micro-seconds to about 10 micro-seconds. These user preferences may be expressly set by the user A, or may be programmed into the clinician programmer. Thereafter, whenever the user A logs on to the clinician programmer again, and the user creates a new stimulation program, the stimulation fields (e.g., amplitude, frequency, pulse width, etc.) are automatically populated with these user preferences, which are also referred to as user default stimulation parameters. This saves the user A time and effort in having to manually enter his preferred default stimulation parameters. In a similar manner, users B, C, D, etc. may each have their own preferred default parameters. When these other users log on to the clinician programmer and try to create stimulation programs, the stimulation fields are automatically populated with their own default stimulation parameters.

In addition, an administrative user may be able to set programming limits for each normal user for safety control purposes. For example, for user A, an administrative user may set the frequency programming range from about 1 Hz to about 85 Hz, and the pulse width programming range from about 0.1 micro-seconds to about 210 micro-seconds. For user B, the administrative user may set different limits for the various stimulation parameters. This may prove beneficial in situations where a relatively inexperienced user may be prevented from making various programming mistakes (e.g., entering stimulation currents that are too high, or pulse width that is too long, etc.).

Emulator with Patient Data

Figure 46:
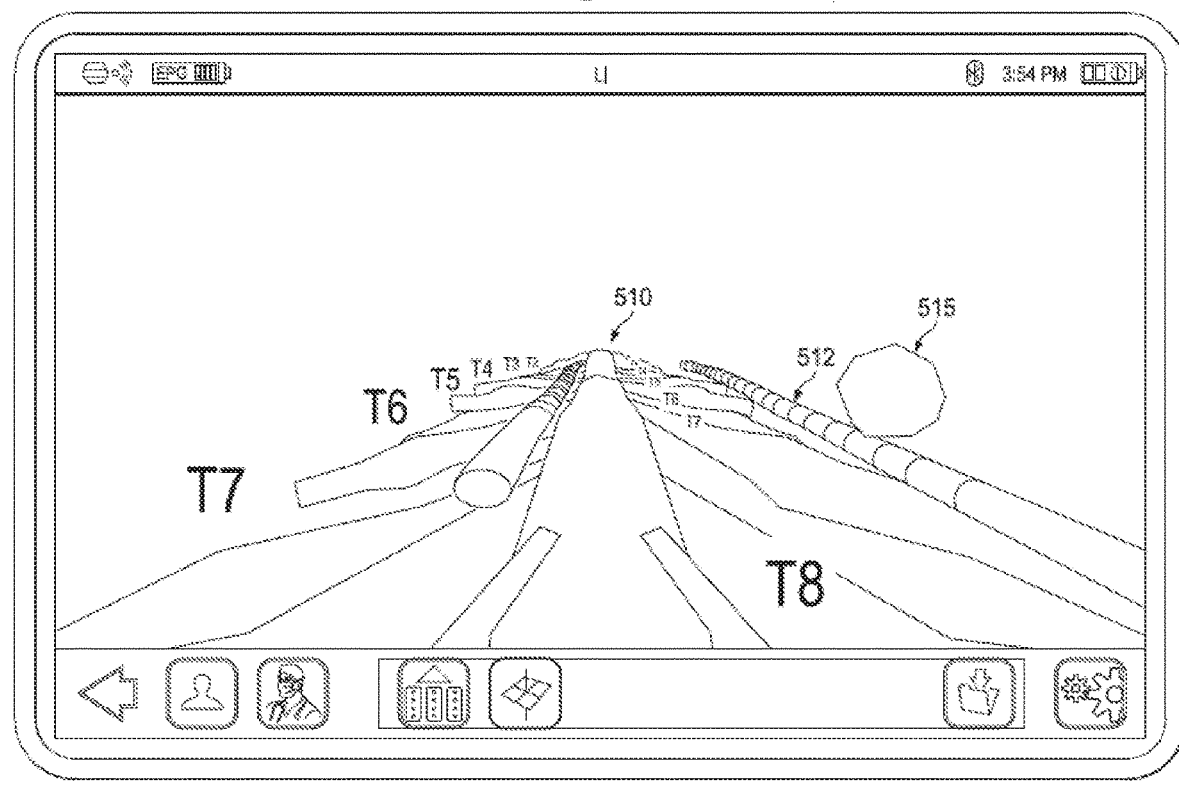
Figure 47:
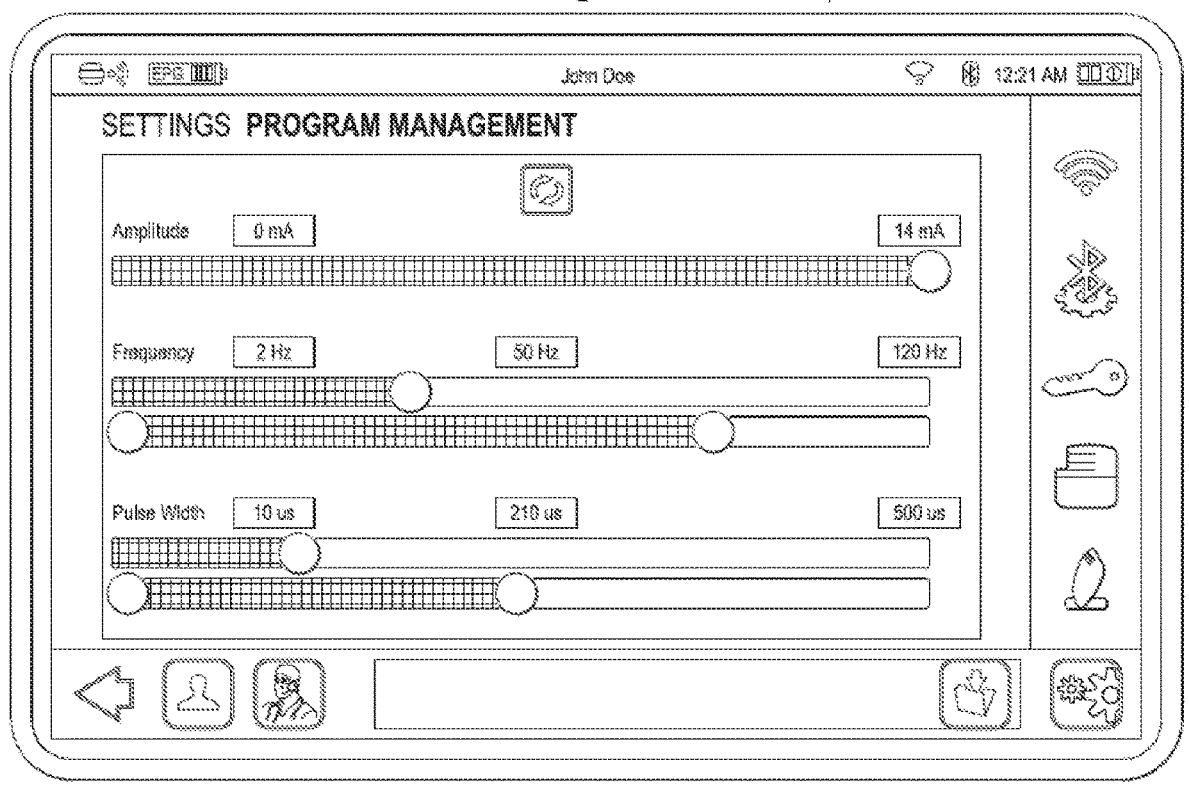
Figure 48:
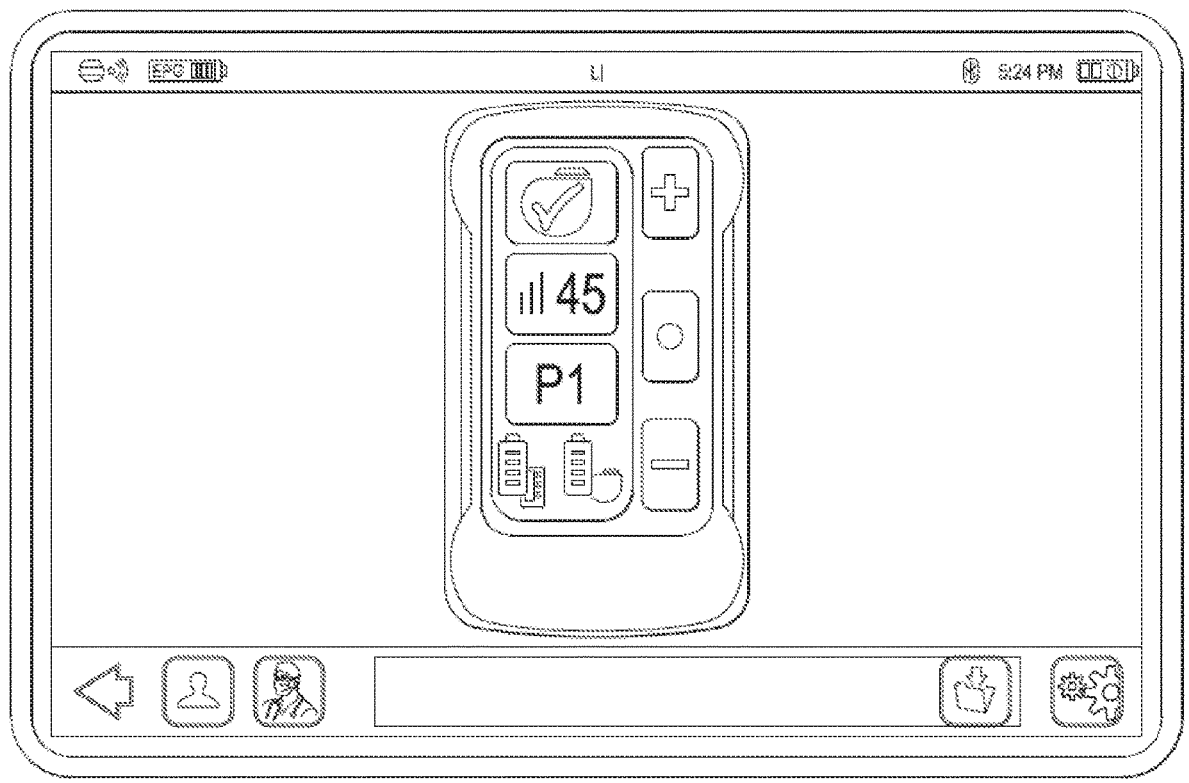
Figure 49:
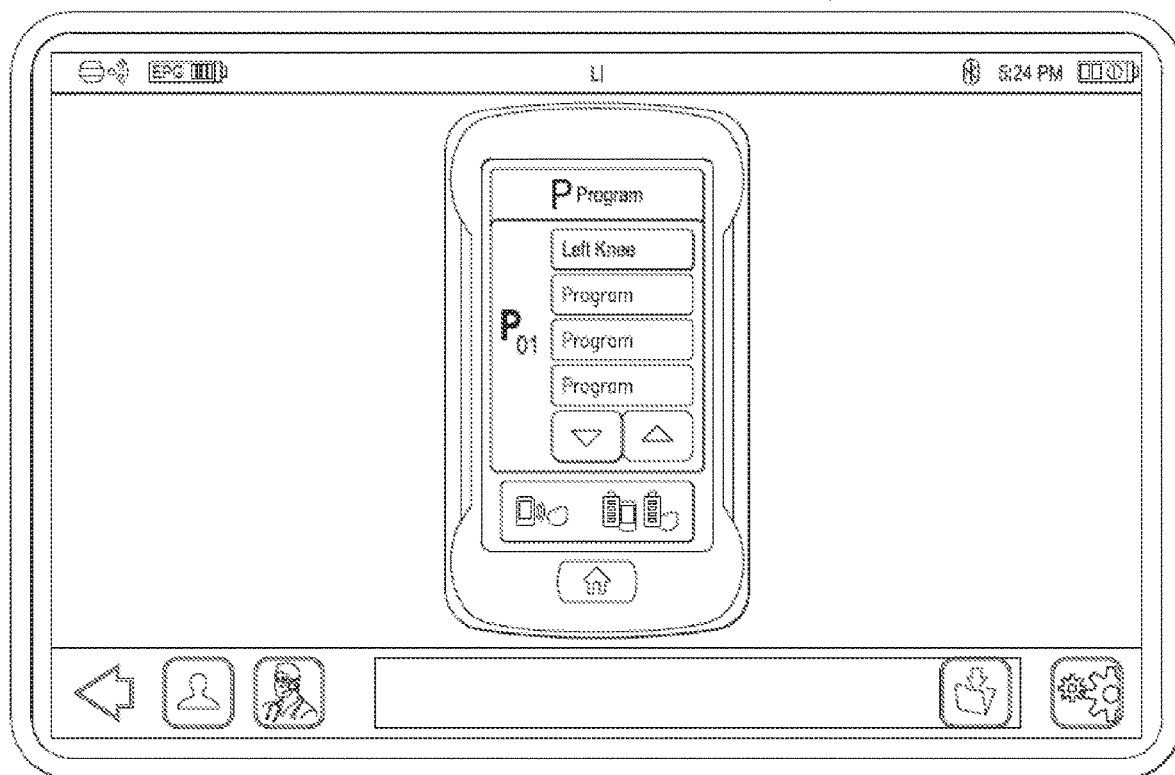

The clinician programmer of the present disclosure is configured to provide an emulation of a patient programing device (e.g., a patient programmer charger (PPC) or a pocket programmer (PoP)), as disclosed in U. S. Provisional Patent Application 61/695,421, filed on Aug. 31, 2012, entitled "Method and System of Emulating a Patient Programmer" to Kaula et al., the content of which is hereby incorporated by reference in its entirety. Referring now to FIGS. 46-47, which illustrate a PoP and a PPC emulated by the user interface 100 of the clinician programmer, respectively. For example, a patient who is having problems may call the healthcare professional. The healthcare professional may use the clinician programmer to retrieve the patient's data, for example from a remote database.

As the emulated PPC or PoP are illustrated on the screen of the clinician programmer, the healthcare professional may be able to give the patient instructions specific to that patient, since the patient's data has already been loaded into the clinician programmer. In other words, the clinician programmer herein does not merely provide an emulation of a patient programmer in general, but that it can provide an emulation of the patient programmer for a specific target patient. The patient may ask questions, and the healthcare professional can walk the patient through various settings or programs in a step-by-step manner, because the healthcare professional can "see" exactly what the patient sees, as the emulated patient programming device illustrated by the user interface 100 is loaded with the same information that is loaded into the patient's actual programming device. By pulling patient data into the emulated patient programming device, the healthcare professional may be able to assist the patient in a more personalized and intuitive manner.

Dynamically Generated Customized Patient Reports

Figure 50:
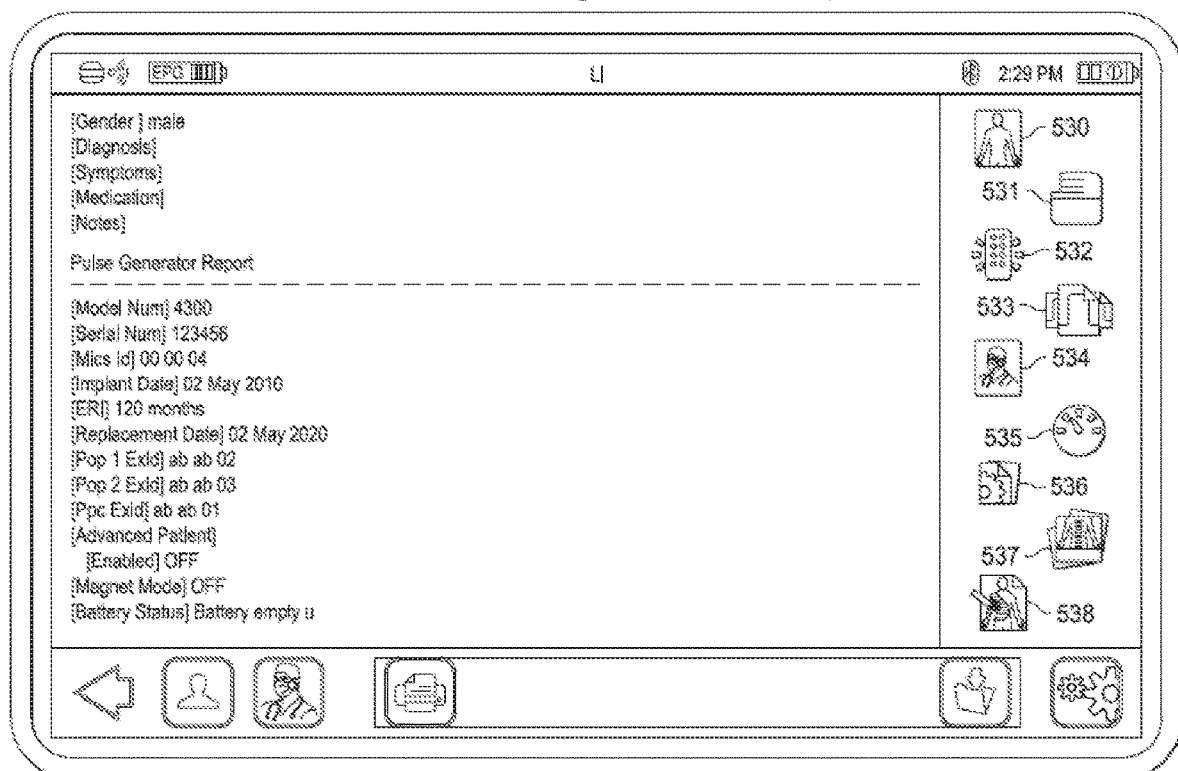
Figure 51:
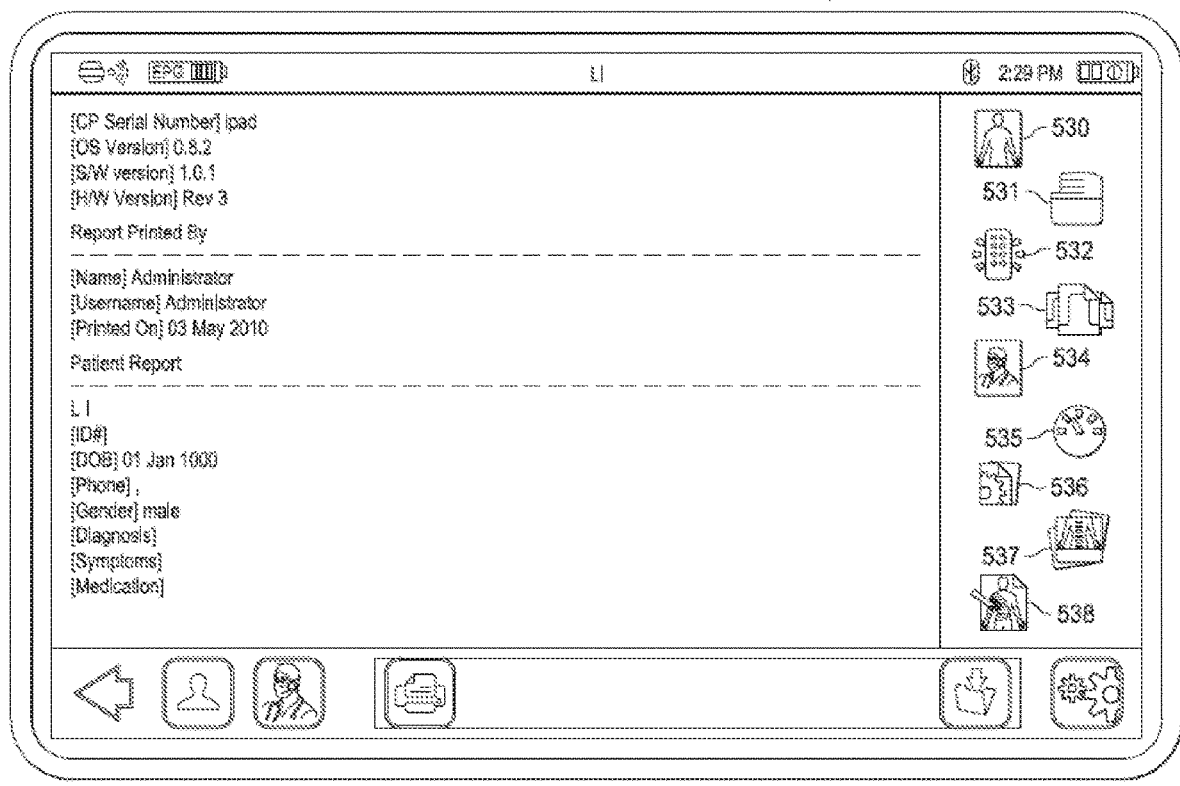

The clinician programmer of the present disclosure is configured to dynamically generate patient reports. Referring to FIGS. 50-51, the user interface 100 displays an example of such dynamically generated patient report. The user interface 100 displays a plurality of icons 530-538. Each icon can be clicked to add more information to the patient report. For example, the icon 530 can be clicked to add a patient (as shown in FIG. 50). The icon 531 can be clicked to add the information regarding a pulse generator (as shown in FIG. 51). The icon 532 can be clicked to add the information regarding leads. The icon 533 can be clicked to add the information regarding stimulation programs. The icon 534 can be clicked to add the information regarding physicians. The icon 535 can be clicked to add the information regarding sessions (e.g., initial session, trial session, permanent session, or follow up session). The icon 536 can be clicked to add the information regarding diagnostics (e.g., impedance data of the electrodes on the lead, etc.). The icon 537 can be clicked to add the information regarding images taken earlier. The icon 538 can be clicked to add the information regarding pain maps, stimulation maps, and their overlapping coverage. It is understood that additional icons may be added in other embodiments to further customize the patient report. Furthermore, it is understood that in some embodiments, the icons may be "dragged and dropped" into the patient report to add the corresponding information to the patient report.

The healthcare professional can dynamically customize the patient report simply by clicking the icons of interest. Suppose the healthcare professional is interested in seeing the information regarding the leads, he/she only needs to click on the icon 532, and the lead information will appear in the patient report. As another example, if the healthcare professional is interested in seeing the diagnostic information and the pain/stimulation maps, he/she merely needs to click on icons 537-538, and the diagnostic information and the pain/stimulation map information will automatically be imported into the patient report. Therefore, the healthcare profession can quickly access information of interest, rather than having to comb through a long patient report to identify the information of interest. The clinician programmer may also be communicatively coupled to a printer, for example a Bluetooth printer. As such, the healthcare professional can print out a customized patient report through this portion of the user interface 100. The approach of generating patient reports as discussed above is modular, and the healthcare professional may decide to generate (and print) as much or as little information as he/she wishes in the patient report.

Additional Miscellaneous Features of the Clinician Programmer and its Eco-System Pulse Generator as Carrier of Information Traditionally, patient information such as the patient's biographical information is stored in a clinician programmer or in a remote database. According to the present disclosure, however, patient information can also be stored in a pulse generator such as an IPG, as described in U.S. patent application Ser. No. 13/604,197, filed Sep. 5, 2012, entitled "Method and System for Associating Patient Records With Pulse Generators" to Kaula et al., the content of which is hereby incorporated by reference in its entirety. Essentially, the pulse generator such as the IPG becomes the carrier of information. In addition to patient biographical information, information that is stored on the pulse generator may include history of pain maps, history of stimulation maps, stimulation parameters, treatment programs, physicians, etc.

As the carrier of information, the pulse generator such as the IPG allows the patient and the healthcare professional to be less dependent of the "cloud" (i.e., the remote database). Since the IPG is implanted in the patient, the patient necessarily travels with all the necessary information needed for his/her treatment. Thus, when a healthcare professional treats a patient, the healthcare professional is no longer entirely dependent on the cloud, even if the patient is a new patient. Instead, the healthcare professional can use the clinician programmer to interrogate the IPG that is implanted in the patient's body and retrieve all the relevant or needed information from the IPG. As a result, both the patient and the healthcare professional enjoy a greater degree of freedom: the patient can now freely travel without worrying about bringing his/her patient and treatment records with him/her, and the healthcare professional need not necessarily manually store or upload patient records and other relevant patient information.

Computer Assisted Stimulation Programing (CASP)

Figure 52:
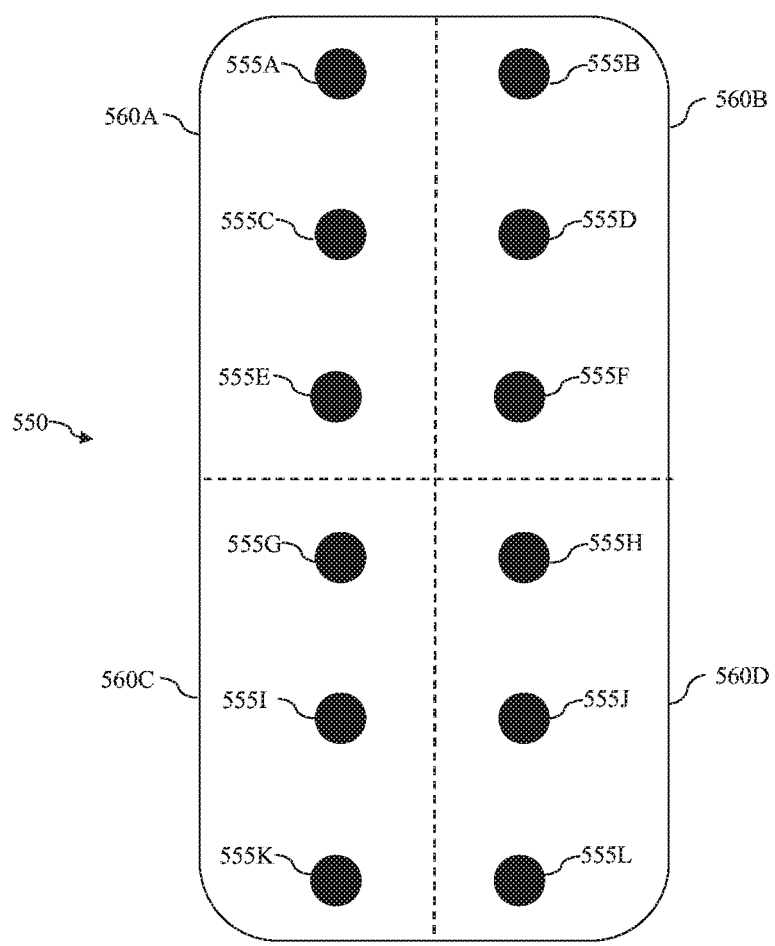
FIGS. 52-53 are simplified diagrams of a lead according to various aspects of the present disclosure.

The present disclosure provides for computer assisted stimulation programming, an embodiment of which is described in U.S. patent application Ser. No. 13/118,764, filed on May 31, 2011, entitled "System and Method of establishing a protocol for providing electrical stimulation with a stimulation system to treat a patient" to Kaula et al, the content of which is hereby incorporated by reference in its entirety. Another Computer Assisted Stimulation Programing (CASP) method is described with reference to FIGS. 52-53. Referring to FIG. 52, an example lead 550 is shown. The lead 550 has electrodes 555A-555L. For each of the leads 555, stimulation current is slowly ramped up simultaneously from zero. As this ramping process takes place, the patient is asked to provide feedback, for example using a patient feedback device. When the patient indicates that he/she is beginning to feel some stimulation, the electrodes on 555 the lead 550 are divided into a plurality of sections, for example into four quadrant sections 560A-560D as shown in FIG. 52. The electrodes 555 in each quadrant section 560 are then turned on (one quadrant section 560 at a time), and the patient is asked if the stimulation sensation is still being felt. If the patient's answer is no, then the corresponding quadrant section 560 is crossed-off, while the quadrant that produces the sensation is investigated further.

Figure 53:
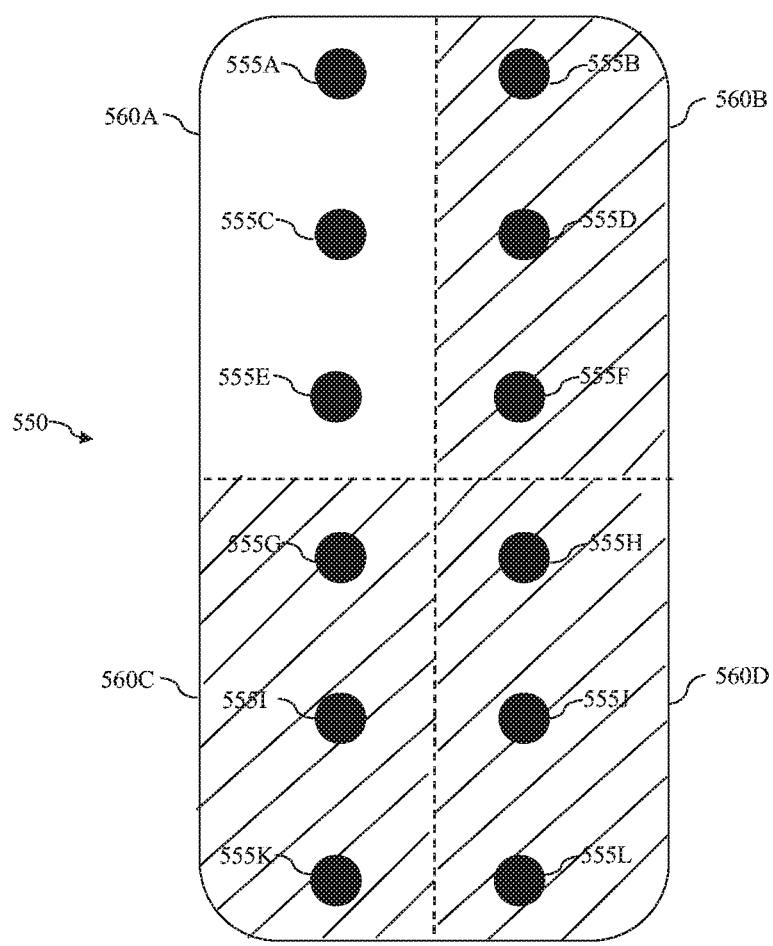

For example, referring now to FIG. 53, the quadrant sections 560B-560D do not produce any stimulation sensations for the patient, and as such they are crossed-off. Only quadrant 560A produced a stimulation sensation for the patient, and therefore it is retained for further investigation. A similar analysis may be repeated for the electrodes 555A, 555C, and 555E in the quadrant section 560A until the electrodes of interest (i.e., the ones producing the stimulation sensation) are identified. A suitable treatment protocol for providing therapeutic electrical stimulation to treat the patient may then be developed accordingly. The CASP process discussed above provides quick and accurate identification of electrodes of interest.

Although the example is illustrated using four quadrant sections, it is understood that in other embodiments, the divided sections need not be quadrants. For example the electrodes may be divided into any suitable two, three, four, five, etc. groups at a time. The divided sections also need not have equal number of electrodes in each section.

Figure 54:
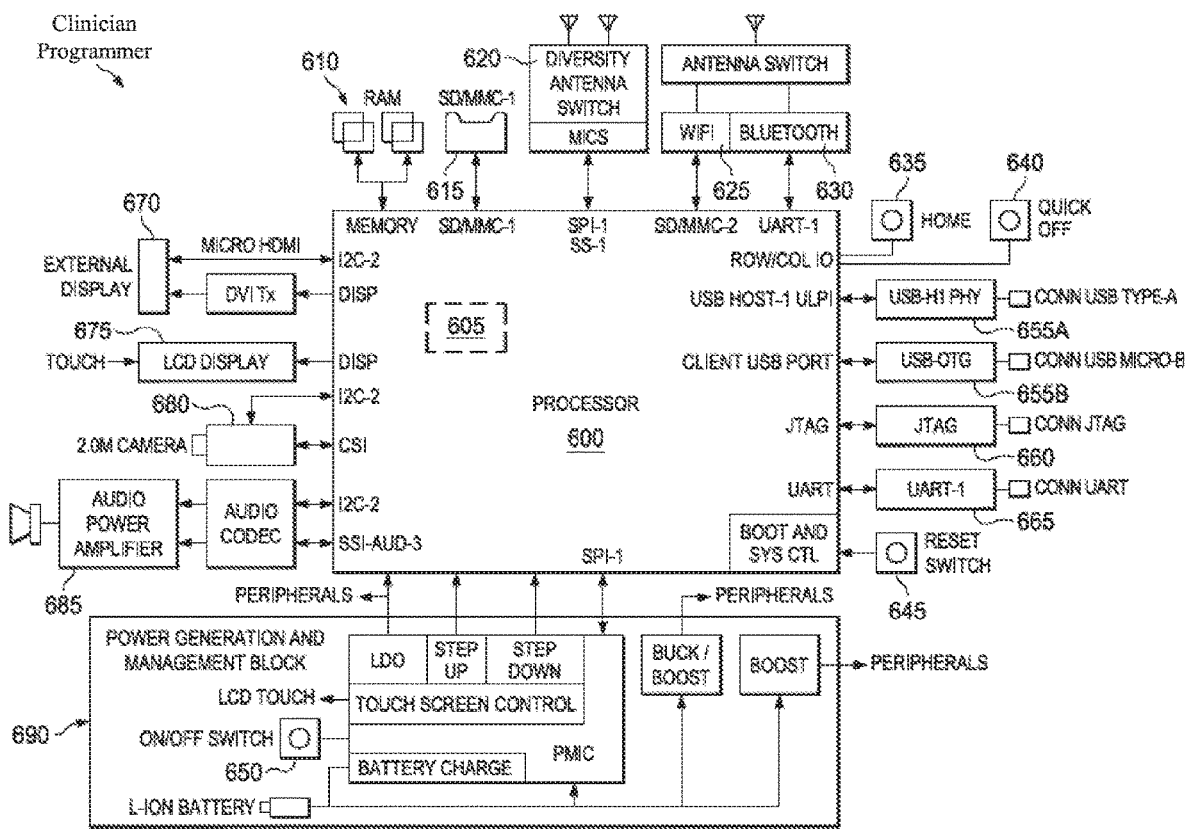
FIG. 54 is a simplified block diagram of an electronic programmer according to various aspects of the present disclosure.

FIG. 54 shows a block diagram of one embodiment of the electronic programmer (CP) discussed herein. For example, the electronic programmer may be a clinician programmer (CP) configured to generate display and display the 3D and 2D pain/stimulation maps discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 54, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX510EC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 54 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 54.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 54.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 54) may also be included for data transfer.

It is understood that a patient programmer may be implemented in a similar manner as the clinician programmer shown in FIG. 54.

Figure 55:
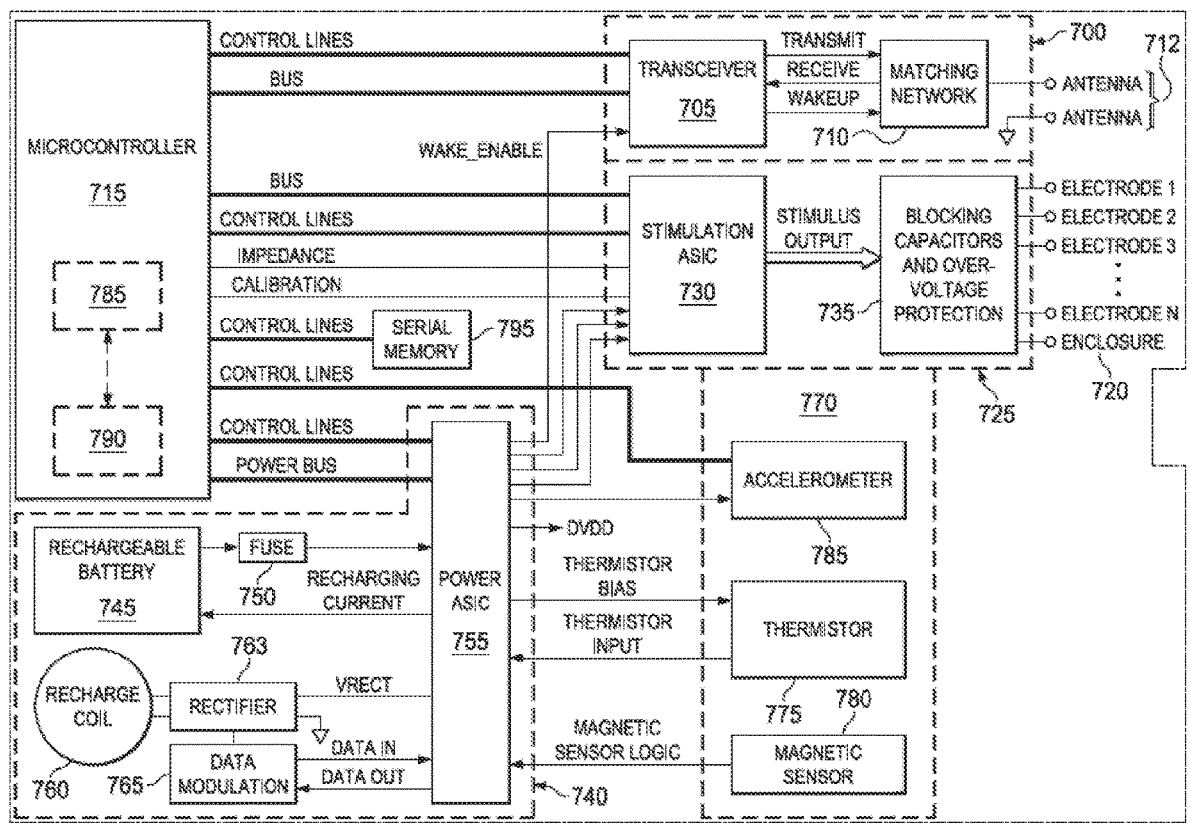
FIG. 55 is a simplified block diagram of an implantable medical device according to various aspects of the present disclosure.

FIG. 55 shows a block diagram of one embodiment of an implantable medical device. In the embodiment shown in FIG. 55, the implantable medical device includes an implantable pulse generator (IPG). The IPG includes a printed circuit board ("PCB") that is populated with a plurality of electrical and electronic components that provide power, operational control, and protection to the IPG. With reference to FIG. 55, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 55, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 55 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 56:
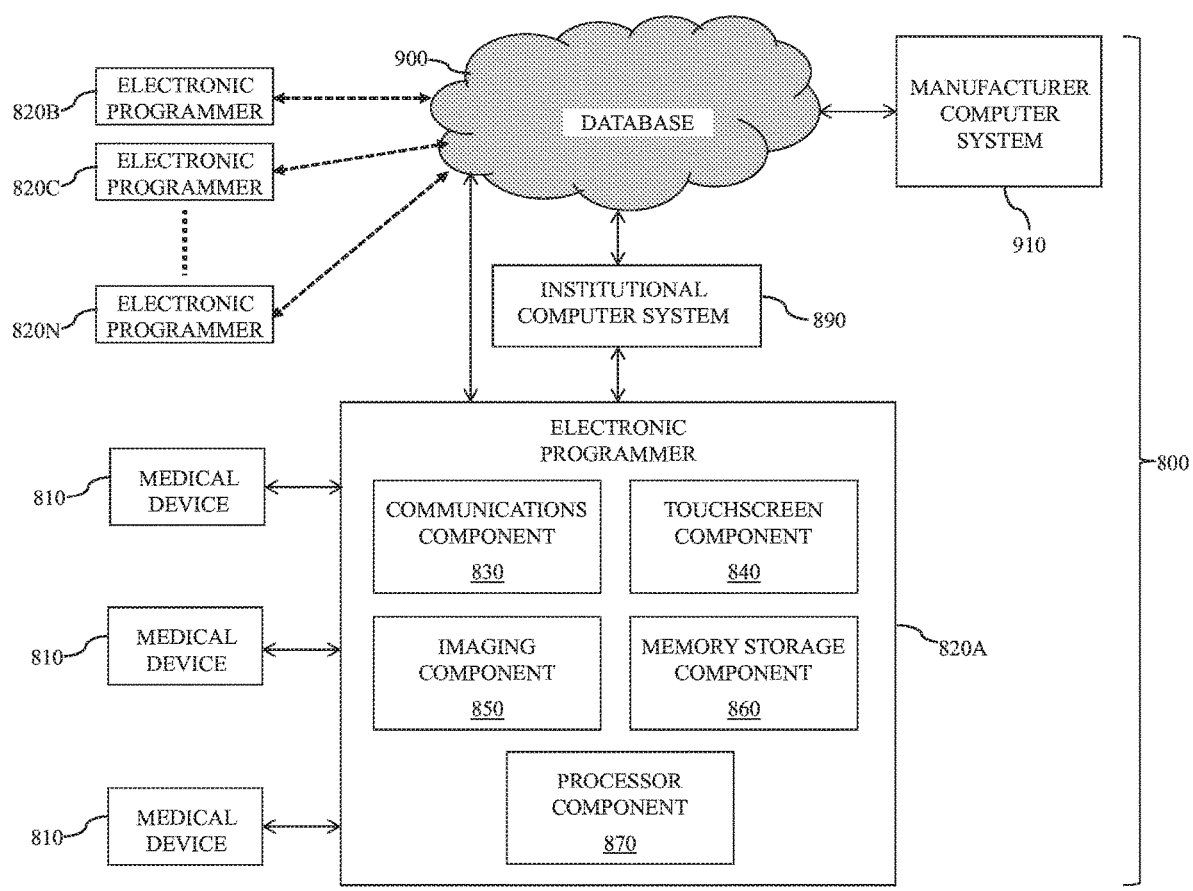
FIG. 56 is a simplified block diagram of a medical system/infrastructure according to various aspects of the present disclosure.

Referring now to FIG. 56, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 55), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 54. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 56 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, the pain/stimulation maps may be uploaded from the electronic programmer 820A to the database 900. The pain/stimulation maps saved in the database 900 may thereafter be downloaded by any of the other electronic programmers 820B-820N communicatively coupled to it, assuming the user of these programmers has the right login permissions. For example, after the 2D pain/stimulation map is generated by the electronic programmer 820A and uploaded to the database 900. That 2D pain/stimulation map can then be downloaded by the electronic programmer 820B, which can use the downloaded 2D pain/stimulation map to reconstruct or recreate a 3D pain/stimulation map. In this manner, a less data-intensive 2D pain/stimulation map may be derived from a data-heavy 3D pain/stimulation map, sent to a different programmer through the database, and then be used to reconstruct the 3D pain/stimulation map.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

FIG. 57A is a side view of a spine 1000, and FIG. 57B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 57B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 54.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method, comprising:
providing a hierarchical user interface on an electronic programming device for programming an implantable medical device, wherein the hierarchical user interface includes a plurality of user interface screens corresponding to a plurality of programming options or settings, and wherein the hierarchical user interface further includes a home screen from which each of the plurality of user interface screens may be launched and a user logon screen that is different from the user interface screens and the home screen, wherein the user logon screen is configured to log different users on to the electronic programming device;
detecting, while one of the user interface screens is being displayed, a first single user engagement of a home button;
automatically displaying the home screen in response to the detecting of the first single user engagement of the home button;
detecting, while the home screen is being displayed, a second user engagement of the home button; and
automatically displaying the user logon screen in response to the detecting of the second user engagement of the home button while the home screen is displayed;
detecting, while one of the user interface screens is being displayed, a double user engagement of the home button; and
automatically displaying the user logon screen in response to the detecting of the double user engagement of the home button.

2. The method of claim 1, wherein the user logon screen is located at a higher level of hierarchy than the home screen.

3. The method of claim 1, wherein the providing the hierarchical user interface comprises displaying a welcome screen that displays a greeting in response to the electronic programming device being turned on, and wherein the welcome screen is located at a higher level of hierarchy than the user logon screen.

4. The method of claim 1, wherein the providing the hierarchical user interface comprises displaying a new patient creation screen where information about a new patient can be entered, and wherein the new patient creation screen is located at a higher level of hierarchy than the home screen but at a lower level of hierarchy than the user logon screen.

5. The method of claim 1, wherein the providing the hierarchical user interface comprises displaying a virtual mechanism as the home button on each of the user interface screens.

6. The method of claim 1, wherein the home button is implemented as a physical button on the electronic programming device.

7. The method of claim 1, further comprising:
granting, to a super user and in response to a correct entry of an unchangeable super user password, privileges to change an administrative user password for an administrative user and a normal user password for a normal user;
granting, to the administrative user, access to an entirety of the hierarchical user interface in response to a correct entry of the super user password; and
granting, to the normal user, access to a subset, but not all, of the hierarchical user interface in response to a correct entry of the normal user password.

8. The method of claim 1, wherein the providing the hierarchical user interface comprises displaying a patient information edit screen where information about a patient can be edited, and wherein the patient information edit screen is located at a higher level of hierarchy than the home screen but at a lower level of hierarchy than the user logon screen.

9. An electronic programming device for programming an implantable medical device, the electronic programming device comprising:
a memory storage component configured to store programming code; and
a computer processor component configured to execute the programming code to perform operations that include:
providing a hierarchical user interface on the electronic programming device, wherein the hierarchical user interface includes a plurality of user interface screens corresponding to a plurality of programming options or settings, and wherein the hierarchical user interface further includes a home screen from which each of the plurality of user interface screens may be launched and a user logon screen that is different from the user interface screens and the home screen, wherein the user logon screen is configured to log different users on to the electronic programming device;

detecting, while one of the user interface screens is being displayed, a single click of a home button;

automatically displaying the home screen in response to the detecting of the single click of the home button;

detecting, while the home screen is being displayed, another single click of the home button; and automatically displaying the user logon screen in response to the detecting of the another single click of the home button while the home screen is displayed;

detecting, while one of the user interface screens is being displayed, a double click of the home button; and automatically displaying the user logon screen in response to the detecting of the double click of the home button.

10. The electronic programming device of claim 9, wherein the user logon screen is located at a higher level of hierarchy than the home screen.

11. The electronic programming device of claim 9, wherein the hierarchical user interface includes a welcome screen that displays a greeting in response to the electronic programming device being turned on, and wherein the welcome screen is located at a higher level of hierarchy than the user logon screen.

12. The electronic programming device of claim 9, wherein the hierarchical user interface includes a new patient creation screen for entering information regarding a new patient, and wherein the new patient creation screen is located at a higher level of hierarchy than the home screen but at a lower level of hierarchy than the user logon screen.

13. The electronic programming device of claim 9, wherein the home button is implemented as a physical button on the electronic programming device or as a virtual mechanism on each of the user interface screens.

14. The electronic programming device of claim 9, wherein the operations further include:

granting, to a super user and in response to a correct entry of an unchangeable super user password, privileges to change an administrative user password for an administrative user and a normal user password for a normal user;

granting, to the administrative user, access to an entirety of the hierarchical user interface in response to a correct entry of the super user password; and granting, to the normal user, access to a subset, but not all, of the hierarchical user interface in response to a correct entry of the normal user password.

15. The electronic programming device of claim 9, wherein the hierarchical user interface includes a patient information edit screen for editing information regarding a patient, and wherein the patient information edit screen is located at a higher level of hierarchy than the home screen but at a lower level of hierarchy than the user logon screen.

16. A medical system, comprising:

an implantable medical device configured to deliver an electrical stimulation therapy for a patient; and an electronic programming device for programming the implantable medical device, the electronic programming device includes a memory storage component configured to store programming code and a computer processor component configured to execute the programming code to perform operations that include:

providing a hierarchical user interface on the electronic programming device, wherein the hierarchical user interface includes:

a plurality of user interface screens corresponding to a plurality of programming options or settings;

a home screen from which each of the plurality of user interface screens may be launched;

a user logon screen that is different from the user interface screens and the home screen, wherein the user logon screen is configured to log different users on to the electronic programming device, and wherein the user logon screen is located at a higher level of hierarchy than the home screen; and a new patient creation screen that allows new patient information to be entered, wherein the new patient creation screen is located at a higher level of hierarchy than the home screen but at a lower level of hierarchy than the user logon screen;

detecting, while one of the user interface screens is being displayed, a user engagement of a home button;

automatically displaying the home screen in response to the detecting of the user engagement;

detecting, while the home screen is being displayed, another user engagement of the home button; and automatically displaying the user logon screen in response to the detecting of the another user engagement of the home button while the home screen is displayed.

17. The medical system of claim 16, wherein the hierarchical user interface includes:

a welcome screen that displays a greeting in response to the electronic programming device being turned on; wherein:

the welcome screen is located at a higher level of hierarchy than the user logon screen.

18. The medical system of claim 16, wherein the home button is implemented as a physical button on the electronic programming device or as a virtual mechanism on each of the user interface screens.

19. The medical system of claim 16, wherein the automatically displaying the home screen is performed in response to a detection of a single click of the home button as the detected user engagement of the home button, and wherein the operations further include:

detecting, while one of the user interface screens is being displayed, a double click of the home button; and automatically displaying the user logon screen in response to the detecting of the double click of the home button.

20. The medical system of claim 16, wherein the hierarchical user interface includes:

a patient information edit screen for editing information regarding a patient, wherein the patient information edit screen is located at a higher level of hierarchy than the home screen but at a lower level of hierarchy than the user logon screen.

* * * * *